United States Patent
Terman

(10) Patent No.: US 9,149,504 B2
(45) Date of Patent: Oct. 6, 2015

(54) COMPOSITIONS AND METHODS FOR TREATMENT OF NEOPLASTIC DISEASE

(76) Inventor: David Terman, Pebble Beach, CA (US)

(*) Notice: Subject to any disclaimer, the term of this patent is extended or adjusted under 35 U.S.C. 154(b) by 0 days.

(21) Appl. No.: 13/328,748

(22) Filed: Dec. 16, 2011

(65) Prior Publication Data

US 2012/0148627 A1 Jun. 14, 2012

Related U.S. Application Data

(60) Continuation-in-part of application No. 12/276,941, filed on Nov. 24, 2008, now Pat. No. 8,524,218, which is a division of application No. 10/428,817, filed on May 5, 2003, now abandoned, application No. 13/328,748, which is a continuation-in-part of application No. 12/145,949, filed on Jun. 25, 2008, now Pat. No. 7,803,637, which is a division of application No. 10/937,758, filed on Sep. 8, 2004, now abandoned, which is a continuation of application No. 09/650,884, filed on Aug. 30, 2000, now abandoned, application No. 13/328,748, which is a continuation-in-part of application No. 12/860,699, filed on Aug. 20, 2010, now abandoned, which is a continuation of application No. 12/145,949, which is a continuation of application No. 10/937,758, which is a continuation of application No. 09/650,884, said application No. 12/860,699 is a continuation-in-part of application No. 12/759,527, filed on Apr. 13, 2010, now Pat. No. 8,128,931, which is a continuation of application No. 10/513,466, filed as application No. PCT/US03/14381 on May 8, 2003, now Pat. No. 7,776,822, application No. 13/328,748, which is a continuation-in-part of application No. 13/317,590, filed on Oct. 20, 2011, now abandoned, which is a continuation-in-part of application No. 12/586,532, filed on Sep. 22, 2009, now abandoned, and a continuation-in-part of application No. 12/276,941, and a continuation-in-part of application No. 12/145,949, which is a division of application No. 10/937,758, which is a continuation of application No. 09/650,884, said application No. 12/276,941 is a division of application No. 10/937,758.

(60) Provisional application No. 60/378,988, filed on May 8, 2002, provisional application No. 60/389,366, filed on Jun. 15, 2002, provisional application No. 60/406,697, filed on Aug. 28, 2002, provisional application No. 60/406,750, filed on Aug. 29, 2002, provisional application No. 60/415,310, filed on Oct. 1, 2002, provisional application No. 60/415,400, filed on Oct. 2, 2002, provisional application No. 60/438,686, filed on Jan. 9, 2013, provisional application No. 60/151,470, filed on Aug. 30, 1999, provisional application No. 61/455,592, filed on Oct. 20, 2010, provisional application No. 61/192,949, filed on Sep. 22, 2008, provisional application No. 61/206,338, filed on Jan. 28, 2009, provisional application No. 61/211,227, filed on Mar. 28, 2009, provisional application No. 61/215,906, filed on May 11, 2009, provisional application No. 61/462,622, filed on Feb. 3, 2011.

(51) Int. Cl.

| | |
|---|---|
| A61K 48/00 | (2006.01) |
| A61K 38/16 | (2006.01) |
| A61K 39/00 | (2006.01) |
| A61K 39/085 | (2006.01) |
| A61K 45/06 | (2006.01) |
| C12N 15/86 | (2006.01) |
| C12N 15/863 | (2006.01) |

(52) U.S. Cl.
CPC ............ *A61K 38/164* (2013.01); *A61K 39/0011* (2013.01); *A61K 39/085* (2013.01); *A61K 45/06* (2013.01); *A61K 48/00* (2013.01); *A61K 48/005* (2013.01); *C12N 15/86* (2013.01); *C12N 15/8636* (2013.01)

(58) Field of Classification Search
CPC ..... A61K 48/00; A61K 38/164; C12N 15/86; C12N 15/8636
USPC .......... 514/44; 530/350; 435/320.1; 536/23.5
See application file for complete search history.

(56) References Cited

PUBLICATIONS

Hansson et al. (Proc Natl Acad Sci U S A. Mar. 18, 1997; 94 (6): 2489-94).*
Si et al. (Gene Ther. Nov. 2006; 13 (22): 1603-10).*

* cited by examiner

*Primary Examiner* — Stephen Rawlings

(57) ABSTRACT

Herein we provide cDNA extracted from tumor cells, normal cells or treatment resistant tumor cells that have been transduced with virus capable of altering self and/or tumor associated antigens (VASTA) fused recombinantly to nucleic acids encoding wild type superantigens, superantigens, superantigen homologues and superantigen-tumor specific targeting molecules and further linked to a costimulatory molecule. The extracted cDNA is linked to a VASTA and delivered to tumor bearing hosts parenterally wherein they induce a tumoricidal response. These agents are also incorporated into a tumor tropic cell carrier for protected delivery to tumor.

7 Claims, 4 Drawing Sheets

Site of SAg-Costimulatory nucleic acid insert

VSV 3'  N | P | M | G | L  5'

FIGURE 1

COMPOSITIONS AND METHODS FOR TREATMENT OF NEOPLASTIC DISEASE

CROSS REFERENCE TO RELATED DOCUMENTS

The instant application is a continuation in part of U.S. patent application Ser. No. 12/276,941 which is a divisional of U.S. application Ser. No. 10/428,817, filed on May 5, 2003, which claims priority to provisional applications 60/378,988, filed May 8, 2002, 60/389,366, filed Jun. 15, 2002, 60/406,697, filed Aug. 28, 2002, 60/406,750, filed Aug. 29, 2002, 60/415,310, filed Oct. 1, 2002, 60/415,400, filed Oct. 2, 2002, and 60/438,686, filed Jan. 9, 2003. All of these patent and patent applications are incorporated in their entirety by reference.

The instant application is also a continuation in part of divisional Ser. No. 12/145,949, filed on Jun. 25, 2008, which is a divisional of U.S. application Ser. No. 10/937,758, filed on Sep. 8, 2004, which is a continuation of U.S. application Ser. No. 09/650,884, filed on Aug. 30, 2000, which claims priority to provisional application 60/151,470, filed on Aug. 30, 1999. All of these patent and patent applications are incorporated in their entirety by reference.

The instant application is also a continuation in part of U.S. patent application Ser. No. 12/860,699 filed Aug. 20, 2010 which is a continuation of divisional application Ser. No. 12/145,949, filed on Jun. 25, 2008, which is a continuation of application Ser. No. 10/937,758, filed Sep. 8, 2004 and abandoned, which is a continuation of application Ser. No. 09/650,884, filed on Aug. 30, 2000 and abandoned, which claims priority to provisional application No. 60/151,470, filed on Aug. 30, 1999. All of these patents and patent applications are incorporated in their entirety by reference.

The instant application is also a continuation in part of U.S. patent application Ser. No. 12/860,699 filed Aug. 20, 2010 which is a continuation in part of U.S. patent application Ser. No. 12/759,527 filed Apr. 13, 2010 which is a continuation of U.S. patent Ser. No. 10/513,466 issued Aug. 17, 2010 which is a continuation of PCT/US03/14381 filed May 8, 2003. All of these patents and patent applications are incorporated in entirety with their references by reference.

The present application is also a continuation in part of U.S. patent application Ser. No. 13/317,590 filed Oct. 20, 2011 which is a continuation in part of U.S. provisional application Ser. No. 61/455,592 filed Oct. 20, 2010 which is a continuation in part of U.S. patent application Ser. No. 12/586,532 filed Sep. 22, 2009 and continuations in part of Ser. No. 12/276,941 filed Nov. 24, 2008 and Ser. No. 12/145,949 filed Jun. 25, 2008 which are divisionals of U.S. patent application Ser. No. 10/937,758 filed Sep. 8, 2004 which is a continuation of U.S. patent application Ser. No. 09/680,884 filed Aug. 30, 2000 which is a continuation of U.S. provisional patent application 60/151,470 filed Aug. 30, 1999. All of these patents and patent applications are incorporated in entirety with their references by reference.

The instant application claims priority to U.S. provisional application Ser. No. 61/462,622 filed Feb. 3, 2011 and U.S. patent application Ser. No. 61/455,592 filed on Oct. 20, 2010, U.S. patent application Ser. No. 12/586,532 and U.S. provisional application Ser. No. 61/215,906 filed May 11, 2009 and U.S. provisional application Ser. No. 61/211,227 filed Mar. 28, 2009 and U.S. provisional application Ser. No. 61/206,338 filed on Jan. 28, 2009 and U.S. provisional application Ser. No. 61/192,949 filed on Sep. 22, 2008 and PCT/US07/69869 filed May 29, 2007 which is a continuation in part of U.S. patent application Ser. No. 10/428,817, filed May 5, 2003 and U.S. provisional application Ser. No. 60/809,553 filed on May 30, 2006 and U.S. provisional application Ser. No. 60/819,551 filed on Jul. 8, 2006 and U.S. provisional application Ser. No. 60/842,213 filed on Sep. 5, 2006 and U.S. provisional application Ser. No. 60/438,686, filed Jan. 9, 2003 and U.S. provisional application Ser. No. 60/415,310, filed on Oct. 1, 2002 and U.S. provisional application Ser. No. 60/406,750, filed on Aug. 29, 2002 and U.S. provisional application Ser. No. 60/415,400, filed on Oct. 2, 2002 and U.S. provisional application Ser. No. 60/406,697, filed on Aug. 28, 2002 and U.S. provisional application Ser. No. 60/389,366, filed on Jun. 15, 2002 and U.S. provisional application Ser. No. 60/378,988, filed on May 8, 2002 and U.S. patent application Ser. No. 09/870,759 filed on May 30, 2001 which is a continuation in part of U.S. patent application Ser. No. 09/640,884 filed Aug. 30, 2000 and U.S. provisional patent application Ser. No. 60/151,470 filed on Aug. 30, 1999. All of these patents and patent applications are incorporated in entirety with their references by reference.

BACKGROUND

Therapy of the neoplastic diseases has largely involved the use of chemotherapeutic agents, radiation, and surgery. However, results with these measures, while beneficial in some tumors, has had only marginal effects in many patients and little or no effect in many others, while demonstrating unacceptable toxicity. Hence, there has been a quest for newer modalities to treat neoplastic diseases.

The Staphylococcal enterotoxins are a representative of a family of evolutionarily-related extracellular products of Staphylococcal *aureus* that belong to a well recognized group of proteins that have common physical and chemical and biologic properties known as superantigens. These proteins are which are the most powerful T cell mitogens known capable of activating 5 to 30% or the total T cell population compared to 0.01% for conventional antigens. Moreover, the enterotoxins evoke strong polyclonal T cell proliferation at concentrations $10^3$-fold lower than conventional T cell mitogens. The most potent enterotoxin, Staphylococcal enterotoxin A (SEA), has been shown to stimulate DNA synthesis in human T cells at concentrations of as low as $10^{-13}$ to $10^{-16}$M. Enterotoxin-activated T cells produce a variety of cytokines, including IFNγ, IL-2 and TNFα. The Staphylococcal enterotoxins share common physicochemical properties such as heat stability, trypsin resistance, and solubility in water and salt solutions. Furthermore, the Staphylococcal enterotoxins have similar sedimentation coefficients, diffusion constants, partial specific volumes, isoelectric points, and extinction coefficients.

The enterotoxins are composed of a single polypeptide chain of about 30 kilodaltons (kD). SEA, SEB, SEC, SED, Staphylococcal toxic shock-associated toxin (TSST-1 also known as SEF), and the Streptococcal exotoxins share considerable nucleic acid and amino acid sequence homology. All staphylococcal enterotoxins have a characteristic disulfide loop near the middle of the molecule. SEA is a flat monomer consisting or 233 amino acid residues divided into two domains. Domain I comprises residues 31-116 and domain II of residues 117-233 together with the amino tail 1-30. In addition, the biologically active regions of the proteins are conserved and show a high degree of homology.

T cell recognition of SAgs, such as SEs, via the TCR Vβ region is independent of other TCR components and T cell diversity elements in a manner distinct from conventional antigens. Unlike conventional polypeptide antigens T cell activation by these molecules does not require antigen processing by an antigen presenting cell. They activate T cells by a biochemical signaling pathway distinct from conventional peptide antigens.

Single amino acid positions and regions important for SAg-TCR interactions have been defined. These residues are located in the vicinity of the shallow cavity formed between the two SE domains. (Lavoie P M et al., *Immunol. Rev.* 168: 257-269 (1999). SEB and the SEC bind only to the MHC class II β chain whereas SEA, SEE and SED, also interact with the MHC class II α chain in a zinc dependent manner. Substitution of amino acid residue Asn23 in SEB by Ala has demonstrated the importance of this position in SEB/TCR interactions. This particular residue is conserved among all of the SE's and may constitute a common anchor position for SE interaction with TCR Vβ structures. Amino acid residues in positions 60-64 of SEA contribute to the TCR interaction as do the Cys residues forming the intramolecular disulfide bridge (Kappler J et al., *J. Exp. Med.* 175 387-96 (1992)). For SEC2 and SEC3, the key points of interaction in the TCR Vβ region are located in the CDR1, CDR2 and HRV4 regions of the TCR Vβ3 chain (Deringer J R et al., *Mol. Microbiol.* 22: 523-534 (1996)). Hence, multiple and highly variable parts of the Vβ region contribute to the formation of the TCRs SE binding site. This distinctive binding mechanism of enterotoxins which bypasses the highly variable parts of the MHC class II and TCR molecules allows them to activate a high frequency of T cells resulting in massive lymphoproliferation, cytotoxic T cell generation and TH1 cytokines cytokine induction. Hence a given can activate up to 30% of resting T cells compared to 0.01% for conventional antigens.

Thus far, no single, linear consensus motif in the TCR vβ displaying a high affinity interaction with particular enterotoxins has been identified. A significant contribution of the TCRα chain in SE-TCR recognition is acknowledged (Smith et al., *J. Immunol.* 149: 887-896 (1992)). Unlike peptide binding in the groove between the MHCII alpha and beta chain, the SEs bypass the highly variable parts of the MHC class II and bind instead on the outer face of the groove. This distinctive binding to non-polymorphic regions of the MHCII endows them with their ability to activate such a high frequency of T cells and cause massive proliferation, cytokine induction and cytotoxic T cell generation. These properties are shared by several other proteins produced by various infectious agents. Together, these proteins form a well recognized family of molecules, SAgs, because of their aforementioned biological effects. Summary of the superantigen sequences that bind MHCII and vβ TCR regions is provided in Papageorgiou, A. C. et al. EMBO J. 18:9-21 (1999))

Wild type SEs and SE homologues and fusion proteins are known to induce anti-tumor effects. Administration of SEB produced antitumor effects against established tumors in two animal species, rabbits and mice, with tumors of five different histologic types: rabbit VX-2 carcinoma (Terman et al., U.S. Pat. No. 6,126,945; Terman, U.S. Pat. No. 6,340,461), murine CL 62 melanomas (Penna C. et al., *Cancer Res.* 54: 2738-2743 (1994)), murine A/20 lymphoma (Kalland T. Declaration in U.S. Ser. No. 07/689,799 (1992)), murine PRO4L fibrosarcoma (Newell et al., *Proc Natl. Acad. Sci.* 88: 1074-1079 (1991)) and human SW 620 colon carcinoma (Dohlsten et al., *Eur. J. Immunol.* 21: 1229-1233 (1991)). In these studies, parenterally-administered SEB induced objective antitumor effects at primary and metastatic sites. SEB was used ex vivo to stimulate a population of T cells pre-exposed to tumor, which, upon re-infusion into host animals with established pulmonary metastases, induced a substantial reduction of metastases. SEB activated T cell anti-tumor effect was specific for the immunizing tumor; the SEB stimulated T cells produced IFNγ which was thought to be an important mediator of the anti-tumor effect (Shu S et al., *J. Immunol.* 152: 1277-88 (1994)). Fusion polypeptides comprising SEA fused to a tumor specific monoclonal antibody (mAb), designated "SEA-mAb," induced tumoricidal responses in the murine B16 melanoma model (Dohlsten M et al., *Proc Natl Acad Sci* 91:8945-9 (1994); Dohlsten M et al., *Proc. Natl. Acad. Sci.* 88:9287-91(1991). A summary of antitumor effects of superantigens is provided in Terman et al *Clin Chest Med* 27: 321-334 (2006).

The instant application provides a heretofore undescribed role for superantigens of boosting the tumoricidal response when fused recombinatly to a tumor associated antigen (TAA). Because superantigen and conventional antigens are aligned in geometrically different conformations on MHC II molecules required for activation of T cells such a fusion molecule would sterically interdict the binding of one of both its components to the MHCII receptor. Surprisingly, as shown herein in Example 1 and U.S. application Ser. No. 10/428,817 (of which the instant application is continuation in part) a nucleic acid construct encoding a superantigen fused to a weak TAA (papilloma viral epitope) abolished the outgrowth of squamous cell carcinoma in rabbits whereas nucleic acids encoding a superantigen or the viral epitope alone were ineffective. Further, parenteral delivery of tumor cells transduced with superantigen and a costimulatory molecule produced a tumoricidal response whereas mock transfected tumor cells similarly administered were ineffective (PCT/IS99/08399). Similarly, Bridle et al., (*Mol Ther* 18: 1430-1439 (2010) showed that immunization and boosting with a viral-nucleic acids encoding tumor associated antigen (TAA) construct resulted in a potent T cell response to the TAA and a tumoricidal effect that was not seen with the virus or tumor antigen alone. These results suggest that both superantigens and certain viruses (selected to induce altered self antigens) can combine with tumor associated epitopes to augment their immunogenicity in the host leading to an antitumor effect.

Thus, in the present invention nucleic acids encoding superantigens are fused to virus or viral genomic DNA (VASTA) capable of altering both tumor associated and self antigens upon transfection into tumor cells and normal cells of similar histologic type. This construct is used to transduce both tumor cells and normal cells of the same histologic type as the tumor. The cDNA from these cells is extracted from such cells and linked recombinantly to the original virus or a new VASTA and administered parenterally to the host. The final product consists of nucleic acids encoding a library of superantigen- and viral-altered normal and tumor cell associated antigens some of which are expressed as fusion proteins with the virus or superantigen. We hypothesize that the extracted cDNA containing nucleic acids encoding viral and/or SAg altered tumor associated self antigens is rendered highly immunogenic in the host by structural modification and/or fusion with the virus and the SAg. Systemic delivery of SAg-viral based nucleic acid libraries induce a broad repertoire of individually weak T cell responses against multiple TAAs resulting in a cumulatively powerful anti-tumor effect.

The present invention therefore exploits the ability of some viruses such as vesicular stomatitis virus to alter self antigens and render them immunogenic. cDNA from normal cells are used because cells transduced with virus express altered self antigens that when exposed to the host induce an immune response to antigen loss variants of tumor derived from these normal cells (Sanchez-Perez L et al., *Caner Res* 65: 2005-2017 (2009)). In addition, the present invention provides cDNA extracted from treatment resistant tumor cells because these cells express additional tumor epitopes such as cadherin and adhesion molecules not present on the original tumor or normal cells of the same histologic type or the primary tumor cells.

This unique therapeutic nucleic acid constructs derived from VASTA-SAg transfected tumor cells and normal cells of the same histologic type differs from viral constructs previously reported to treat cancer. Schlom et al discloses tumor cells transduced with nucleic acid construct comprising a virus-tumor associated antigen and costimulatory molecules that are administered directly into the tumor bearing host. In contrast to the instant invention, this nucleic construct does not contain a superantigen, is not extracted from transduced tumor cells and normal cells of the same histologic type, does not contain a library of superantigen/viral altered normal and tumor associated self antigens and uses an intact tumor cell as the therapeutic agent. Terman et al. (U.S. application Ser. No. 10/428,817) disclose administration of tumor cells transduced with nucleic acids encoding a superantigen and costimulatory molecules which differs from the instant invention in that it does not contain a virus and uses the transduced tumor cell as the therapeutic agent instead of cDNA extracted from VASTA-SAg transduced tumor cells and normal cells used in the instant application. Dow S W et al., (*J Clin Invest* 101:2406-43(1998) and Thamm D H et al., (*Cancer Immunol Immunother* 52:473-80 (2003)) disclose lipid complexed plasmid DNA encoding SEB and either granulocyte-macrophage colony-stimulating factor or IL-2 but this construct does not comprise tumor or normal cell-derived cDNA and is devoid of a virus selected to induce altered self antigens. To treat cancer, others have used fusion genes consisting of one or defined group of tumor/self antigens while some have used plasmid vectors that encode tumor antigens as in-frame chimeric fusions with other immune proteins (Englehorn et al., Mol. Ther. 16: 773-781 (2008)). None of these fusion agents however, use a superantigen in the fusion construct and none employ a complete cDNA library of modified self and tumor antigens extracted from tumor cells transduced with nucleic acids encoding SAg and VASTA.

In contrast to all of the above art, the cDNA extracted from tumor cells and normal cells and delivered to tumor bearing host contains not only nucleic acids encoding VASTA-SAg but also nucleic acids encoding self and tumor associated epitopes altered by VASTA-SAg. The immunogenicity of the altered TAAs and self epitopes are thereby augmented sufficiently to evoke a tumoricidal response. Unlike previous reports, the host is presented directly with the nucleic acids encoding a complete library of highly immunogenic self and TAAs together with the potent T cell adjuvant effects of SAg and a virus (VASTA) selected to induce altered self antigens in tumor cells and normal cells. To our knowledge, these nucleic acid therapeutic constructs encoding a library of altered self and tumor epitopes together with viral-superantigen-costimulatory molecules have not been previously employed to treat tumors.

BRIEF DESCRIPTION OF THE DRAWINGS

FIG. 1. The VSV cloning vector. The genome of the parental VSVrwt vector is diagrammed in a 3'-to-5' orientation on the negative-stranded viral RNA genome. Letters refer to the VSV nucleocapsid (N), phosphoprotein (P), matrix (M), glycoprotein (G), and RNAdependent RNA polymerase (L) genes. The SAg-costimulatory genes are inserted into position 5 of the VSV genome, between the G and L genes, and expressed by duplication of the VSV start and stop signals. The superantigen is representative of any superantigen, superantigen homologue or superantigen fusion protein and preferably contain a tumor targeting structure such as a ligand for a tumor associated receptor or a tumor specific antibody. Superantigens which have no or minimal naturally-occurring antibody reactivity in humans are preferred. The VSV is an archetypical VASTA but any other virus with this property capable of incorporating a SAg is useful including but not limited to herpes virus, reovirus, adenovirus, measles, vesicular stomatitis virus, Sindbis virus, parvovirus, Newcastle Disease virus, vaccinia virus including modified viruses as shown in Table 1.

SUMMARY OF INVENTION

Figure 2:
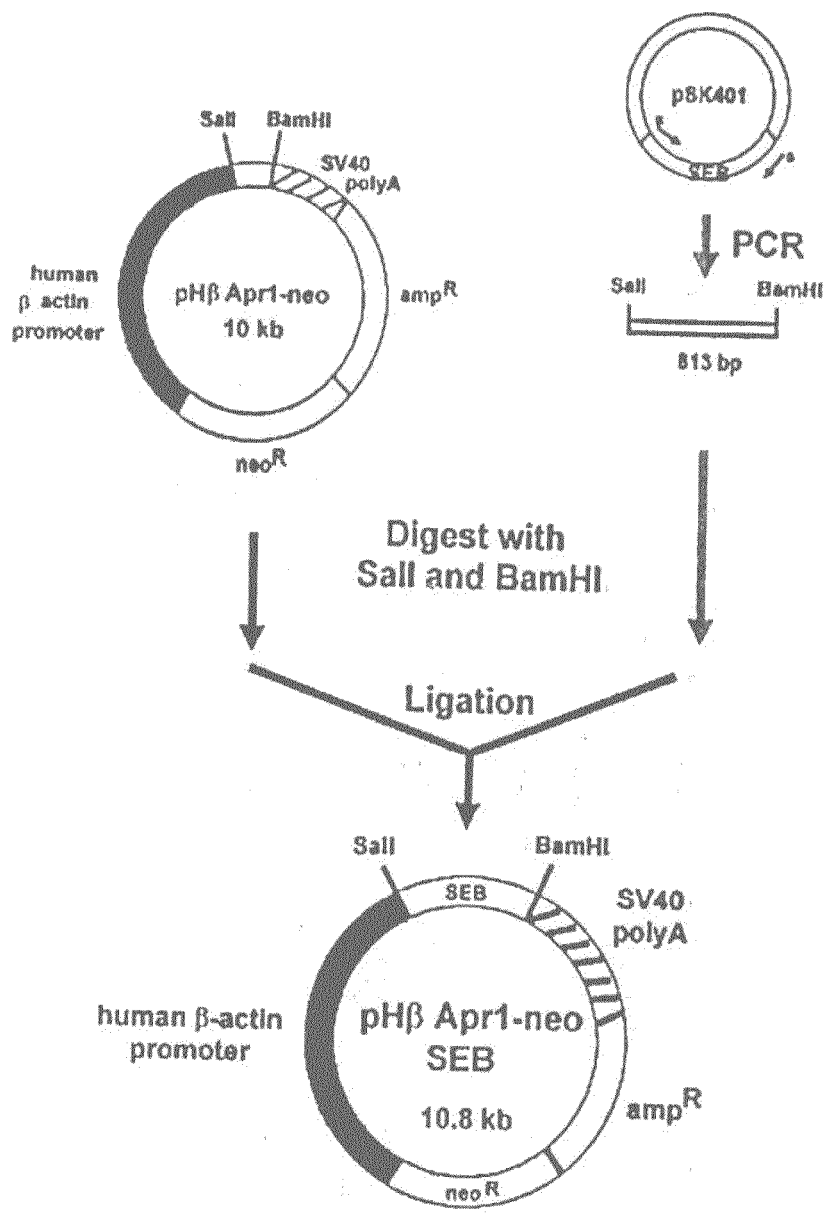
FIG. 2. Schematic diagram of the cloning of the SEB gene into the pHβ Apr1-neo vector. The coding region of the SEB gene was amplified with the PCR primers. The upstream primer (SEB1) has a SaiI site at its 5' end and the downstream primer (SEB2), a BamIII site. Both the pHβ Apr1-neo vector and the amplified SEB insert were digested with SAiI and BamIII, ligated and transformed in the Xl10Blue competent cells. The final construct was verified by restriction enzyme and sequence analyses.

Provided herein are nucleic acid constructs for treatment of cancer. Construct 1 consists of a virus or its genomic viral DNA incorporating nucleic acids encoding a wild type superantigens, a superantigen homologue or a fusion protein consisting superantigen-tumor specific targeting (collectively SAg) and a costimulatory molecule. This construct is used to transduce tumor cells, normal cells (preferably of the same histologic type as the tumor cells) and tumor cells that are resistant to standard cancer treatment. These cells may be allogeneic, syngeneic or xenogeneic to the host. Constructs 2, 3 and 4 comprise cDNA extracted from said transduced tumor cells, treatment-resistant tumor cells and normal cells respectively integrated recombinantly into a virus or viral genomic DNA. Constructs 2, 3 and 4 are administered to tumor bearing hosts parenterally, intratumorally, intravenously, intrapleurally, intraperitoneally, intracutaneously, intramuscularly and intrathecally and induce a tumoricidal response. The preferred superantigen and virus used in the Constructs 1-4 possess negligible neutralizing antibody reactivity in human sera. To further protect these constructs from neutralizing antibodies in human sera, they are also incorporated recombinantly into cellular carriers with tumor tropism such as sickled erythroblasts or sickled erythrocytes.

DETAILED DESCRIPTION

Virus-SAg-Costimulatory Nucleic Acid Construct Comprising VASTA Incorporating Nucleic Acids Encoding a Wild Type SAg, SAg Homologue or SAg Fusion Protein and a Costimulatory Molecule The present invention uses three key constructs to induce a tumoricidal response:

i. Construct 1 consists of a VASTA or viral genomic DNA fused recombinantly to a SAg and a costimulatory molecule. This construct is used to infect syngeneic, autologous, allogeneic or xenogeneic tumor cells or normal cells preferably of the same histologic type as the tumor or from which the tumor is derived.

ii. Constructs 2 and 3 consist of cDNA extracted from such transduced tumor cells or normal cells respectively. Each cDNA is incorporated recombinantly and operatively linked to a VASTA or its genomic DNA and administered to the host.

iii. Construct 4 consists of cDNA extracted from treatment resistant tumor cells that have been transduced with construct 1. Treatment resistant tumor cells are defined as tumor cells that normally multiply but exhibit no or minimal cytostatic or cytotoxic response to therapeutic doses of chemotherapy, immunotherapy or radiation therapy in vitro or in vivo.

VASTA as used herein refers to viruses capable of altering self and/or tumor associated antigens alone and/or when operatively linked to nucleic acids encoding a wild type SAg, SAg homologue or SAg fusion protein.

Constructs 2, 3 and 4 are delivered into hosts bearing tumors displaying the original tumor phenotype. They are administered parenterally, preferably intravenously by infusion or injection. They may also be administered intramuscularly, intradermally, intrapleurally, intraperitoneally They are administered parenterally, preferably intravenously by infusion or injection. They may also be administered intramuscularly, intradermally, intrapleurally, intraperitoneally, intrathecally intravesicularly, intratumorally or intra-lymph node. They may be delivered into a lymph node tumor draining lymph node with or without tumor or intratumorally tumor at one or more sites.

Delivery can be by one or any two of the above routes simultaneously or sequentially. They can be delivered simultaneously on a daily schedule for up to 50 days or sequentially as individual infusion/injections on successive days for up to 75 days.

Tumor Cells, Normal Cells of the Same Histologic Type and Tumor Cells Refractory to Cancer Treatment Tumor cells can be obtained can be obtained from a spontaneous tumor which has arisen, e.g., in a human subject or they may be obtained from experimentally derived or induced tumor, in an animal subject. The tumor cells can be an established tumor cell line having an identical tissue type as the tumor of said tumor-bearing subject. It need not be HLA class II matched to said subject. Further, the tumor cells can be obtained, for example, from a solid tumor of an organ, such as a tumor of the lung, liver, breast, colon, bone, etc. The tumor cells can also be obtained from a blood-borne (i.e., dispersed) malignancy, such as a lymphoma, a myeloma or a leukemia.

Tumor cells can also be obtained from a subject by, for example, surgical removal of tumor cells, e.g., a biopsy of the tumor, or from a blood sample from the subject in cases of blood-borne malignancies. In the case of an experimentally induced tumor, the tumor cells used to induce the tumor can be used, e.g., cells of a tumor cell line. Tumor samples of solid tumors may be treated prior to modification to produce a single-cell suspension of tumor cells for maximal efficiency of transfection. Possible treatments include manual dispersion of cells or enzymatic digestion of connective tissue fibers, e.g., by collagenase. The tumor cells can be transfected immediately after being obtained from the subject or can be cultured in vitro prior to transfection to allow for expansion and further characterization of the tumor cells (e.g., determination of the expression of cell surface molecules).

The tumor cells of the present invention which are transfected with the virus comprising SAg may comprise any tumor cell including but not limited to those derived from carcinomas, sarcomas, lymphoma, glioma, melanoma, neuroblastoma and the like. Examples of such methods include electroporation, calcium-phosphate precipitation, DEAE-dextran treatment, lipofection, microinjection and infection with viral vectors. These methods of transfection of mammalian cells are well-known in the art, and are described, e.g., in Sambrook et al, Molecular Cloning: A Laboratory Manual, 2nd Edition, Cold Spring Harbor Laboratory press (1989).

Normal cells of the same histologic type as the tumor are also useful in this invention as described above in Constructs 2 and 3. They can be syngeneic, allogeneic or xenogeneic to the host. Such cells are transduced the SAg-viral construct, their cDNA extracted and fused to a virus or viral genomic DNA for parenteral administration to the host in the same fashion as the tumor cells described above. They are delivered in a regimen that comprises cDNA extract from tumor cells similarly treated with SAg-viral constructs.

Tumors that regrow after immunotherapy show a different phenotype from the original tumor. Indeed, immunotherapy resistant TC2R tumors lost, or showed reduced expression of mouse homologs of the human RNAs encoding prostate-specific antigens in the original tumor as well as increased expression of N-cadherin, SNAIL and SLUG, associated with an epithelial-mesenchymal-like transition. The present invention contemplates infecting these cells with construct 1 and extracting the cDNA and incorporating it into a viral vector or viral genome for administration to tumor bearing hosts. This construct 4 may be administered at the time of initial tumor recognition along with the construct 2 derived from cDNA derived from normal cells transduced with construct 1. Methods of preparation of the constructs is given in Examples 1, 2 and 9.

The present invention also contemplates a hybrid cell made from fusion of a tumor cell and any normal cell or preferably a normal cell of the same histologic type as the tumor. These cells are transformed or transfected with a VASTA-SAg-costimulatory molecules and their phenotypes established by the retention of normal cell characteristics, tumor cell antigens and the expression of SAg and costimulatory molecules as described in Example 2 herein.

Production and Isolation of Superantigen Nucleic Acids for VASA Constructs

The SAg nucleic acids in Construct 1 may be in the form of nucleic acids encoding a wild type SAg, a SAg homologue or a SAg fusion protein in which a wild type SAg or SAg homologue is fused genetically to nucleic acids encoding a tumor targeting molecule such as a tumor specific antibody, antibody fragment or ligand for a tumor receptor or a coaguligand. The nucleic acid encoding the SAg homologue or fusion protein is defined herein as structurally exhibiting a z value in FASTA>13 vs. nucleic acids encoding a wild type superantigen and functionally demonstrating vβ specific T cell mitogenicity. Nucleic acids encoding the egc SEs, enterotoxins G, I, M, N, O, their homologues and fusion proteins are preferred. Each of these SEs has structurally modified MHC class II binding site(s) to reduce its affinity for MHC II+ cells which is known to reduce SE reduce SE toxicity in vivo by attenuating the MHCII dependent T cell cytokine production.

Nucleic acids encoding the SAgs their sequences and biological activities are well established and disclosed in the following references: Borst D W et al., *Infect. Immun.* 61: 5421-5425 (1993); Couch J L et al., *J. Bacteriol.* 170: 2954-2960 (1988); Jones, C L et al., *J. Bacteriol.* 166: 29-33 (1986); Bayles K W et al., *J. Bacteriol.* 171: 4799-4806 (1989); Blomster-Hautamaa D A et al., *J. Biol. Chem.* 261:15783-15786 (1986); Johnson, L P et al., *Mol. Gen. Genet.* 203, 354-356 (1986); Bohach G A et al., *Infect. Immun.* 55: 428-433 (1987); Iandolo J J et al., *Methods Enzymol* 165:43-52 (1988); Spero L et al., *Methods Enzymol* 78(Pt A):331-6 (1981); Blomster-Hautamaa D A, *Methods Enzymol* 165: 37-43 (1988); Iandolo J J Ann. Rev. Microbiol. 43: 375-402 (1989); U.S. Pat. No. 6,126,945 and U.S. provisional patent application 60/389,366 filed Jun. 15, 2002. We incorporate below amino acid sequences of the native SAg referred to in this invention. The corresponding nucleic acid sequences are found in the references above or in those just above each recorded sequence. All of these references and the references cited therein are incorporated by reference in their entirety.

These SAgs are Staphylococcal enterotoxin A (SEA), Staphylococcal enterotoxin B (SEB), Staphylococcal enterotoxin C (SEC—actually three different proteins, SEC1, SEC2 and SEC3)), Staphylococcal enterotoxin D (SED), Staphylococcal enterotoxin E (SEE) and toxic shock syndrome toxin-1 (TSST-1) (U.S. Pat. No. 6,126,945 and U.S. provisional patent application 60/389,366 filed Jun. 15, 2002, and the references cited therein). The amino acids sequences of the above group of native (wild-type) SAgs are provided below:

```
SEA (Huang, I. Y. et al., J. Biol. Chem. 262: 7006-7013 (1987))
                                                          [SEQ ID NO: 1]
  1 SEKSEEINEK DLRKKSELQG TAGNKQIY YYNEKAKTEN KESHDQFLQH TILFKGFFTD

61 HSWYNDLLVD FDSKDIVDKY KGKKVDLYGA YYGYQCAGGT PNKTACMYGG VTLHDNNRLT

121 EEKKVPINLW LDGKQNTVPL ETVKTNKKNV TVQELDLQAR RYLQEKYNLY NSDVFDGKVQ

181 RGLIVFHTST EPSVNYDLFG AQGQYSNTLL RIYRDNKSIN SENMHIDIYL YTS

SEB (Papageorgiou, A. C. et al. J. Mol. Biol. 277: 61-79 (1998))
                                                          [SEQ ID NO: 2]
  1 ESQPDPKPDE LHKSSKFTGL MENMKVLYDD NHVSAINVKS IDQFLYFDLI YSIKDTKLGN

61 YDNVRVEFKN KDLADKYKDK YVDVFGANYY YQCYFSKKTN DINSHQTDKR KTCMYGGVTE

121 HNGNQLDKYR SITVRVFEDG KNLLSFDVQT NKKKVTAQEL DYLTRHYLVK NKKLYEFNNS

181 PYETGYIKFI ENENSFWYDM MPAPGDKFDQ SKYLMMYNDN KMVDSKDVKI EVYLTTKK

SEC1 (Bohach, GA et al., Mol. Gen. Genet. 209: 15-20 (1987))
                                                          [SEQ ID NO: 3]
  1 MNKSRFISCV ILIFALILVL FTPNVLAESQ PDPTPDELHK ASKFTGLMEN MKVLYDDHYV

61 SATKVKSVDK FLAHDLIYNI SDKKLKNYDK VKTELLNEGL AKKYKDEVVD VYGSNYYVNC

121 YFSSKDNVGK VTGGKTCMYG GITKHEGNHF DNGNLQNVLI RVYENKRNTI SFEVQTDKKS

181 VTAQELDIKA RNFLINKKNL YEFNSSPYET GYIKFIENNG NTFWYDMMPA PGDKFDQSKY

SEC2 (Papageorgiou, A. C., et al., Structure 3: 769-779 (1995))
                                                          [SEQ ID NO: 4]
  1 ESQPDPTPDE LHKSSEFTGT MGNMKYLYDD HYVSATKVMS VDKFLAHDLI YNISDKKLKN

61 YDKVKTELLN EDLAKKYKDE VVDVYGSNYY VNCYFSSKDN VGKVTGGKTC MYGGITKHEG

121 NHFDNGNLQN VLIRVYENKR NTISFEVQTD KKSVTAQELD IKARNFLINK KNLYEFNSSP

181 YETGYIKFIE NNGNTFWYDM MPAPGDKFDQ SKYLMMYNDN KTVDSKSVKI EVHLTTKNG

SEC3 (Hovde, C. J. et al., Mol. Gen. Genet. 220: 329-333 (1990))
                                                          [SEQ ID NO: 5]
  1 MYKRLFISRV ILIFALILVI STPNVLAESQ PDPMPDDLHK SSEFTGTMGN MKYLYDDHYV

61 SATKVKSVDK FLAHDLIYNI SDKKLKNYDK VKTELLNEDL AKKYKDEVVD VYGSNYYVNC

121 YFSSKDNVGK VTGGKTCMYG GITKHEGNHF DNGNLQNVLV RVYENKRNTI SFEVQTDKKS

181 VTAQELDIKA RNFLINKKNL YEFNSSPYET GYIKFIENNG NTFWYDMMPA PGDKFDQSKY

241 LMMYNDNKTV DSKSVKIEVH LTTKNG

SED (Bayles, K. W. et al., J. Bacteriol. 171: 4799-4806 (1989))
                                                          [SEQ ID NO: 6]
  1 MKKFNILIAL LFFTSLVISP LNVKANENID SVKEKELHKK SELSSTALNN MKHSYADKNP

61 IIGENKSTGD QFLENTLLYK KFFTDLINFE DLLINFNSKE MAQHFKSKNV DVYPIRYSIN

121 CYGGEIDRTA CTYGGVTPHE GNKLKERKKI PINLWINGVQ KEVSLDKVQT DKKNVTVQEL
```

```
-continued
181 DAQARRYLQK DLKLYNNDTL GGKIQRGKIE FDSSDGSKVS YDLFDVKGDF PEKQLRIYSD

241 NKTLSTEHLH IDIYLYEK

SEE (Couch, J. L. et al., J. Bacteriol. 170: 2954-2960 (1988))
                                                        [SEQ ID NO: 7]
  1 MKKTAFILLL FIALTLTTSP LVNGSEKSEE INEKDLRKKS ELQRNALSNL RQIYYYNEKA

61 ITENKESDDQ FLENTLLFKG FFTGHPWYND LLVDLGSKDA TNKYKGKKVD LYGAYYGYQC

121 AGGTPNKTAC MYGGVTLHDN NRLTEEKKVP INLWIDGKQT TVPIDKVKTS KKEVTVQELD

181 LQARHYLHGK FGLYNSDSFG GKVQRGLIVF HSSEGSTVSY DLFDAQGQYP DTLLRIYRDN

241 KTINSENLHI DLYLYTT

TSST-1 (Prasad, G. S. et al., Protein Sci. 6: 1220-1227 (1997))
                                                        [SEQ ID NO: 8]
  1 MNKKLLMNFF IVSPLLLATT ATDFTPVPLS SNQIIKTAKA STNDNIKDLL DWYSSGSDTF

61 TNSEVLDNSL GSMRIKNTDG SISLIIFPSP YYSPAFTKGE KVDLNTKRTK KSQHTSEGTY

121 IHFQISGVTN TEKLPTPIEL PLKVKVHGKD SPLKYGPKFD KKQLAISTLD FEIRHQLTQI

181 HGLYRSSDKT GGYWKITMND GSTYQSDLSK KFEYNTEKPP INIDEIKTIE AEIN
```

The sections which follow discuss SAgs which have been discovered and characterized more recently.

Staphylococcal Enterotoxins SEG, SEH, SEI, SEJ, SEK, SEL, SEM, SEN, SEO, SEP, SEQ, SER, SEU Nucleic acids encoding Staphylococcal enterotoxins G, H, I, J, K, L and M (SEG, SEH, SEI, SEJ, SEK, SEL, SEM, SEN, SEO, SEP, SEQ, SER, SEU; abbreviated below as "SEG-SEU") were described in Jarraud, S. et al., *J. Immunol.* 166: 669-677 (2001); Jarraud S et al., *J. Clin. Microbiol.* 37: 2446-2449 (1999) and Munson, S H et al., *Infect. Immun.* 66:3337-3345 (1998); Omoe, K et al., ACCESSION BAC97795; Letertre, C et al *J. Appl. Microbiol.* 95, 38-43 (2003); Lindsay, J A et al., *Mol. Microbiol.* 29, 527-543 (1998); Kuroda, M. et al., *Lancet* 357, 1225-1240 (2001)). SEG-SEU show superantigenic activity and are capable of inducing tumoricidal effects. The homology of these SE's to the better known SE's in the family ranges from 27-64%. Each induces selective expansion of TCR Vβ subsets. Thus, these SEs retain the characteristics of T cell activation and vβ usage common to all the other SE's. RT-PCR was used to show that SEH stimulates human T cells via the vα domain of TCR, in particular vα (TRAV27), while no TCR VP-specific expansion was seen. This is in sharp contrast to all other studied bacterial superantigens, which are highly specific for TCR vβ. vβ binding superantigens form one group, whereas SEH has different properties that fit well with vα reactivity. It is suggested that SEH interacts directly with the TCR vα domain (Petersson K et al., *J Immunol.* 170:4148-54 (2003)). SEG and SEH of this group and other enterotoxins including SPEA, SPEC, SPEG, SPEH, SME-Z, SME-Z2, (see below) utilize zinc as part of high affinity MHC class II receptor. Amino acid substitution(s) at the high-affinity, zinc-dependent class II binding site are created to reduce their affinity for MHC class II molecules.

Egc Staphylococcal Enterotoxins

Jarraud S et al., 2001, supra, discloses methods used to identify and characterize egc SEs SEG-SEM, and for cloning and recombinant expression of these proteins. The egc comprises SEG, SEI, SEM, SEN, SEO and pseudogene products designated ψent 1 and ψent 2. Purified recombinant SEN, SEM, SEI, SEO, and SEGL29P (a mutant of SEN) were expressed in *E. coli*. Recombinant SEG, SEN, SEM, SEI, and SEO consistently induced selective expansion of distinct subpopulations of T cells expressing particular Vβ genes.

The yeast expression system is the preferred recombinant method for production of clinically useful egc SEs. Yeast is recognized as non pathogenic for human. By providing a secretion signal sequence, the egc SEs allows for secretion of substantial quantities of egc SEs into the culture media. This method allows the production of the superantigen in the yeast supernatant without the addition of any N- or C-terminus marker. The most prominent examples of yeast that can be used are *S. cerevisiae, Hansenula polymorpha, Pichia pastoris, Kluyveromyces lactis, Yarrowia lipolytica, Pichia methanolica, Pichia stipitis, Zygosaccharomyces rouxii* and *Z. bailii, Candida boidinii*, and *Schwanniomyces* (*Debaryomyces*) *occidentalis*. The methylotrophic yeast of the *Pichia* genus is used and methanol is employed as inducer of the alcohol oxidase (AOX 1) promoter in the expression systems. The enterotoxin-coding DNA sequence is cloned within an expression cassette containing a yeast promoter and transcriptional termination sequences.

cDNA of each egc SE is amplified by PCR using gene specific primers with overhangs generating NotI/EcoRI restriction sites at the 5' and 3' ends, respectively. A yeast secretion signal sequence is added to ensure full secretion of the enterotoxins into the culture supernatant. The primers are designed to ensure in-frame cloning of the cDNA of interest into the expression cassette. Therefore, sequences providing the restriction sites for cloning (NotI/EcoRI) are fused to gene specific sequences. Digested PCR products are inserted in-frame into the NotI/EcoRI restriction sites of the multiple cloning site. The expression vector pICZ A (Invitrogen) is prepared by sequential cutting with NotI and EcoRI, respectively. Ligation reactions and transformation into *E. coli* JM109 cells are carried out using standard methods.

Plasmid DNA of *E. coli* clones carrying an insert of the expected size is isolated linearized and transfected into via electroporation using a Bio-Rad GenePulser II. Settings are 1500 V, 50° F., and 200. Routinely, the alcohol oxidase 1 (AOX 1) promoter is employed for the expression of recombinant proteins. This promoter is tightly regulated and highly inducible by methanol, which also serves as the main carbon source during the expression. Using defined minimal media, *P. pastoris* can easily be grown to high cell densities. Thus, the cells are cultivated in WM9 medium without carbon source with 1% (v/v) methanol and 0.1% (w/v) glucose and incubated at 28° C. for 24 h. The supernatant from the cells is harvested. The egc SEs are then purified by at least two steps of High Pressure Liquid Chromatography. Each toxin purified separately will then be combined (likely in equimolar amounts) in order to produce the final preparation. Using the optimized feeding and induction protocol, we are now able to screen for and identify expression clones that produce heterologous protein with a yield of 2 mg per L culture volume or higher.

Egc SEs have been produced in *E. Coli* as follows: Primers were designed following identification of suitable hybridization sites in SEG, SEI, SEM, SEN, and SEO as given in Jarraud et al., (2001) supra. The 5' primers were chosen within the coding sequence of each gene, omitting the region predicted to encode the signal peptide, as determined by hydrophobicity analysis with GENEJOCKEY™ software and SIGNALP™ V1.11 World Wide Web Prediction Server (http://www.cbs.dtu.dk/services/SignalP/); the 3' primers were chosen to overlap the stop codon of each gene. A restriction site was included in each primer. DNA was extracted from A900322 or MJB1316 and used as a template for PCR amplification. PCR products and plasmid DNA were prepared using the Qiagen plasmid kit. PCR fragments were digested with EcoRI and Pst1 (Boehringer Mannheim) and ligated (T4 DNA ligase; Boehringer Mannheim) with the pMAL-c2 expression vector from New England Biolabs (Ozyme) digested with the same restriction enzymes. The resulting plasmids were transformed into *E. coli* TG1. The integrity of the ORF of each construct was verified by DNA sequencing of the junction between pMAL-c2 and the different inserts. The fusion proteins were purified from cell lysates of transfected *E. coli* by affinity chromatography on an amylose column according to the supplier's instructions (New England Biolabs).

Additional Methods for recombinant production of egc SE proteins, hosts, vectors and promoters and are given in *Recombinant Gene Expression Reviews and Protocols*, Second Edition, Eds: P Balbás, A. Lorence, Humana Press Inc. Totowa, N.J. (2004) which is herein incorporated by reference in its entirety.

Jarraud S et al., 2001, supra, indicates that the seven genes and pseudogenes composing the egc (enterotoxin gene cluster) operon are co-transcribed. The association of related co-transcribed genes suggested that the resulting peptides might have complementary effects on the host's immune response. One hypothesis is that gene recombination created new SE variants differing by their superantigen activity profiles. By contrast, SEGL29P failed to trigger expansion of any of 23 Vβ subsets, and the L29P mutation accounted for the complete loss of superantigen activity (although this mutation did not induce a major conformational change). It is believed that this substitution mutation located at a position crucial for proper superantigen/MHC II interaction.

Overall, TCR repertoire analysis confirms the superantigenic nature of SEG, SEI, SEM, SEN, SEO. These investigators used a number of TCR-specific mAbs (Vβ specificity indicated in brackets) for flow cytometric analysis: E2.2E7.2 (Vβ2), LE89 (Vβ3), IMMU157 (Vβ5.1), 3D11 (Vβ5.3), CRI304.3 (Vβ6.2), 3G5D15 (Vβ7), 56C5.2 (Vβ8.1/8.2), FIN9 (Vβ9), C21 (Vβi 1), S511 (Vβ2), IMMU1222 (Vβ13.1), JIJ74 (Vβ13.6), CAS1.1.13 (Vβ14), Tamayal.2 (Vβ16), E17.5F3 (Vβ17), 13A62.6 (Vβ18), ELL1.4 (Vβ20), IG125 (Vβ21.3), IMMU546 (Vβ22), and HUT78.1 (Vβ23). Flow cytometry also revealed preferential expansion of CD4+ T cells in SEI and SEM cultures. By contrast, the CD4/CD8 ratios in SEO-, SEN-, and SEG-stimulated T cell lines were close to those in fresh PBL.

A preferred method of producing recombinant egc SE's is to use the pET43™ vector (Novagen) and the *E. Coli* BL21DE3 strain (Invitrogen). Primers for each egc SE were prepared according to Jarraud et al., (*J. Immunol.* (2000) supra). To increase soluble expression of the egc SE's, each of them was inserted into the pET43.1a vector (Novagen) to produce a fusion protein with a NusA-tag (NusA protein) which facilitates protein folding, a His-tag for protein selection and isolation and an enterokinase and a thrombin cleavage sites for removal of the NusA-His-tag polypeptide. Each egc SE DNA was cloned into the SmaI and HindIII or XbaI/avrII sites of pET43.1™ (Novagen) which encodes Nus and 6×His tags at its $NH_2$ terminus and transformed in *Escherichia coli* BL21DE3 (Novagen) bacteria as 6His-NusA-fusion proteins. Cells are grown at 37° C. to A600 0.5-0.6, induced with 1 mM isopropyl-D-thiogalactoside for 4 h at 37° C. and in some cases is continued overnight at 15° C. Cells were lysed by lysozyme/sonication in lysis buffer (50 mM $NaH_2PO_4$, 300 mM NaCl, 10 mM imidazole, pH 8.0 and protease inhibitor cocktail tablets (ROCHE)), and insoluble cellular debris is cleared by centrifugation.

The cleared solutions are incubated with $Ni_2+$-nitrilotriacetic acid agarose beads (QIAGEN) at 4° C. for 2 h. After several washes (wash buffer 50 mM $NaH_2PO_4$, 300 mM NaCl, 20 mM Imidazole, pH 8.0), the recombinant proteins are eluted from the beads with elution buffer (50 mM $NaH_2PO_4$, 300 mM NaCl, 250 mM imidazole, pH 8.0). Fraction of elution are analyzed by SDS-PAGE, and fractions containing the NusA-Egc fusion proteins are pooled, and concentrated and dialyzed against PBS using Amicon Ultra-PL30 or PL-50 centrifugal filter devices (Millipore).

The NusA-tag is removed from the fusion protein by digestion with Thrombin protease (Amersham) in cleavage buffer (50 mM Tris HCl, 0.1 M NaCl, 0.25 mM $CaCl_2$, pH 8.5) for 18 h at 22° C. or for 18 h at 37° C., with or without previous heating at 95° C. for 10 minutes to improve access to cleavage site. The ratio of fusion protein to protease is optimized and set to 0.2 unit/mg protein. The thrombin-treated solution is loaded directly onto an anion exchange chromatography on HITRAP Q™ HP column (Amersham) equilibrated with buffer A (50 mM Tris HCl, pH8.5). The protein was eluted through a 0-50% gradient of buffer B (50 mM Tris HCl, 1 M NaCl, pH8.5. Fraction of elution were analyzed by SDS-PAGE, and fractions containing cleaved egc SE's are pooled and further purified by gel filtration through a HILOAD™16/60 Superdex 200 prep grade column (Amersham). The final protein concentrations were measured by UV spectrophotometry.

With this method, each egc SE showed mitogenicity in a T cell proliferation assay using a CD69-specific cytofluorimetric assay measuring T-cell activation (Lina G et al., *J. Clin. Micro.* 36:1042-1045 (1998)). The Vβ profile of the egc SEs prepared in this fashion matched that of purified recombinant egc SE's using the plasmid pMAL-c2 vector in *E. Coli* strain TG1.

pET (T7 promoter system) vectors without tags and with the kanamycin resistance marker (either pET9 or 28) or others are feasible for use in this system as well as are vectors with pelB leading sequence. The *E. coli* BL21(DE3)AI is also a feasible host for expressions.

Additional recombinant and biochemical preparations of the egc SEs are given U.S. provisional application Ser. No. 61/462,622 filed Feb. 3, 2011 and U.S. 60/799,514, PCTUS05/022,638, U.S. 60/583,692, U.S. 60/665,654, U.S. 60/626,159 all of which are incorporated by reference and their references in their entirety.

Our most current methodology for manufacture of SEG and SEG$_{leu}$47$_{arg}$ yielding up to 300 mg of egc-SE's and SEG$_{leu}$47$_{arg}$ homologue with 98% purity is given as follows. The prokaryotic expression cassette for the SEG was codon optimized and built synthetically and the gene was cloned into the pET24b( -continued SEI (Kuroda, M. et al., Lancet 357 (9264), 1225-1240 (2001))
[SEQ ID NO: 12]
```
  1 MKKFKYSFIL VFILLFNIKD LTYAQGDIGV GNLRNFYTKH DYIDLKGVTD KNLPIANQLE
 61 FSTGTNDLIS ESNNWDEISK FKGKKLDIFG IDYNGPCKSK YMYGGATLSG QYLNSARKIP
121 INLWVNGKHK TISTDKIATN KKLVTAQEID VKLRRYLQEE YNIYGHNNTG KGKEYGYKSK
181 FYSGFNNGKV LFHLNNEKSF SYDLFYTGDG LPVSFLKIYE DNKIIESEKF HLDVEISYVD
241 SN
```

SEJ (Zhang, S. et al., FEMS Microbiol. Lett. 168: 227-233 (1998))
[SEQ ID NO: 13]
```
  1 MKKTIFILIF SLTLTLLITP LVYSDSKNET IKEKNLHKKS ELSSITLNNL RHIYFFNEKG
 61 ISEKIMTEDQ FLDYTLLFKS FFISHSQYND LLVQFDSKET VNKFKGKQVD LYGSYYGFQC
121 SGGKPNKTAC MYGGVTLHEN NQLYDTKKIP INLWIDSIRT VVPLDIVKTN KKKVTIQELD
181 LQARYYLHKQ YNLYNPSTFD GKIQKGLIVF HTSKEPLVSY DLFNVIGQYP DKLLKIYQDN
241 KIIESENMHI DIYLYTSLIV LISLPLVL
```

SEK (Baba, T., et al., Lancet 359: 1819-1827 (2002))
[SEQ ID NO: 14]
```
  1 MKKLISILLI NIIILGVSNN ASAQGDIGID NLRNFYTKKD FINLKDVKDN DTPIANQLQF
 61 SNESYDLISE SKDFNKFSNF KGKKLDVFGI SYNGQCNTKY IYGGITATNE YLDKPRNIPI
121 NIWINGNHKT ISTNKVSTNK KFVTAQEIDI KLRRYLQEEY NIYGHNGTKK GEEYGHKSKF
181 YSGFNIGKVT FHLNNNDTFS YDLFYTGDDG LPKSFLKIYE DNKTVESEKF HLDVDISYKE
241 TK
```

SEL (Kuroda, M. et al., Lancet 357: 1225-1240 (2001))
[SEQ ID NO: 15]
```
  1 MKKRLLFVIV ITLFIFSSNH TVLSNGDVGP GNLRNFYTKY EYVNLKNVKD KNSPESHRLE
 61 YSYKNDTLYA EFDNEYITSD LKGKNVDVFG ISYKYGSNSR TIYGGVTKAE NNKLDSPRII
121 PINLIINGKH QTVTTKSVST DKKMVTAQEI DVKLRKYLQD EFNIYGHNDT GKGKEYGTSS
181 KFYSGFDKGS VVFHMNDGSN FSYDLFYTGY GLPESFLKIY KDNKTVDSTQ FHLDVEISKR
```

SEM (Kuroda, M. et al., Lancet 357: 1225-1240 (2001))
[SEQ ID NO: 16]
```
  1 MKRILIIVVL LFCYSQNHIA TADVGVLNLR NYYGSYPIED HQSINPENNH LSHQLVFSMD
 61 NSTVTAEFKN VDDVKKFKNH AVDVYGLSYS GYCLKNKYIY GGVTLAGDYL EKSRRIPINL
121 WVNGEHQTIS TDKVSTNKKL VTAQEIDTKL RRYLQEEYNI YGFNDTNKGR NYGNKSKFSS
181 GFNAGKILFH LNDGSSFSYD LFDTGTGQAE SFLKIYNDNK TVETEKFHLD VEISYKDES
```

SEN (Jarraud, S et al., J. Immunol. 166: 669-677 (2001))
(SEQ ID NO: 17)
```
  1 MKNSKVMLNV LLILNLIAI CSVNNAYANE EDPKIESLCK KSSVGPIALH NINDDYINNR
 61 RFTTVKSIVS TTEKFLDFDL LFKSINWLDG ISAEFKDLKE FSSSAISKEF LGKYVDIYGV
121 YYKAHCGEH QVDTACTYGG VTPHENNKLS EPKNIGVAVY KDNVNVNVNT FIVTTDKKK
181 VYAQELDIKV RTKLNNAYKL YDRMTSDVQK GYIKFHSHSE HKESFYYDLF YIKGNLPDQY
241 LQIYNDNKTT IDSSDYHIDV YLFT
```

SEO (Jarraud, S et al., J. Immunol. 166: 669-677 (2001))
(SEQ ID NO: 18)
```
  1 MKNIKKLMRL FYIAAIIITL LCLINNNYVN AEVDKKDLKK KSDLDSSKLFN LTSYYTDITW
 61 QLDESNKIST DQLNNYIILK NIDISVLKTS SLKVEFNSSD LANQFKGKNUD IYGLYFGNKC
121 VGLTEEKTSC LYGGVTIHDG NQLDEEKVIG VNGFKDGVQQ EGFVIKTKKAK VTVQELDTKV
181 RFKLENLYKI YNKDTGNIQK GCIFFHSHNH QDQSFYYDLY NVKGSVGAEFF QFYSDNRTVS
241 SSNYHIDVFL YKD
```

-continued

ψent 1 (Jarraud, S et al., J. Immunol. 166: 669-677 (2001))
(SEQ ID NO: 19)
```
  1 MKLFAFIFIC VKSCSLLFML NGNPKPEQLN KASEFTGLMD NMRYLYDDKH VSETNIKSQE

61 KFLQHDLLFK INGSKILKTE FNNKSLSDKY KNKNVDLFGT NYYNQCYFSL DNMELNDGRL

121 IEKNVYVWRC GL
```

ψent 2 (Jarraud, S et al., J. Immunol. 166: 669-677 (2001))
(SEQ ID NO: 20)
```
  1 MYGGVVYENE RNSLSFDIPT NKKNITAQEI DYKVRNYLLK HKNLYEFNSSP YETGYIKFIE

61 GSGHSFWYDL MPESGKKFYP TKYLLIYNDN KTVESKSINV EVHLTKK
```

SEP (Kuroda, M. et al., Lancet 357, 1225-1240 (2001))
[SEQ ID NO: 21]
```
  1 MSKMKKTAFT LLLFIALTLT TSPLVNGSEK SEEINEKDLR KKSELQGTAL GNLKQIYYN

61 EKAKTENKES HDQFLQHTIL FKGFFTDHSW YNDLLVDFDS KDIVDKYKGK KVDLYFAYYG

121 YQCAGGTPNK TACMYGGVTL HDNNRLTEEK KEPINLWLDG KQNTVPLETV KTNKKVTVQ

181 ELDLQARRYL QEKYNLYNSD VFDGKVQRGL IVFHTSTEPS VNYDLFGAQG QYSNTLLRIY

241 RDNKTINSEN MHIDIYLYTS
```

SEQ (Lindsay, JA et al., Mol. Microbiol. 29, 527-543 (1998))
[SEQ ID NO: 22]
```
  1 MPIWRCNIKK GAIKMNKIFR ILTVSLFFFT FLIKNNLAYA DVGVINLRNF YANYEPEKLQ

61 GVSSGNFSTS HQLEYIDGKY TLYSQFHNEY EAKRLKDHKV DIFGISYSGL CNTKYMGGI

121 TLANQNLDKP RNIPINLWVN GKQNTISTDK VSTQKKEVTA QEIDIKLRKY LQNEYNIYGF

181 NKTKKGGEYG YQSKFNSGFN KGKITFHLNN EPSFTYDLFY TGTGGAESFL KIYNDNKTID

241 AENFHLDVEI SYEKTE
```

SER Omoe, K et al., ACCESSION BAC97795
[SEQ ID NO: 23]
```
  1 MLNKILLLLF SVTFMLLFFS LHSVSAKPDP RPGELNRVSD YKKNKGTMGN VESLYKDKAV

61 IAENVKNTRQ FLGHDLIFPI PYSEYKEVKS EFINKKTADK FKDKRLDVFG IPYFYTCLVP

121 KNESREEFIF DGVCIYGGVT MHSTADSISK NIIVPVTVDN KQQFSFTIST NKKTVTVQEL

181 DYKVRNWLTN NKKLYEFDGS AYETGYIKFI EQNKDSFWYD LFPKKDLVPF IPYKFVNIYG

241 DNKTIDASSV KIEVHLTTM
```

SEU (Letertre, C et at J. Appl. Microbiol. 95, 38-43 (2003))
[SEQ ID NO: 24]
```
  1 MKLFAFIFIC VKSCSLLFML NGNPRPEQLN KASEFSGLMD NMRYLYDDKH VSETNIKAQE

61 KFLQHDLLFK INGSKIDGSK ILKTEFNNKS LSDKYKNKNV DLFGTNYYNQ CYFSADNMEL

121 NDGRLIEKTC MYGGVTEHDG NQIDKNNLTD NSHNILIKVY ENERNTLSFD ISTNMKNITA

181 QEIDYKVRNY LLKHKNLYEF NSSPYESGYI KFIEGNGHSF WYDMMPESGE KFYPTKYLLI

241 YNDNKTVESK SINVEVHLTK K
```

Streptococcal Pyrogenic Exotoxins (SpEs)

The SpE's SPEA, SPEB, SPEC, SPEG, SPEH, SME-Z, SME-Z2 and SSA are superantigens induce tumoricidal effects. SPEA, SPEB, SPEC have been known for some time and their structures and biological activities described in numerous publications.

SPEG, SPEH, and SPEJ genes were identified from the *Streptococcus pyogenes* M1 genomic database and described in detail in Proft, T et al., *J. Exp. Med.* 189: 89-101 (1999) which also describes SMEZ, SMEZ-2. This document also describes the cloning and expression of the genes encoding these proteins.

The smez-2 gene was isolated from the *S. pyogenes* strain 2035, based on sequence homology to the streptococcal mitogenic exotoxin z (smez) gene. SMEZ-2, SPE-G, and SPE-J are most closely related to SMEZ and SPEC, whereas SPEH is most similar to the SEs than to any other streptococcal toxin.

As described by Proft, T et al supra, rSMEZ, rSMEZ-2, rSPE-G, and rSPE-H were mitogenic for human peripheral blood T lymphocytes. SMEZ-2 appears to be the most potent SAg discovered thus far.

All these toxins, except rSPE-G, were active on murine T cells, but with reduced potency.

Binding to a human B-lymphoblastoid line was shown to be zinc dependent with high binding affinity of 15-65 nM. Analysis of competition for binding between toxins of this group revealed overlapping but discrete binding to subsets of class II molecules in the hierarchical order (SMEZ, SPE-C)>SMEZ-2>SPE-H>SPE-G. The most common targets for these SAgs were human Vβ2.1- and Vβ4-expressing T cells.

*Streptococcus* Pyrogenic Exotoxin A (SPEA)

SPEA can be purified from cultures of *S. pyogenes* as described by Kline et al., *Infect. Immun.* 64:861-869 (1996). Plasmids that include the spea1 gene which encode SPEA, and the expression and purification of recombinant SPEA ("rSPEA") are described by Kline et al., supra. The native SPEA sequence is shown below:

```
SPEA (Papageorgiou, A. C. et al. EMBO J. 18: 9-21 (1999))
                                                            [SEQ ID NO: 25]
  1 MENNKKVLKK MVFFVLVTFL GLTISQEVFA QQDPDPSQLH RSSLVKNLQN IYFLYEGDPV

61 THENVKSVDQ LLSHDLIYNV SGPNYDKLKT ELKNQEMATL FKDKNVDIYG VEYYHLCYLC

121 ENAERSACIY GGVTNHEGNH LEIPKKIVVK VSIDGIQSLS FDIETNKKMV TAQELDYKVR

181 KYLTDNKQLY TNGPSKYETG YIKFIPKNKE SFWFDFFPEP EFTQSKYLMI YKDNETLDSN

241 TSQIEVYLTT K
```

*Streptococcus* Pyrogenic Exotoxin B (SPEB)

Purification of native SPEB is described by Gubba, S. et al., *Infect. Immun.* 66: 765-770 (1998). Expression and purification of recombinant SPEB are also described in this reference. The native SPEB sequence is shown below (Kapur, V. et al., *Microb. Pathog.* 15:327-346 (1993)): [SEQ ID NO:17]

```
                                                            [SEQ ID NO: 17]
  1 MNKKKLGIRL LSLLALGGFV LANPVFADQN FARNEKEAKD SAITFIQKSA AIKAGARSAE

61 DIKLDKVNLG GELSGSNMYV YNISTGGFVI VSGDKRSPEI LGYSTSGSFD ANGKENIASF

121 MESYVEQIKE NKKLDTTYAG TAEIKQPVVK SLLDSKGIHY NQGNPYNLLT PVIEKVKPGE

181 QSFVGQHAAT GCVATATAQI MKYHNYPNKG LKDYTYTLSS NNPYFNHPKN LFAAISTRQY

241 NWNNILPTYS GRESNVQKMA ISELMADVGI SVDMDYGPSS GSAGSSRVQR ALKENFGYNQ

301 SVHQINRSDF SKQDWEAQID KELSQNQPVY YQGVGKVGGH AFVIDGADGR NFYHVNWGWG

361 GVSDGFFRLD ALNPSALGTG GGAGGFNGYQ SAVVGIKP
```

*Streptococcus* Pyrogenic Exotoxin C (SPEC)

Methods of isolation and characterization of SPEC is carried out by the methods of Li, P L et al., *J. Exp. Med.* 186: 375-383 (1997). These references also describe T cell proliferation stimulated by this SAg and the analysis of its selectivity for TCR Vβ regions. The native sequence of SPEC (Kapur, V. et al., *Infect. Immun.* 60: 3513-3517 (1992)) is shown below: [SEQ ID NO:18]

*Streptococcus* Pyrogenic Exotoxin C (SPEC)

```
                                                            [SEQ ID NO: 18]
  1 MKKINIIKIV FIITVILIST ISPIIKSDSK KDISNVKSDL LYAYTITPYD YKDCRVNFST

61 THTLNIDTQK YRGKDYYISS EMSYEASQKF KRDDHVDVFG LFYILNSHTG EYIYGGITPA

121 QNNKVNHKLL GNLFISGESQ QNLNNKIILE KDIVTFQEID FKIRKYLMDN YKIYDATSPY

181 VSGRIEIGTK DGKHEQIDLF DSPNEGTRSD IFAKYKDNRI INMKNFSHFD IYLE
```

Streptococcal Superantigen (SSA)

SSA is an ~28-kDa superantigen protein isolated from culture supernatants as described by Mollick J et al., *J. Clin. Invest.* 92: 710-719 (1993) and Reda K et al., *Infect. Immun.* 62: 1867-1874 (1994). SSA stimulates proliferation of human T cells bearing Vβ1, Vβ3, Vβ5.2, and Vβ15 in an MHC class II-dependent manner. The first 24 amino acid residues of SSA are 62.5% identical to SEB, SEC1, and SEC3. Purification and cloning of SSA is described in Reda K et al., *Infect. Immun.* 62: 1867-1874 (1994). The native sequence of SSA (Reda, K. B. et al., *Infect. Immun.* 64: 1161-1165 (1996)) is shown below: [SEQ ID NO:19]

```
                                                            [SEQ ID NO: 19]
  1 MNKRIRILVV ACVVFCAQLL SISVFASSQP DPTPEQLNKS SQFTGVMGNL RCLYDNHFVE

61 GTNVRSTGQL LQHDLIFPIK DLKLKNYDSV KTEFNSKDLA AKYKNKDVDI FGSNYYYNCY

121 YSEGNSCKNA KKTCMYGGVT EHHRNQIEGK FPNITVKVYE DNENILSFDI TTNKKQVTVQ

181 ELDCKTRKIL VSRKNLYEFN NSPYETGYIK FIESSGDSFW YDMMPAPGAI FDQSKYLMLY

241 NDNKTVSSSA IAIEVHLTKK
```

Streptococcal Pyrogenic Exotoxins G and H and SMEZ

The sequences of the more recently discovered Streptococcal exotoxin SAgs are provided below:

SPEG (Fraser, J et al., Mol Med Today 6: 125-32 (2000))

```
                                                            [SEQ ID NO: 29]
  1 DENLKDLKRS LRFAYNITPC DYENVEIAFV TTNSIHINTK QKRSECILYV DSIVSLGITD

61 QFIKGDKVDV FGLPYNFSPP YVDNIYGGIV KHSNQGNKSL QFVGILNQDG KETYLPSEVV

121 RIKKKQFTLQ EFDFKIRKFL MEKYNIYDSE SRYTSGSLFL ATKDSKHYEV DLFNKDDKLL

181 SRDSFFKRYK DNKIFNSEEI SHFDIYLKTY
```

SPEH (Proft, T. et al., J. Exp. Med. 189: 89-102 (1999))

```
                                                            [SEQ ID NO: 30]
  1 MRYNCRYSHI DKKIYSMIIC LSFLLYSNVV QANSYNTTNR HNLESLYKHD SNLIEADSIK

61 NSPDIVTSHM LKYSVKDKNL SVFFEKDWIS QEFKDKEVDI YALSAQEVCE CPGKRYEAFG

121 GITLTNSEKK EIKVPVNVWD KSKQQPPMFI TVNKPKVTAQ EVDIKVRKLL IKKYDIYNNR

181 EQKYSKGTVT LDLNSGKDIV FDLYYFGNGD FNSMLKIYSN NERIDSTQFH VDVSIS
```

SMEZ (Proft, T. et al., J. Exp. Med. 191: 1765-1776 (2000))

```
                                                            [SEQ ID NO: 31]
  1 LEVDNNSLLR NIYSTIVYEY SDTVIDFKTS HNLVTKKLDV RDARDFFINS EMDEYAANDF

61 KAGDKIAVFS VPFDWNYLSK GKVTAYTYGG ITPYQKTSIP KNIPVNLWIN RKQIPVPYNQ

121 ISTNKTTVTA QEIDLKVRKF LIAQHQLYSS GSSYKSGKLV FHTNDNSDKY SLDLFYTGYR

181 DKESIFKVYK DNKSFNIDKI GHLDIEIDS
```

SMEZ 2 (Arcus, V. L. et al., J. Mol. Biol. 299 (1), 157-168 (2000))

```
                                                            [SEQ ID NO: 32]
  1 GLEVDNNSLL RNIYSTIVYE YSDIVIDFKT SHNLVTKKLD VRDARDFFIN SEMDEYAAND

61 FKTGDKIAVF SVPFDWNYLS KGKVTAYTYG GITPYQKTSI PKNIPVNLWI NGKQISVPYN

121 EISTNKTTVT AQEIDLKVRK FLIAQHQLS SGSSYKSGRL VFHTNDNSDK YSFDLFYVGY

181 RDKESIFKNY KDNKSFNIDK IGHLDIEIDS
```

*Yersinia pseudotuberculosis* Mitogen (Superantigen) (YPM)

Cloning, expression and purification of YPM is described by Miyoshi-Akiyama, T. et al., *J. Immunol.* 154: 5228-5234 (1995).

The above reference described assays of YPM using lymphoid cells and murine L cells transfected with human HLA genes, including T cell proliferation and cytokine (IL2) secretion. The sequence of YPM is shown below

```
(Carnoy, C. et al., J. Bacteriol. 184 (16), 4489-4499 (2002))
                                                     [SEQ ID NO: 33]:
  1 MKKKFLSLLT LTFFSGLALA ADYDNTLNSI PSLRIPNIET YTGTIQGKGE VCIRGNKEGK

61 SRGGELYAVL RSTNANADMT LILLCSIRDG WKEVKRSDID RPLRYEDYYT PGALSWIWEI

121 KNNSSEASDY SLSATVHDDK EDSDVLMKCP
```

Staphylococcal Exotoxin Like Proteins (SET)

The identification characterization of the SETs (SET-1 and SET-2) and the cloning and purification of SET-1 is described in Williams, R. J. et al., *Infect. Immun.* 68: 4407-4414 (2000). This reference discloses the distribution of the set1 gene among Staphylococcal species and strains.

The set1 nucleotide sequences are deposited in the GenBank database under accession numbers AF094826 (set gene cluster fragment), AF188835 (NCTC 6571 set1 gene), AF188836 (FRI326 set1 gene), and AF188837 (NCTC 8325-4 set1 gene). Recombinant SET-1 protein stimulates production of the proinflammatory cytokines IL-1β, IL-6, and TNFα

```
SET1 (Williams, R. J. et al., Infect. Immun. 68 (8), 4407-4415 (2000))
                                                          [SEQ ID NO: 34]
  1 MKLKTLAKAT LALSLLTTGV ITLESQAVKA AEKQERVQHL YDIKDLYRYY SAPSFEYSNI

61 SGKVENYNGS NVVRFNQKDQ NHQLFLLGKD KEQYKEGLQG KDVFVVQELI DPNGRLSTVG

121 GVTKKNNKTS ETKTHLLVNK VDGGNLDASI DSFLIQKEEI SLKELDFKIR QQLVEKYGLY

181 QGTSKYGKIT INLKDEKREV IDLSDKLEFE RMGDVLNSKD IKGISVTINQ I

SET2 Williams, R. J., et al., Infect. Immun. 68 (8), 4407-4415 (2000)
                                                          [SEQ ID NO: 35]
  1 MKLKTLAKAT LALGLLTTGV ITSEGQAVQA AEKQERVQHL HDIRDLHRYY SSESFEYSNV

61 SGKVENYNGS NVVRFNPKDQ NHQLFLLGKD KEQYKEGLQG QNVFVVQELI DPNGRLSTVG

121 GVTKKNNKTS ETNTPLFVNK VNGEDLDASI DSFLIQKEEI SLKELDFKIR QQLVNNYGLY

181 KGTSKYGKII INLKDENKVE IDLGDKLQFE RMGDVLNSKD IRGISVTINQ I

SET3 (Williams, R. J. et al., Infect. Immun. 68 (8), 4407-4415 (2000))
                                                          [SEQ ID NO: 36]
  1 MKMTAIAKAS LALSILATGV ITSTAQTVNA SEHESKYENV TJDUFDKRDT YSRASKELKN

61 VTGYRSKGG KKHYLIFDKNR KFTRIQIFGK DIERIKKRKN PGLDIFVVKE AENRNGTVYS

121 YGGVTLLMQG AYYDYLSAPR FVIKKEVGAG VSVHVKRYYI YKEEISLKEL DFKLRQYLIQ

181 DFDLYKKFPK ASKIKVTMKD GGYYTFELNK KLQTNRMSDV IDGRNIEKIE ANIR

SET4 (Williams, R. J. et al., Infect. Immun. 68 (8), 4407-4415 (2000))
                                                          [SEQ ID NO: 37]
  1 MKLTALAKVT LALGILTTGT LTTEAHSGHA KQNQKSVNKH DKEALHRYYT GNFKEMKNIN

61 ALRHGKNNLR FKYRGMKTQV LLPBDEYRKY QQRRHTGLDV FFNQERRDKH DISYTVGGVT

121 KTNKTSGFVS TPRLNVTKEK GEDAFVKGYP YDIKKEEISL KELDFKLRKH LIEKYGLYKT

181 LSKDGRIKIS LKDGSFYNLD LRTKLKFKHM GEVIDSKQIK DIEVNLK

SET5 (Williams, R. J., et al., Infect. Immun. 68 (8), 4407-4415 (2000))
                                                          [SEQ ID NO: 38]
  1 MKLTAIAKAT LALGILTTGV MTAESQTVNA KVKLDETQRK YYINMLKDYY SQESYESTNI

61 SVKSEDYYGS NVLNFNQRNK NFKVFLIGDD RNKYKELTHG RDVFAVPELI DTKGGIYSVG

121 GITKKNVRSV FGYVSHPGLQ VKKVDPKDGF SIKELFFIQK EEVSLKELDF KIRKMLVEKY

181 RLYKGASDKG RIVINMKDEK KHEIDLSEKL SFDRMFDVLD SKQIKNIEVN LN
```

Functional Homologues and Derivatives of Superantigen Proteins or Peptides

The present invention contemplates, in addition to native SAgs, the use of homologues of native SAgs that have the requisite biological activity to be useful in accordance with the invention. This biological activity consists of T cell mitogenicity and T cell TCR Vβ specificity of the mitogenicity. Constructs 1-4 compositions described herein are in nucleic acid form. However, for purposes of identifying a homologue of a SAg, the candidate molecule's corresponding amino acid sequence or nucleic acid is compared to the closest wild type SE as described below. The preferred method of establishing structural homology is FASTA. A molecule showing a z value>13 versus the wild type SE is considered to have structural homology to the wild type SE.

Thus, in addition to native egc SAg protein and nucleic acid compositions described herein, the present invention encompasses functional derivatives, among which homologues are preferred. Homologues of the egc SEs are preferred. However, biologically active homologues of other staphylococcal enterotoxins, streptococcal exotoxins. *Y. pseudotuberculosis* superantigen YPM, *C. perfringens* toxin A, *M. arthritides* superantigens are included if humans do not have preexistent neutralizing antibodies against them. By "functional derivative" is meant a "fragment," "variant," "mutant," "homologue," "analogue," or "chemical derivative. Homologues include fusion proteins, chimeric proteins and conjugates that include a SAg portion fused to or conjugated to a fusion partner polypeptide or peptide. A functional derivative retains at least a portion of the biological activity of the native protein which permits its utility in accordance with the present invention. Such biological activity includes stimulation of T cell proliferation and/or cytokine secretion, stimulation of T cell-mediated cytotoxic activity, as a result of interactions of the SAg composition with T cells preferably via the TCR Vβ or Vα region.

A "fragment" refers to any shorter peptide. A "variant" refers to a molecule substantially similar to either the entire protein or a peptide fragment thereof. Variant peptides may be conveniently prepared by direct chemical synthesis of the variant peptide, using methods well-known in the art.

A homologue refers to a natural protein, encoded by a DNA molecule from the same or a different species. Homologues, as used herein, typically share at least about 50% sequence similarity at the DNA level or at least about 18% sequence similarity at the amino acid level, with a native protein.

An "analogue" refers to a non-natural molecule substantially similar to either the entire molecule or a fragment thereof A "chemical derivative" contains additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues.

A fusion protein comprises a native SAg, a fragment or a homologue fused by recombinant means to another polypeptide fusion partner, optionally including a spacer between the two sequences. Preferred fusion partners are antibodies, Fab fragments, single chain Fv fragments. Other fusion partners are any peptidic receptor ligand, cytokine, extracellular domain ("ECD") of a costimulatory molecule and the like.

The recognition that the biologically active regions of the SEs, for example, are substantially homologous, i.e., that the sequences are substantially similar, enables prediction of the sequences of synthetic peptides which will exhibit similar biological effects in accordance with this invention (Johnson, L. P. et al., *Mol. Gen. Genet.* 203:354-356 (1986).

The following terms are used in the disclosure of sequences and sequence relationships between two or more nucleic acids or polypeptides: (a) "reference sequence", (b) "comparison window", (c) "sequence identity", (d) "percentage of sequence identity", and (e) "substantial identity"

As used herein, "reference sequence" is a defined sequence used as a basis for sequence comparison. A reference sequence may be a subset or the entirety of a specified sequence; for example, as a segment of a full-length cDNA or other polynucleotide sequence, or the complete cDNA or polynucleotide sequence. The same is the case for polypeptides and their amino acid sequences.

As used herein, "comparison window" includes reference to a contiguous and specified segment of a polynucleotide or amino acid sequence, wherein the sequence may be compared to a reference sequence and wherein the portion of the sequence in the comparison window may comprise additions or deletions (i.e., gaps) compared to the reference sequence (which does not comprise additions or deletions) for optimal alignment of the two sequences. Generally, the comparison window is at least 20 contiguous nucleotides or amino acids in length, and optionally can be 30, 40, 50, 100, or longer. Those of skill in the art understand that to avoid a high similarity to a reference sequence due to inclusion of gaps in the sequence a gap penalty is typically introduced and is subtracted from the number of matches.

Methods of alignment of nucleotide and amino acid sequences for comparison are well-known in the art. For comparison, optimal alignment of sequences may be done using any suitable algorithm, of which the following are examples:

(a) the local homology algorithm ("Best Fit") of Smith and Waterman, *Adv. Appl. Math.* 2: 482 (1981);

(b) the homology alignment algorithm (GAP) of Needleman and Wunsch, *J. Mol. Biol.* 48: 443 (1970); or (c) a search for similarity method (FASTA and TFASTA) of Pearson and Lipman, *Proc. Natl. Acad. Sci.* 85 2444 (1988);

In a preferred method of alignment, Cys residues are aligned. Computerized implementations of these algorithms, include, but are not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG) (Madison, Wis.). The CLUSTAL program is described by Higgins et al., *Gene* 73:237-244 (1988); Higgins et al., *CABIOS* 5:151-153 (1989); Corpet et al., *Nuc Acids Res* 16:881-90 (1988); Huang et al., *CABIOS* 8:155-65 (1992), and Pearson et al., *Methods in Molecular Biology* 24:307-331 (1994).

A preferred program for optimal global alignment of multiple sequences is PileUp (Feng and Doolittle, *J Mol Evol* 25:351-360 (1987) which is similar to the method described by Higgins et al. 1989, supra).

The BLAST family of programs which can be used for database similarity searches includes: NBLAST for nucleotide query sequences against database nucleotide sequences; XBLAST for nucleotide query sequences against database protein sequences; BLASTP for protein query sequences against database protein sequences; TBLASTN for protein query sequences against database nucleotide sequences; and TBLASTX for nucleotide query sequences against database nucleotide sequences. See, for example, Ausubel et al., eds., *Current Protocols in Molecular Biology*, Chapter 19, Greene Publishing and Wiley-Interscience, New York (1995) or most recent edition. Unless otherwise stated, stated sequence identity/similarity values provided herein, typically in percentages, are derived using the BLAST 2.0 suite of programs (or updates thereof) using default parameters. Altschul et al., *Nuc Acids Res*. 25:3389-3402 (1997).

As is known in the art, BLAST searches assume that proteins can be modeled as random sequences. However, many real proteins comprise regions of nonrandom sequence which may include homopolymeric tracts, short-period repeats, or regions rich in particular amino acids. Alignment of such regions of "low-complexity" regions between unrelated proteins may be performed even though other regions are entirely dissimilar. A number of low-complexity filter programs are known that reduce such low-complexity alignments. For example, the SEG (Wooten et al., *Comput. Chem.* 17:149-163 (1993)) and XNU (Claverie et al., *Comput. Chem,* 17:191-201 (1993)) low-complexity filters can be employed alone or in combination.

As used herein, "sequence identity" or "identity" in the context of two nucleic acid or amino acid sequences refers to the residues in the two sequences which are the same when aligned for maximum correspondence over a specified comparison window. It is recognized that when using percentages of sequence identity for proteins, a residue position which is not identical often differs by a conservative amino acid substitution, where a substituting residue has similar chemical properties (e.g., charge, hydrophobicity, etc.) and therefore does not change the functional properties of the polypeptide. Where sequences differ in conservative substitutions, the % sequence identity may be adjusted upwards to correct for the conservative nature of the substitution, and be expressed as "sequence similarity" or "similarity" (combination of identity and differences that are conservative substitutions). Means for making this adjustment are well-known in the art. Typically this involves scoring a conservative substitution as a partial rather than as a full mismatch, thereby increasing the percentage sequence identity. Thus, for example, where an identical amino acid is given a score of "1" and a non-conservative substitution is given a score of "0" zero, a conservative substitution is given a score between 0 and 1. The scoring of conservative substitutions is calculated, e.g., according to the algorithm of Meyers et al., *CABIOS* 4:11-17 (1988) as implemented in the program PC/GENE (Intelligenetics, Mountain View, Calif., USA).

As used herein, "percentage of sequence identity" refers to a value determined by comparing two optimally aligned sequences over a comparison window, wherein the portion of the nucleotide or amino acid sequence in the comparison window may comprise additions or deletions (i.e., gaps) as compared to the reference sequence (which lacks such additions or deletions) for optimal alignment, such as by the GAP algorithm (supra). The percentage is calculated by determining the number of positions at which the identical nucleotide or amino acid residue occurs in both sequences to yield the number of matched positions, dividing that number by the total number of positions in the window of comparison and multiplying the result by 100, thereby calculating the percentage of sequence identity.

The term "substantial identity" of two sequences means that a polynucleotide or polypeptide comprises a sequence that has at least 60%, preferably at least 70%, more preferably at least 80%, even more preferably at least 90%, and most preferably at least 95% sequence identity to a reference sequence using one of the alignment programs described herein using standard parameters. Values can be appropriately adjusted to determine corresponding identity of the proteins encoded by two nucleotide sequences by taking into account codon degeneracy, amino acid similarity, reading frame positioning, etc.

One indication that two nucleotide sequences are substantially identical is if they hybridize to one other under stringent conditions. Because of the degeneracy of the genetic code, a number of different nucleotide codons may encode the same amino acid. Hence, two given DNA sequences could encode the same polypeptide but not hybridize under stringent conditions. Another indication that two nucleic acid sequences are substantially identical is that the polypeptide encoded by the first nucleic acid is immunologically cross reactive with the polypeptide encoded by the second nucleic acid. Clearly, then, two peptide or polypeptide sequences are substantially identical if one is immunologically reactive with antibodies raised against the other. A first peptide is substantially identical to a second peptide, if they differ only by a conservative substitution. Peptides which are "substantially similar" share sequences as noted above except that nonidentical residue positions may differ by conservative substitutions.

Thus, in one embodiment of the present invention, the Lipman-Pearson FASTA or FASTP program packages (Pearson, W. R. et. al., 1988, supra; Lipman, D. J. et al, *Science* 227:1435-1441 (1985)) in any of its older or newer iterations may be used to determine sequence identity or homology of a given protein, preferably using the BLOSUM 50 or PAM 250 scoring matrix, gap penalties of −12 and −2 and the PIR or SwissPROT databases for comparison and analysis purposes. The results are expressed as z values or E ( ) values. To achieve a more "updated" z value cutoff for statistical significance, preferably corresponding to a z value >10 based on the increase in database size over that of 1988, in a FASTA analysis using the equivalent 2001 database, a significant z value would exceed 13.

A more widely used and preferred methodology determines the percent identity of two amino acid sequences or of two nucleic acid sequences after optimal alignment as discussed above, e.g., using BLAST. In a preferred embodiment of this approach, a polypeptide being analyzed for its homology with native SAg is at least 20%, preferably at least 40%, more preferably at least 50%, even more preferably at least 60%, and even more preferably at least 70%, 80%, or 90% as long as the reference sequence. The amino acid residues (or nucleotides) at corresponding positions are then compared. Amino acid or nucleic acid "identity" is equivalent to amino acid or nucleic acid "homology".

In a preferred comparison of a putative SAg homologue polypeptide and a native SAg protein, the percent identity between two amino acid sequences is determined using the Needleman and Wunsch alignment algorithm (incorporated into the GAP program in the GCG software package (available at the URL www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another embodiment, the percent identity between the encoding nucleotide sequences is determined using the GAP program in the GCG software package (also available at above URL), using a NWSgapdna.CMP matrix and a gap weight of 40, 50, 60, 70, or 80 and a length weight of 1, 2, 3, 4, 5, or 6. In another embodiment, the algorithm of Meyers et al., supra (incorporated into the ALIGN program, version 2.0), is implemented using a PAM120 weight residue table, a gap length penalty of 12 and a gap penalty of 4.

The wild-type (or native) SAg-encoding nucleic acid sequence or the SAg protein sequence can further be used as a "query sequence" to search against a public database, for example, to identify other family members or related sequences. Such searches can be performed using the NBLAST and XBLAST programs, supra (see Altschul et al. (1990) *J. Mol. Biol.* 215:403-10). BLAST nucleotide searches can be performed with the NBLAST program, score=100, wordlength=12 to identify nucleotide sequences homologous to native SAgs. BLAST protein searches can be performed with the XBLAST program, score=50, wordlength=3 to identify amino acid sequences homologous to identify polypeptide molecules homologous to a native SAg. To obtain gapped alignments for comparison purposes, Gapped BLAST can be utilized as described in Altschul et al. (1997, supra). Default parameters of XBLAST and NBLAST can be found at the NCBI website (www.ncbi.nlm.nih.gov)

Using the FASTA programs and method of Pearson and Lipman, a preferred SAg homologue is one that has a z value >10. Expressed in terms of sequence identity or similarity, a preferred SAg homologue for use according the present invention has at least about 20% identity or 25% similarity to a native SAg. Preferred identity or similarity is higher. More preferably, the amino acid sequence of a homologue is substantially identical or substantially similar to a native SAg sequence as those terms are defined above.

One group of substitution variants (also homologues) are those in which at least one amino acid residue in the peptide molecule, and preferably, only one, has been removed and a different residue inserted in its place. For a detailed description of protein chemistry and structure, see Schulz, G. E. *Principles of Protein Structure* Springer-Verlag, New York, 1978, and Creighton, T. E., *Proteins: Structure and Molecular Properties*, W.H. Freeman & Co., San Francisco, 1983, which are hereby incorporated by reference. The types of substitutions which may be made in the protein or peptide molecule of the present invention may be based on analysis of the frequencies of amino acid changes between a homologous protein of different species, such as those presented in Table 1-2 of Schulz et al. (supra) and FIG. 3-9 of Creighton (supra). Based on such an analysis, conservative substitutions are defined herein as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, kg, Lys;
4. Large aliphatic, nonpolar residues: Met, Leu, Ile, Val (Cys); and
5. Large aromatic residues: Phe, Tyr, Trp.

The three amino acid residues in parentheses above have special roles in protein architecture. Gly is the only residue lacking any side chain and thus imparts flexibility to the chain. Pro, because of its unusual geometry, tightly constrains the chain. Cys can participate in disulfide bond formation which is important in protein folding. Tyr, because of its hydrogen bonding potential, has some kinship with Ser, Thr, etc.

More substantial changes in functional or immunological properties are made by selecting substitutions that are less conservative, such as between, rather than within, the above five groups, which will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (a) substitution of gly and/or pro by another amino acid or deletion or insertion of Gly or Pro; (b) substitution of a hydrophilic residue, e.g., Ser or Thr, for (or by) a hydrophobic residue, e.g., Leu, Ile, Phe, Val or Ala; (c) substitution of a Cys residue for (or by) any other residue; (d) substitution of a residue having an electropositive side chain, e.g., Lys, Arg or His, for (or by) a residue having an electronegative charge, e.g., Glu or Asp; or (e) substitution of a residue having a bulky side chain, e.g., Phe, for (or by) a residue not having such a side chain, e.g., Gly.

The deletions and insertions, and substitutions according to the present invention are those which do not produce radical changes in the characteristics of the protein or peptide molecule. However, when it is difficult to predict the exact effect of the substitution, deletion, or insertion in advance of doing so, one skilled in the art will appreciate that the effect will be evaluated by routine screening assays, for example direct or competitive immunoassay or biological assay of T cell function as described herein. Modifications of such proteins or peptide properties as redox or thermal stability, hydrophobicity, susceptibility to proteolytic degradation or the tendency to aggregate with carriers or into multimers are assessed by methods well known to the ordinarily skilled artisan.

Chemical Derivatives

Covalent modifications of the SAg proteins or peptide fragments thereof, preferably of SEs or peptide fragments thereof, are included herein. Such modifications may be introduced into the molecule by reacting targeted amino acid residues of the protein or peptide with an organic derivatizing agent that is capable of reacting with selected side chains or terminal residues. This may be accomplished before or after polymerization.

Cysteinyl residues most commonly are reacted with a-haloacetates (and corresponding amines), such as 2-chloroacetic acid or chloroacetamide, to give carboxymethyl or carboxyamidomethyl derivatives. Cysteinyl residues also are derivatized by reaction with bromotrifluoroacetone, α-bromo-(5-imidozoyl)propionic acid, chloroacetyl phosphate, N-alkylmaleimides, 3-nitro-2-pyridyldisulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing a -amino-containing residues include imidoesters such as methyl picolinimidate; pyridoxal phosphate; pyridoxal; chloroborohydride; trinitrobenzenesulfonic acid; 0-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pK of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form 0-acetyl tyrosyl species and 3-nitro derivatives, respectively.

Carboxyl side groups (aspartyl or glutamyl) are selectively modified by reaction with carbodiimides as noted above. Aspartyl and glutamyl residues are converted to asparaginyl and glutaminyl residues by reaction with ammonium ions.

Glutaminyl and asparaginyl residues may be deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the a-amino groups of lysine, arginine, and histidine side chains (T. E. Creighton, *Proteins: Structure and Molecule Properties*, W.H. Freeman & Co., San Francisco, pp. 79-86 (1983)), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable of mediating such effects are disclosed, for example, in *Remington's Pharmaceutical Sciences*, 16th ed., Mack Publishing Co., Easton, Pa. (1980).

Superantigen Homologues and Fusion Proteins

The variants or homologues of native SAg proteins or peptides including mutants (substitution, deletion and addition types), fusion proteins (or conjugates) with other polypeptides, are characterized by substantial sequence homology to (a) the long-known SE's—SEA, SEB, SEC1-3, SED, SEE and TSST-1;
(b) long-known SpE's;
(c) more recently discovered SE's (SEG, SEH, SEI, SEJ, SEK, SEL, SEM, SEN, SEO, SEP, SER, SEU, SETs 1-5); or
(d) non-enterotoxin superantigens (YPM, *M. arthritides* superantigen).

Preferred homologues were disclosed above.

Table 2 below lists a number of native SEs and exemplary homologues (amino acid substitution, deletion and addition variants (mutants) and fragments) with z values >10 (range: z=16 to z=136) using the Lipman-Pearson algorithm and FASTA. These homologues also induce significant T lymphocyte mitogenic responses that are generally comparable to native SE's.

In addition, as shown in Table 3, several of these homologues also promote antigen-nonspecific T lymphocyte killing in vitro by a mechanism termed "superantigen-dependent cellular cytotoxicity" (SDCC) or, in the case of SAg-mAb fusion proteins, "superantigen/antibody dependent cellular cytotoxicity (SADCC).

According to the present invention, other SE homologues (e.g., z>10 or, in another embodiment, having at least about 20% sequence identity or at least about 25% sequence similarity when compared to native SEs), exhibiting T lymphocyte mitogenicity, SDCC or SADCC, are useful anti-tumor agents when administered to a tumor bearing host via any intrathecal route

TABLE 2

SE-Homologues Induce T Lymphocyte Mitogenesis

| SE Homologue a | T Lymphocyte Mitogenic Response b (ED50) c | Reference (SPECIES) |
|---|---|---|
| SEA (native) | 1 | Abrahmsen et al., EMBO J. 14: |
| SEA D227A | 1057 | 2978-2986 (1995); |
| SEA F47A | 52 | HUMAN |
| SEA H225A | 1272 | |
| SEA K123A/D132G | 2 | |
| SEA N128A | 2 | |
| SEA K55A | 1 | |
| SEA H50A | 4 | |
| SEA D45A | 1 | |
| SEA H187A | 11 | |
| SEA E191A/N195A | 1 | |
| SEA C96S | 12 | Grossman et al., *J. Immunol.* |
| SEA C106Q | 13 | 147: 3274-3281 (1991) |
| SEA C96, 106G | 10 | MOUSE |
| SEA K14E | 1 | Bavari et al., *J. Infect. Dis.* 174: |
| SEA Y64A | 100 | 338-345 (1996) |
| SEA Y92A | 100 | HUMAN |
| SEB (native) | 1 | Briggs et al., *Immunol.* 90: 169- |
| SEB H166A/V169E | 5 | 175 (1997) |
| SEB H166A | 1.3 | MOUSE |
| SEB V169A | 10 | |
| SEB V169E | 5 | |
| SEB V169K | 10 | |
| SEB (native) | 1 | Alakhov et al., *Eur. J. Biochem.* |
| SEB (1-13, 2-13) | 7.6 | 209: 823-828 (1992) |
| | | HUMAN |
| SEB (native) | 1 | Leder et al., *J. Exp. Med.* 187: |
| SEB L20T | 1.2 | 823-833 (1998) |
| SEB V26Y | 1 | MOUSE |
| SEB Y91B | 1.8 | |
| SEC3 (native) | 1 | |
| SEC3 Y26A | 7 | |
| SEC3 N60A | 6 | |
| SEC3 Y90A | 8 | |

TABLE 2-continued SE-Homologues Induce T Lymphocyte Mitogenesis

| SE Homologue a | T Lymphocyte Mitogenic Response b (ED50) c | Reference (SPECIES) |
| --- | --- | --- |
| SEC3 G106A | 6 | |
| SEC1 (native) | 1 | Hoffman et al., *Infect. Immun.* 62: |
| SEC 1818 (delete 7-9) | 1 | 3396-3407 (1994) |
| SEC 1819 (delete 6-10) | 1 | HUMAN |
| SEC 1820 (delete 9-13) | 1 | |
| SEC 1821 (delete 9-18) | 53 | |
| SEC Mr (20-80) | 4.3 | Spero et al., *J. Biol. Chem.* 24: 8787-8791 (1978) MOUSE |
| SED (native) | 1 | Sundstrom et al., *EMBO J.* |
| SED F42A | ~100 | 15: 6832-6840 (1996) |
| SED D182A | ~5000 | HUMAN |
| SED 218A | ~1 | |
| SED D222A | ~100,000 | |
| SEE (native) | 1 | Lamphear et al., *J. Immunol.* |
| SEE-Ala (20-24) | 1 | 156: 2178-2185 (1996) |
| SEE-Ala (200-207) | 1 | HUMAN |
| SEE-Ala (20-24/200-207) | 1.7 | |
| SEA (native) | 1 | Mollick et al., *J. Exp. Med.* 283- |
| SEA-SEE (200-207) | 1 | 293 (1993) |
| SEE-SEA (70-71) | 1 | HUMAN |
| SEA-SEE (200-207) | | |
| TSST-1 (native) | 1 | Kum et al., *J. Infect. Dis.* 174: |
| G31R | 800 | 1261-1270 (1996) HUMAN |
| SEA-C215 mAb Fab Fusion Protein | 1 | Antonnson et al., *J. Immunol.* 158: 4245-4251 (1997) |
| SEE-C215 mAb Fab Fusion protein | 10 | HUMAN |
| SEE/AA-C215 mAb Fab Fusion protein | 1 | |
| SEE/A-C-C215 mAb Fab Fusion protein | 10 | |
| SEE/A-F-C215 mAb Fab Fusion protein | 10 | |
| SEE/A-H-C215 mAb Fab Fusion protein | 10 | |
| SEA/E-BDEG-mAb Fab Fusion protein | 2 | |
| SEE/A-AH-215mAb Fab Fusion protein | 2 | |
| 5T4FabV13-SEAD227A Fusion protein | 1 | Borghae et al., *J. Clin. Oncol.* 27: 4116-23 (2009) |
| 5T4FabV18-SEA/E-120 Fusion protein (SEA/E-120 linked to fragment antigen binding moiety of a monoclonal antibody recognizing the tumor-associated antigen 5T4.) | 10 | Forsberg et al., *J Immunother* 33: 492-499 (2010) HUMAN |
| SEA/E-21 Fusion proteins (this and all below are conjugated to C215 or 5T4 tumor associated antigens) | 1.0 | Forsberg G et al U.S. Pat. Ser. No. 7,125,554 (2009) HUMAN |
| SEA/E-62 | 0.5 | |
| SEA/E-97 | 1.0 | |
| SEA/E-63 | 0.5 | |
| SEA/E-64 | 0.5 | |
| SEA/E-108 | 0.9 | |
| SEA/E-65 | 0.5 | |
| SEA/E-90 | 1.0 | |
| SEA/E-84 | 1.0 | |
| SEA/E-68 | 1.0 | |
| SEA/E-74 | 0.5 | |
| SEA/E-91 | 0.1 | |
| SEA/E-75 | 1 | |
| SEA/E-93 | none | |
| SEA/E-107 | 0.1 | |
| SEA/E-113 | 0.5 | |
| SEA/E-109 | 0.04 | |
| SEA/E-110 | 0.005 | |
| SEA/E-115 | 0.01 | |
| SEA/E-118 | 0.005 | |
| SEA/E-119 | 0.05 | |

TABLE 2-continued

SE-Homologues Induce T Lymphocyte Mitogenesis

| SE Homologue a | T Lymphocyte Mitogenic Response b (ED50) c | Reference (SPECIES) |
|---|---|---|
| SEA/E-120 | 0.04 | |
| SEA/E-121 | 0.05 | |
| SEA/E-122 | 0.006 | |

Legend for Table 2
(a) z values for homologues range from 16-136.
(b) Summary of Methods in all the above studies: human peripheral blood mononuclear cells (PBMC) or mouse spleen or lymph node lymphocytes were incubated with native SE or homologue (mutant) in complete medium supplemented with fetal calf serum (5 or 10% v/v) and antibiotics in wells of 96-well microplates in 200 μl volumes. In some cases, enriched or purified T lymphocytes from these populations were tested. Between $0.2 \times 10^5$ and $8 \times 10^5$ cells/well were used. Incubation was at 37° C. in humidified air/95% $CO_2$ for periods of between 66 hours and 84 hours (depending on whether unfractionated or purified T lymphocytes were being used). T lymphocyte mitogenic responses was routinely measured as radiolabeled [3H]-thymidine ("TdR") incorporation during the final 4-24 hrs of incubation. Cells were always harvested from the microplates onto glass fiber filters which were dried and placed in a liquid scintillation counter for evaluation of incorporated radiolabel.
(c) Each SE or homologue was tested over a range of concentrations and the results were plotted as counts/min (cpm) of [3H]TdR taken up (after subtraction of background cpm of cells incubated in medium alone, which rarely exceeded several hundred cpm) on the ordinate vs. log concentration of the SE or homologue on the abscissa. For each agent tested, the concentration at which [3H]TdR incorporation was 50% of maximum (the ED50), which falls in the linear part of the sigmoid dose-response curve, has been provided in the publication or interpolated visually and approximated (value preceded by "~" symbol) from the published graphs. The ED50 of the native SE was arbitrarily set to 1, so an ED50 of 10 for a homologue indicates that the homologue causes half-maximal mitogenic responsiveness at a 10-fold higher concentration.

TABLE 3

SE Homologues Induce T Lymphocyte Mitogenesis and Anti-Tumor Effects In Vitro

| SE Homologue | T Lymphocyte Mitogenic Response[1] (ED50) | SDCC[2] (ED50) | SADCC[3] (% of native SE) Abrahmsen et al., WO96/01650 |
|---|---|---|---|
| Data from: Abrahmsen et al., EMBO J. 14: 2978-2986 (1995) | | | |
| SEA (native) | 1 | 1 | 100 |
| SEA D227A | 1057 | 132 | 100 |
| SEA F47A | 52 | 4 | 100 |
| SEA H225A | 1272 | 130 | nd |
| SEA K123A/D132G | 2 | 2 | 100 |
| SEA N128A | 2 | 3 | 100 |
| SEA K55A | 1 | 1 | nd |
| SEA H50A | 4 | 2 | 100 |
| SEA D45A | 1 | 1 | nd |
| SEA H187A | 11 | 9 | 100 |
| SEA E191A/N195A | 1 | 1 | nd |
| Data from Sundstrom et al., EMBO J. 15: 6832-6840 (1996) | | | |
| SED (native) | 1 | 1 | |
| SED F42A | ~100 | ~5 | |
| SED D182A | ~5000 | ~50 | |
| SED H218A | ~1 | ~1 | |
| SED D222A | ~50,000 | ~50 | |
| Data from Nilsson et al., J. Immunol. 163: 6686-6693 (1999) | | | |
| SEH (native) | 1 | 1 | |
| SEH D167 | 10 | 5 | |
| SEH D203A | 7 | 5 | |
| SEH D208A | 300 | 10 | |

Legend for Table 2:
1 Lymphocyte Proliferation Assays:
(a) Abrahmsen et al., 1995: Peripheral blood mononuclear cells (PBMC) from heparinized blood of normal donors were isolated by density centrifugation over Ficoll-Hypaque. Following this, $2 \times 10^5$ PBMC/0.2 ml complete medium were incubated in microplates with varying amounts of SEA or SEA mutants for 72 h and tested for mitogenic responses (proliferation) by incorporation of [3H]-thymidine during the last 4 h of culture. The SEA mutant concentration resulting in half-maximum proliferation (ED50) was related to the ED50 of the native SE, arbitrarily set to 1 (see column 2). Thus, the SEA homologue concentration to induce half maximal response was related to the same values induced by native SEA.
(b) Sundstrom et al., 1996: $10^5$ human PBMC prepared as above were incubated at 37° C. in 0.2 ml complete medium in U-shaped microplate wells with varying amounts of native SED or SED mutants for 96 hrs. Proliferation was estimated by incorporation of [3H] thymidine added during the final 24 hrs. ED50 values were estimated by interpolating the curves in this publication.
(c) Nilsson et al., 1999: $2 \times 10^5$ human PBMC were prepared as above incubated in flat bottom microwells in 0.2 ml volumes at 37° C. for 72 h with varying amounts of native SEH and variants. Each well was pulsed with 0.5 μCi [3H]thymidine for 4 h. Cells were harvested and proliferation measured as incorporation of [3H]thymidine. The ED50 values of the SEH variants were related to the ED50 of native SEH which was 0.2 pM.

2 SDCC=Superantigen dependent mediated cellular cytotoxicity. This assay measures the ability of an SE (whether native or mutant) to target cytotoxic T lymphocytes onto MHC class II+ target cells resulting in their lysis. The same conditions were used in the above publications. The cytotoxicity of SE (wt) and homologues against MHC class II+ Raji cells was analyzed in a standard 4 or 6 hour $^{51}$Cr_release assay, using SE-specific T cell lines that had been stimulated in vitro (with the wild-type SE) as effector cells. Briefly, $2.5 \times 10^{3}$ $^{51}$Cr-labeled Raji cells were incubated in 0.2 ml medium (RPMI, 10% FCS) in microwells in the presence effector cells at an effector:target cell ratio of 30 and in the presence (or absence for negative controls) of the SE's or homologues. After incubation, 0.1 ml of medium was withdrawn and counted in a gamma counter to determine isotope release. % specific cytotoxicity was calculated as $$100 \times \left[ \frac{(c.p.m. \text{ experimental release} - c.p.m. \text{ background release})}{(c.p.m. \text{ total release} - c.p.m. \text{ background release})} \right].$$

The SE homologue concentration resulting in half-maximum cytotoxicity (ED50) was related to the ED50 of the native SE, arbitrarily set to 1. Thus, the SE homologue concentration needed to promote half maximal cytotoxicity was related to the same values induced by the native or wild SE. ED50 values were provided by the authors, or, in the case of the Lundstrom reference, they were estimated by interpolating the curves in this publication (shown as approximate using the ~ symbol.

3 SADCC=Superantigen-tumor specific antibody mediated cellular cytotoxicity. This is similar to SDCC but involves an antibody component in the form of a fusion protein that directs the specificity of the targeting. Here, this assay measure the ability of a fusion protein comprising an SE (native or mutant) fused to an antibody Fab fragment to target activated cytotoxic T lymphocytes onto tumor cells expressing the tumor antigen (colon cancer antigen) against which the antibody (C215) is specific. This targeting leads to tumor cell lysis, as above. The cytotoxicity of C215Fab-SEA(wt), C215Fab-SEA(m), SEA(wt) and SEA mutants against C215+MHC class II (neg colon carcinoma cells SW 620 was analyzed in a standard 4 hour $^{51}$Cr3+-release assay, using in vitro stimulated SEA specific T cell lines as effector cells. Briefly, $^{51}$Cr3+-labeled SW 620 cells were incubated at $2.5 \times 10^{3}$ cells per 0.2 ml medium {RPMI, 10% FCS) in microtiter wells at effector to target cell ratio 30:1 in the presence or absence (control) of the additives. Percent specific cytotoxicity was calculated as for SDCC assays.

Fusion Partners for Native SEs or SE Homologues
Antibodies

Nucleic acids encoding fusion partners for the egc SAg or egc SAg homologues include tumor specific antibodies, preferably F(ab')2, Fv or Fd fragments thereof, that are specific for antigens expressed on the tumor. In another embodiment, a fusion partner consists of nucleic acids encoding a polypeptide ligand for a receptor expressed on tumor cells.

One advantage of nucleic acids encoding tumor specific antibody proteins in the fusion polypeptides is prolonged half-life and enhanced tissue penetration. Intact antibodies in which the Fc fragment of the Ig chain is present will exhibit slower blood clearance than their Fab' fragment counterparts, but a fragment-based fusion polypeptide will generally exhibit better tissue penetrating capability.

Preferentially, the nucleic acids encoding a tumor targeting structure in the superantigen conjugate (e.g., tumor specific antibody, Fab or single chain Fv fragments or tumor receptor ligand) has a greater affinity for the tumor than the SAg in the conjugate has for the class II molecule thus preventing the SAg from binding all MHC class II receptors and favoring binding of the conjugate to the tumor. In the case of SEB, the dominant epitope for neutralizing antibodies 225-234 is recombinantly or biochemically bound to the tumor targeting molecule e.g., tumor specific antibodies, Fas or Fv fragments. In so doing, it sterically interferes with the recognition of the dominant epitope by preexisting antibodies.

To further enhance the affinity of the tumor specific antibody in the conjugate gene product for tumor cells in vivo, tumor specific antibodies are used which are specific for more than one antigenic structures on the tumor, tumor stroma or tumor vasculature or any combination thereof. The tumor specific antibody or $F(ab')_2$, Fab or single chain Fv fragments are mono or divalent like IgG, polyvalent for maximal affinity like IgM or chimeric with multiple tumor (tumor stroma or tumor vasculature) specificities. Thus, when the SAg-MoAb conjugate is administered in vivo, it will preferentially bind to tumor cells rather than to endogenous SE antibodies or MHC class II receptors.

To reduce affinity of the SAg-mAb conjugate gene product for endogenous MHC class II binding sites, the high affinity Zn++ dependent MHC class II binding sites in SEA, SEC2, SEC3, SED, SPEA, SPEC, SPEG, SPEH, SMEZ, SMEZ2, *M. arthritides* are deleted or replaced by inert sequence(s) or amino acid(s). These structural alterations in SE or SPEA reduce the affinity for MHC class II receptors from a Kd of $10^{-7}$ or $10^{-8}$ to $10^{-5}$. SEB, SEC and SSA and other SEs or SPEs do not have a high affinity Zn++ dependent MHC class II binding site but have multiple low affinity MHC class II binding sites (Kd $10^{-5}$-$10^{-7}$). In these cases, alteration of the MHC class II binding sites is not always necessary to further reduce affinity for MHC class II receptors; at the very least mutation of one or two of the low affinity MHC class II binding sites will suffice in most instances.

Most importantly, tumor specific antibodies, Fab, $F(ab')_2$ or single chain Fab or Fv fragments in the SAg-mAb conjugate gene product have a higher affinity for tumor antigens (Kd $10^{-11}$-$10^{-14}$ or lower) than for the superantigen has for MHC class II binding sites (Kd $10^{-5}$ to $10^{-7}$) and its dominant epitope has for superantigen specific antibodies (Kd $10^{-7}$ to $10^{-11}$). In this way, the conjugate will bind preferentially to the tumor target in vivo rather than preexisting antibodies or MHC class II receptors.

Fab fragment gene products include the constant domain of the light chain (CL) and the first constant domain (CH1) of the heavy chain. Fab' fragments differ from Fab fragments by the addition of a few residues at the C-terminus of CH1 domain including one or more cysteine(s) from the antibody hinge region. $F(ab')_2$ fragments were originally produced as pairs of Fab' fragments that have hinge cysteines between them. Other chemical couplings of antibody fragments are also known.

An "Fv" fragment gene product is the minimum antibody fragment that contains a complete antigen-recognition and binding site. This region consists of a dimer of one heavy chain and one light chain variable domain in tight, con-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

"Single-chain Fv" or "scFv" antibody fragment gene products comprise the VH and VL domains of antibody, wherein these domains are present in a single polypeptide chain. Generally, the Fv polypeptide further comprises a polypeptide linker between the VH and VL domains that enables the scFv to form the desired structure for antigen binding.

The following documents, incorporated by reference, describe the preparation and use of functional, antigen-binding regions of antibodies: U.S. Pat. Nos. 5,855,866; 5,965,132; 6,051,230; 6,004,555; and 5,877,289.

"Diabodies" gene products are small antibody fragments with two antigen-binding sites, which fragments comprise a heavy chain variable domain (VH) connected to a light chain variable domain (VL) in the same polypeptide chain (VH and VL). By using a linker that is too short to allow pairing between the two domains on the same chain, the domains are forced to pair with the complementary domains of another chain and create two antigen-binding sites. Diabodies are described in EP 404,097 and WO 93/11161, incorporated herein by reference. "Linear antibodies", which can be bispecific or monospecific, comprise a pair of tandem Fd segments (VH-CH1-VH-CH1) that form a pair of antigen binding regions.

The antibody fusion partner gene product for use in the present invention may be specific for tumor cells, tumor stroma or tumor vasculature. Antigens expressed on tumor cells that are suitable targets for mAb-SAg fusion protein therapy include erb/neu, MUC1, 5T4 and many others. Antibodies specific for tumor vasculature bind to a molecule expressed or localized or accessible at the cell surface of blood vessels, preferably the intratumoral blood vessels, of a vascularized tumor. Such molecules include endoglin (TEC-4 and TEC-11 antibodies), a TGFβ. receptor, E-selectin, P-selectin, VCAM-1, ICAM-1, PSMA, a VEGF/VPF receptor, an FGF receptor, a TIE, an αvβ3 integrin, pleiotropin, endosialin and MHC class II proteins. Such antibodies may also bind to cytokine-inducible or coagulant-inducible products of intratumoral blood vessels. Certain preferred agents will bind to aminophospholipids, such as phosphatidylserine or phosphatidylethanolamine.

A tumor cell-targeting antibody gene product or an antigen-binding fragment gene product thereof, may bind to an intracellular component that is released from a necrotic or dying tumor cell. Preferably such antibody gene products are mAbs or fragments thereof that bind to insoluble intracellular antigen(s) present in cells that may be induced to be permeable, or in cell ghosts of substantially all neoplastic and normal cells, but are not present or accessible on the exterior of normal living cells of a mammal.

Anti-tumor stroma antibodies gene products bind to a connective tissue component, a basement membrane component or an activated platelet component; as exemplified by binding to fibrin, RIBS (receptor-induced binding site) or LIBS (ligand-induced binding site).

Fusion protein gene product optionally include linkers or spacers. Numerous types of disulfide-bond containing linkers are known that can be successfully employed to fuse the SAg to an antibody or fragment, certain linkers are preferred based on differing pharmacological characteristics and capabilities. For example, linkers that contain a disulfide bond that is sterically "hindered" are preferred, due to their greater stability in vivo, thus preventing release of the SAg moiety prior to binding at the site of action.

Preferably one or a plurality of fusion proteins gene are incorporated in VASTA in Construct 1. The cDNAs ext Coaguligand In Construct 1, nucleic acids encoding SAg conjugated to, or operatively associated with nucleic acids encoding polypeptides that are capable of directly or indirectly stimulating coagulation, thus forming a "coaguligand" are also contemplated (Baringa M et al., *Science* 275:482-4 (1997); Huang X et al., *Science* 275:547-50 (1997); Ran S et al., *Cancer Res* 1998 Oct. 15; 58(20):4646-53; Gottstein C et al., *Biotechniques* 30:190-4 (2001)).

Nucleic acids encoding coaguligands may also include nucleic acids encoding a tumor specific antibody which may be directly linked to a direct or indirect coagulation factor, or may be linked to a second binding region that binds and then releases a direct or indirect coagulation factor. The second binding region' approach generally uses a coagulant-binding antibody as a second binding region, thus resulting in a bispecific antibody construct. The preparation and use of bispecific antibodies in general is well known in the art, and is further disclosed herein.

Coaguligands are prepared by recombinantly linked to nucleic acid sequences encoding the SAg and then cloned into the VASTA for transduction of tumor cells, normal cells or treatment resistant tumor cells.

Where coagulation factors are used in connection with the present invention, any recombinant linkage to the SAg should be made at a site distinct from the functional coagulating site. The compositions are thus "linked" in any operative manner that allows each region to perform its intended function without significant impairment. Thus, the SAg binds to and stimulates T cells, and the coagulation factor promotes blood clotting.

Preferred nucleic acids encoding coagulation factors are Tissue Factor ("TF") compositions, such as truncated TF ("tTF"), dimeric, multimeric and mutant TF molecules. tTF is a truncated TF that is deficient in membrane binding due to removal of sufficient amino acids to result in this loss. "Sufficient" in this context refers to a number of transmembrane amino acids originally sufficient to insert the TF molecule into a cell membrane, or otherwise mediate functional membrane binding of the TF protein. The removal of a "sufficient amount of transmembrane spanning sequence" therefore creates a tTF protein or polypeptide deficient in phospholipid membrane binding capacity, such that the protein is substantially soluble and does not significantly bind to phospholipid membranes. tTF thus substantially fails to convert Factor VII to Factor VIIa in a standard TF assay yet retains so-called catalytic activity including the ability to activate Factor X in the presence of Factor VIIa.

U.S. Pat. No. 5,504,067, specifically incorporated herein by reference, describes tTF genes and proteins. Preferably, the TFs for use herein will generally lack the transmembrane and cytosolic regions (amino acids 220-263) of the protein. However, the tTF molecules are not limited to those having exactly 219 amino acids.

Any of the nucleic acids encoding truncated, mutated or other TF constructs may be prepared in dimeric form employing the standard techniques of molecular biology and recombinant expression, in which two coding regions are arranged in-frame and are expressed from an expression vector. Various chemical conjugation technologies may be employed to prepare TF dimers. Individual TF monomers may be derivatized prior to conjugation.

The nucleic acids encoding tTF constructs may be multimeric or polymeric, which means that they include 3 or more TF monomeric units. A "multimeric or polymeric TF construct" is a construct that comprises a first monomeric TF molecule (or derivative) linked to at least a second and a third monomeric TF molecule (or derivative). The multimers preferably comprise between about 3 and about 20 such monomer units. The constructs may be readily made using either recombinant techniques or conventional synthetic chemistry.

Nucleic acids encoding TF mutants deficient in the ability to activate Factor VII are also useful. Such "Factor VII activation mutants" are generally defined herein as TF mutants that bind functional Factor VII/VIIa, proteolytically activate Factor X, but substantially lack the ability to proteolytically activate Factor VII.

The ability of such Factor VII activation mutants gene products to function in promoting tumor-specific coagulation requires their delivery to the tumor vasculature and the presence of Factor VIIa at low levels in plasma. A gene product such as a conjugate of a Factor VII activation mutant will be localize within the vasculature of a vascularized tumor. Prior to localization, the TF mutant would be generally unable to promote coagulation in any other body sites, on the basis of its inability to convert Factor VII to Factor VIIa. However, upon localization and accumulation within the tumor region, the mutant will then encounter sufficient Factor VIIa from the plasma in order to initiate the extrinsic coagulation pathway, leading to tumor-specific thrombosis. Exogenous Factor VIIa could also be administered to the patient to interact with the TF mutant and tumor vasculature.

Any one or more of a variety of nucleic acids encoding Factor VII activation mutants may be prepared and used in connection with the present invention. The Factor VII activation region generally lies between about amino acid 157 and about amino acid 167 of the TF molecule. Residues outside this region may also prove to be relevant to the Factor VII activating activity. Mutations are inserted into any one or more of the residues generally located between about amino acid 106 and about amino acid 209 of the TF sequence (WO 94/07515; WO 94/28017; each incorporated herein by reference).

A variety of other nucleic acids encoding coagulation factors may be used in connection with the present invention, as exemplified by the agents set forth below. Thrombin, Factor V/Va and derivatives, Factor VIII/VIIIa and derivatives, Factor IX/IXa and derivatives, Factor X/Xa and derivatives, Factor XI/XIa and derivatives, Factor XII/XIIa and derivatives, Factor XIII/XIIIa and derivatives, Factor X activator and Factor V activator may be used in the present invention.

Nucleic acids encoding the preferred coaguligand are fused in frame with nucleic acids encoding a SAg or SAg homologue of any type or in combination, although one or a plurality of native SAgs in the enterotoxin gene cluster (egc) SEG, SEI, SEM, SEN, SEO or one or more of a native egc superantigen or egc superantigen homologue or a mixture of native egc superantigens and egc superantigen homologues is/are preferred. Nucleic acids encoding other native SAg or SAg homologues such as SEA, SEB, SEC, SED, SEE, SEQ, SER, SEU, TSST-1 and *Y. pseudotuberculosis* used alone or in combinations among themselves or with egc superantigens are also useful.

The nucleic acid encoding SAg-coaguligand-VASTA-costimulatory molecules are used to transduce tumor cells, normal cells or treatment resistant tumor cells as described herein for Construct 1.

Cytokines as Fusion Partners

Nucleic acids encoding cytokines or their extracellular domains are an effective partner for SAgs in Construct 1. A preferred fusion polypeptide comprises a SAg fused to T cell anti-apoptotic cytokines. Whereas SAg stimulation of T cells can result in activation-driven cell death. several cytokines interfere with this process (Vella et al., *Proc. Natl. Acad. Sci.*

95: 3810-3815 (1998)). IL-3, IL-7, IL-15, IL-17, IL-23, IL-27 prevent SAg-stimulated T cells from undergoing apoptosis in vivo and in vitro and promote T cell development and proliferation. In addition, because of their ability to promote selective proliferation by Th1 T cells, IL-12 and IL-18 are desirable. IL-18 is preferred for intratumoral injection because it induces tumor suppressive cytokines IFNγ and TNFα and IL-1β, and rescues cytotoxic T cells from apoptosis.

Accordingly, in Construct 1, nucleic acids encoding SAg-mAb (or F(ab')2, Fab, Fd or single chain Fv fragments) fusion protein as described above are fused recombinantly to nucleic acids encoding the extracellular domains of one or more cytokines from a group consisting of IL-2. IL-7 or IL-3 or IL-12 or IL-15 or IL-17, IL-18, IL-23, IL-27. Nucleic acids encoding the cytokine of choice is fused in frame with nucleic acids encoding the SAg.

Costimulatory Molecules as Fusion Partners
Superantigens Fused to Costimulatory Molecules OX40L or 4-1BBL or B7 Family In Construct 1, a preferred fusion polypeptide for SAg comprises a potent costimulatory molecule, preferably the ECD of a transmembrane costimulatory protein. Costimulatory molecules are preferred fusion partner in the instant invention because they increase the survival of antigen, lectin and SE-activated of CD8+ memory T cells compared to SE alone (Takahashi et al., *J Immunol* 162:5037-5040 (1999). 4-1BBL is a costimulatory molecule that relays costimulatory signals in antigen-stimulated primary T cell cultures and in lectin-driven activation of." thymocytes (Hurlado, J. C. et al J. Immunol 158(6); 2600-2609, 1997). 4-1BBL belongs to the tumor necrosis factor receptor superfamily, a group of cysteine-rich cell surface molecules (Vinay, D. S. et al, Seminars in Immunology, 1998, Vol. 10, pp. 481^89). The gene for the murine 4-1 BBL is disclosed in GenBank under Accession No. U02567. The gene for the human homolog, hu4-1BBL is disclosed in GenBank under Accession No. U03397.

In the present context, nucleic acids encoding SAg and a costimulatory molecules such as 4-1BBL further augments the immunogenicty of self antigens (tumor antigens) that are structurally altered by SAg-viral transfection of tumor cells and normal cells. Nucleic acids encoding costimulatory molecule 4-1BB ligand are the preferred. Construct 1 comprise nucleic acids encoding the complete molecule or ECDs of 4-1BB ligand as disclosed in Goodwin et al. *Eur. J. Immunol.* 23: 2631-2641 (1993); Melero I et al., *Eur. J. Immunol.* 28: 1116-1121 (1998); Kown B S et al., *Proc. Natl. Acad. Sci. USA* 86:1963-67 (1989); Shuford W W et al., *J. Exp. Med.* 186: 47-55 (1997) or OX-40 ligand as disclosed in Godfrey et al., *J. Exp. Med.* 180: 757-762 (1994); Gramaglia I et al., *J. Immunol.* 161: 6510-6517 (1998) or CD-38 as disclosed in Jackson D G et al., *J. Immunol.* 144: 2811-2817 (1990); Zilber et al., *Proc. Nat'l Acad. Sci. USA* 97: 2840-2845 (2000).

```
4-1BB Ligand
(Alderson, M. R. et al., Eur. J. Immunol. 24 (9), 2219-2227 (1994))
                                                        [SEQ ID NO: 39]
  1  MEYASDASLD PEAPWPPAPR ARACRVLPWA LVAGLLLLLL LAAACAVFLA CPWAVSGARA

61  SPGSAASPRL REGPELSPDD PAGLLDLRQG MFAQLVAQNV LLIDGPLSWY SDPGLAGVSL

121  TGGLSYKEDT KELVVAKAGV YYVFFQLELR RVVAGEGSGS VSLALHLQPL RSAAGAAALA

181  LTVDLPPASS EARNSAFGFQ GRLLHLSAGQ RLGVHLHTEA RARHAWQLTQ GATVLGLFRV

241  TPEIPAGLPS PRSE
```

OX-40L is a type II membrane protein with limited homology to TNF and is stimulatory to OX-40$^{+}$ T cells in vitro. The murine and human OX-40L cDNAs have 68% homology at the nucleotide level and 46% at the amino acid level. Human OX-40L stimulates human T cells exclusively, while murine OX-40L stimulates both human and mouse T cells. APC express OX-40L and can transmit the OX-40L: OX-40R signal during presentation of antigen to CD4$^{+}$ T cells. OX-40L signaling is important for differentiation of human dendritic cells and leads to increased production of IL-12, TNF-a, IL-1B, and IL-6. (Weinberg, A. D. et al 1998 *Seminars in Immunology*, Vol. 10:471480). OX-40L is a potent costimulatory molecule for sustaining primary CD4$^{+}$ T cell responses, used in combination with B7-1 (Gramaglia, I. et al 1998 *J. Immunology*, Vol. 161:6510-7. The gene sequences of this molecule is within the confines of the present invention.

```
OX40 Ligand
(Hikami, K., et al., Genes Immun. 1 (8), 521-522 (2000))
                                                        [SEQ ID NO: 40]
  1  MERVQPLEEN VGNAARPRFE RNKLLLVASV IQGLGLLLCF TYICLHFSAL QVSHRYPRIQ

61  SIKVQFT
```

B7 represents a family of costimulatory molecules within the Ig gene superfamily. The members include murine B7.1 (CD80) and B7.2 (CD86). B7.1 and B7.2 are the natural ligands of CD28/CTLA-4 (CD 152). The gene sequence of murine B7.1 is disclosed in Freeman et al (J. Immunol 143: 2714-2722, 1989) and in GENBANK under Accession No. X60958. The gene sequence of murine B7.2 is disclosed in Azuma et al (Nature 366:76-79, 1993) and in GEN BANK under Accession No, L25606 and MUSB72X.

The human homologs of the murine B7 costimulatory molecules and functional portions thereof within the scope of the present invention. The human homologue of the murine B7 costimulatory molecules include CD80, the homolog of murine B7.1, and CD86, the homolog of B7.2. The gene sequence of human B7.1 (CD80) is disclosed in GENBANK under Accession No. M27533, and the gene sequence of human B7.2 (CD86) is disclosed under Accession No. U04343 and AF099105.

Intercellular adhesion molecule-1 (murine ICAM-1, CD54) and the human homologue, CD54, also acts as a costimulatory molecule. Its ligand is leukocyte function-associated antigen-1 (LFA-1, CD11a/CD18) which is expressed on the surface of lymphocytes and granulocytes. The gene for murine ICAM-1 is disclosed in GenBank under Accession No. X52264 and the gene for the human ICAM-1 homo log, (CD54), is disclosed in Accession No. J03132. In one embodiment, the recombinant vector of the present invention contains a foreign nucleic acid sequence encoding at least one murine ICAM-1 molecule, human homologue, other mammalian homolog or functional portion thereof in addition to foreign nucleic acid sequences encoding two or more additional costimulatory molecules.

The costimulatory molecule leukocyte function antigen 3, murine LFA-3 (CD48), and its human homolog LFA-3' (CD58), a glycosy 1-phosphatidylinositol-linked glycoprotein, is a member of the CD2 family within the immunoglobulin gene superfamily. The natural ligand of LFA-3 is CD2 (LFA-2) which is expressed on thymocytes, T cells, B cells and NK cells. The gene for murine LFA-3 is disclosed in GenBank under Accession No. X53526 and the gene for the human homolog is disclosed in Accession No. Y00636.

The present invention provides VASA-SAg encoding one or multiple costimulatory molecules. Such nucleic acid sequences are selected that encode one or more costimulatory molecules selected from the group consisting of B7, ICAM-I, LFA-3,4-1BBL, CD59, CD40, CD70, VCAM-1, OX-40L and the like. The VASA-SAg of the present invention further provides at least one promoter sequence for controlling the expression of the costimulatory molecules which are well established in the art.

The SAg and costimulatory nucleic acids are used in a form suitable for expression of the desired molecule, i.e., the nucleic acid contains all of the coding and regulatory sequences required for transcription and translation of a gene, which may include promoters, enhancers and polyadenylation signals, secretory signals and sequences necessary for transport of the molecule to the surface of the tumor cell, including N-terminal signal sequences. When the nucleic acid is a cDNA incorporated into a virus, viral genomic DNA or recombinant expression vector, the regulatory functions responsible for transcription and/or translation of the cDNA are may be provided by viral sequences. An example of such a molecule is shown in FIG. 1. After administration to tumor bearing hosts in vivo, Constructs 2, 3 and 4 induce a powerful immune response against altered self epitopes in the tumor cell resulting in tumor eradication.

Viruses that Alter Self/TAA Antigens (VASTA) on Tumor Cells and Normal Cells

Viruses (vectors or genomic DNA) incorporating nucleic acids encoding SAg are used for infection of tumor cells and normal cells of the same histologic type as the tumor. These viruses are selected for their ability to alter self/tumor antigens and render them immunogenic. Molecules encoded within the viral vector are expressed efficiently in cells which have taken up viral vector nucleic acid. The viral nucleic acid may be a DNA or RNA molecule as long as it retains the ability to alter and express self/tumor antigens.

In constructs 1, 2, 3 and 4 nucleic acids encoding SAg are inserted into VASTA or its genomic DNA. Viruses described below for insertion of the SAg transgene are useful in this invention. Viruses useful for this purpose include any virus capable of altering self-antigens in tumor cells and normal cells such that they elicit an immune response in the host. To date, this property has been demonstrated for vesicular stomatitis virus but has not been demonstrated for the viruses listed in Table 1. Nevertheless, in view of their ability to integrate into the genome of tumor cells they are potential candidates to alter self/tumor antigens and render them immunogenic to the host.

A preferred vector of the present invention is a recombinant virus which is capable of efficient delivery of genes to multiple cell types, including normal cells and tumor cells, altering self/tumor antigens in such transduced cells and increasing their immunogenicity in the host. Such viruses with these properties are collectively referred to as VASTA. Vesicular stomatitis virus is the archetypical VASTA The site between genes G and L of the vesicular stomatitis virus (VSV) genomic plasmid pVSV-XN2 is useful for insertion of SAg. It displays an adjuvant effect when combined recombinantly with other antigens including TAAs. This VSV or its genomic DNA incorporates a SAg and a costimulatory molecule as used to transduce tumor cells and normal cells in Construct 1. It is also used in Constructs 2, 3, 4 to incorporate cDNA extracted from such transduced cells is prepared using a recombinant method for insertion of a foreign gene in VSV described herein in Example 2 and in Fernandez M et al., *J Virol* 76: 895-904 (2002) incorporated by reference.

Other viruses with the above properties are also useful in Constructs 1, 2, 3, 4. Herpes simplex virus type 1 (HSV-1) deleted for ICP34.5, provides tumor-selective replication, and ICP47 deletion increases US11 expression, which enhances virus growth and replication in tumor cells normal cells In the present invention nucleic acids encoding SAg-costimulatory molecule replaces the deleted ICP34.5 region in Construct 1 and used to transduce tumor cells and normal cells. cDNA extracted from such cells is incorporated into Constructs 2, 3, 4 and used for administration to the host as described herein.

Similarly, Construct 1 may comprise JX-594, a replication-competent Wyeth strain vaccinia virus genetically modified to integrate SAg-costimulatory molecules under the control of a synthetic early/late promoter. The genes are initially cloned into the SalI and BglII sites of the plasmid transfer vector pSC65. The same virus/vector system can be used to incorporate cDNA extracted from tumor cells and normal cells for administration to the host as described herein.

Poxviruses are also useful in the present invention include replicating and non-replicating vectors such as orthopox, vaccinia, raccoon pox, rabbit pox and the like, avipox, suipox, capri-pox and the like. Poxviruses may be selected from the group consisting of vaccinia-Copenhagen, vaccinia-Wyeth strain, vaccinia-MVA strain, NY VAC, fowlpox, TROVAC, canarypox, ALVAC, swinepox, and the like.

Additional viral vectors useful in this invention include but are not limited to adenovirus, alphavirus, retrovirus, picornavirus, iridovirus, self-replicating RNA replicons (replicase nucleic acids) derived from alphavirus vectors, such as Sindbis virus, Semliki Forest virus, or Venezuelan equine encephalitis viruses. Insertion method of SAg into adenovirus variant is disclosed in U.S. Ser. No. 10/428,817—Example 60 incorporated by reference. Lentiviral vectors capable of incorporating nucleic acids of three or more molecules (Zuffrey et al., Nature Biotech 15: 871-875 (1997)) incorporated herein by reference are useful in the present invention. Other viruses that have natural core engineered properties (Kirn et al. *Nat. Med.* 7: 781-187 (2001); Alemany et al., *Nat. Biotechnology* 18: 723-730 (2000)) incorporated by reference in entirety are useful in this invention.

The recombinant vector of the present invention comprises at least one expression control element operably linked to the nucleic acid sequence. The expression control elements are inserted into the vector to control and regulate the expression of the nucleic acid sequence (Ausubel et al, 1987, in "Current Protocols in Molecular Biology, John Wiley and Sons, New York, N.Y). Expression control elements are known in the art and include promoters. Promoters useful in the present invention are the SV40 (simian virus 40) early promoter, the RSV (Rous sarcoma virus) promoter, the adenovirus major late promoter, the human CMV (cytomegalovirus) immediate early I promoter, poxvirus promoters which include but are not limited to 30K, 13, sE/L, 7.5K, 40K, and the like. These control elements are also useful for nucleic acids encoding SAg and costimulatory molecules. An especially useful vector for SAg is the phβ Apr-neo containing the human β actin promoter and SV40 (FIG. 2).

In an embodiment of the invention, a VASTA is provided comprising a SAg sequence encoding a SAg molecule or functional portion thereof under control of a first promoter, a costimulatory molecule sequence encoding a costimulatory molecule or functional portion thereof under control of a second promoter. Additional molecular sequences may also be employed that encode a third or fourth SAg or costimulatory molecule or functional portions thereof under control of a third or fourth promoter.

The recombinant vector of the present invention is able to infect, transfect or transduce host cells in a host. The host includes but is not limited to mammals. The host cells are any cell amenable to infection, transfection or transduction by the recombinant vector or VASTA and capable of expressing the foreign genes from the recombinant vector at functional levels. The host cells include but are not limited to any tumor cell, any treatment resistant tumor cell or any normal cell. Such cells can be syngeneic, allogeneic or xenogeneic to the host. Such cells can be obtained from cell cultures, whole blood or from biopsies of tumor or normal tissues including lymph nodes. Normal cells include fibroblasts, muscle cells, APCs and antigen presenting precursor cells such as monocytes, macrophages, DC, Langerhans cells and the like. Infection of the host cells allows expression of each foreign, exogenous costimulatory molecule and expression of the foreign nucleic acid sequence encoding target antigen(s) if present in the recombinant vector. The host cells express, or are engineered to express, the appropriate MHC (HLA) Class I or II molecules for appropriate antigenic presentation to $CD4^+$ and/or $CD8^+$ T cells. As such virtually any mammalian cell may be engineered to become an appropriate antigen presenting cell expressing multiple costimulatory molecules.

Table 1 below shows several viruses and insertion sites for nucleic acids encoding SAg, costimulatory molecules as in Construct 1 and cDNA extracted from tumors and normal cells as in Constructs 2, 3, 4.

TABLE 1

VASTA useful for insertion of nucleic acids encoding SAg

| Adenovirus | Deletions | Herpes Simplex Virus (HSV) | Deletions |
|---|---|---|---|
| ONYX-015 | E1B-55k deletion | NV1066 | ICP0/ICP4/γ34.5 deletions |
| AdΔ24 | 24-bp deletion in E1A region rendering the virus ineffective in cells with intact Rb pathways. | G207 | ICP6/γ34.5 deletions |
| AdΔ24 hNIS gene.Ad5-yCD/mutTKSR39rep-hNIS | E1A-deleted expresses a highly efficient fusion protein of the catalytic domains of yeast cytosine deaminase (yCD) and herpes virus thymidine kinase (mutTKSR39) | G207 NV1023 | γ34.5-deleted HSV γ34.5/UL24/UL56/US11/ICP47 deletions |
| Ad-ΔE1B19/55 | deletion of the E1B 19kD protein | rRp450 | Insertion of the CYP2B1 gene into the UL39 locus of herpes virus hrR3 resulted in a virus γ34.5-deleted |
| hNIS-dl309 (ΔE3B) and dl704 (ΔE3gp19kD) | expresses adenovirus E3B-deleted adenoviruses encoding antisense cDNA for cell cycle regulating proteins (chk1, chk2, plk-1), | HSV-1716 R3616 (inactivated γ34.5) | |
| E1B 55kD-deleted adenoviruses, | encoding activators of apoptosis (ZD55-TRAIL and ZD55-SMAC) | NV1066 | |
| Ad-ΔE1B19/55 | deletion of the E1B 19kD protein | Vaccinia Virus | |
| Ad5-yCD/mutTKSR39rep-ADP | encodes yCD which converts the prodrug 5-FC into 5-FU | vvDD-SSTR2 | Expresses the human somatostatin receptor |
| CV706 | Prostate specific | GLV-1h68 | F14.5L/J2R/A56R deleted, Lister strain vaccinia virus |
| CV787 adenovirus OBP-301 | Prostate specific telomerase-specific, replication-selective adenovirus | Vesicular Stomatis Virus cDNAs from tumors or normal cells from which the tumor originated are amplified from the BioExpress shuttle vector by PCR and cloned into the VSV genomic plasmid pVSV-XN2 (between VSV G and L genes). Virus is generated from BHK cells by cotransfection of pVSV-XN2- | |

TABLE 1-continued

VASTA useful for insertion of nucleic acids encoding SAg

| Adenovirus | Deletions | Herpes Simplex Virus (HSV) | Deletions |
|---|---|---|---|
| | | cDNA library DNA along with plasmids encoding viral genes | |
| AdΔ24-p53 | | Measles viruus | expresses FMG |
| AdΔ24RGD | | Recombinant Edmonston strain MV | |
| CRAd-S-pk7 | | Parvovirus | a stable dominant-negative p53 mutant |
| AdΔ24-p53 | | H-1 parvovirus wild type | |
| AdAM6 | | Reovirus | |
| Ad-ΔE1B55 | | | |

Constructs 2, 3 and 4: cDNAs Extracted from Tumor Cells, Normal Cells or Treatment-Resistant Tumor Cells Transduced with Nucleic Acids Encoding VASTA-SAg-Costimulatory Molecules cDNAs containing a CpG backbone from tumor cells, normal cells and treatment resistant cells transduced with SAgs-VASTA-costimulatory molecules are extracted as described in Example 2 herein. The extracted cDNA or RNA is then integrated into a VASTA as described in Example 2 and used as preventative or therapeutic vaccine as in animal models and humans as in Examples 3, 4, 5, 6, 7.

Sickle Erythrocytes, Mesenchymal Stem Cells, T Cells, CD14+Monocyte-Derived Dendritic Cells, Cytokine Induced Killer Cell, Irradiated Cell Lines as Carriers of VASTA Operatively Linked to Nucleic Acids Encoding SAg and Costimulatory Molecules The present invention contemplates that erythrocytes or erythroblasts from patients with any form of sickle hemoglobinopathy are useful. These include erythrocytes or erythroblasts from hemizygous sickle S and A hemoglobin, sickle hemoglobin-C disease, sickle beta plus thalassemia, sickle hemoglobin-D disease, sickle hemoglobin-E disease, homozygous C or C-thalassemia, hemoglobin-C beta plus thalassemia, homozygous E or E-thalassemia. Indeed, any erythrocyte or erythroblasts with or without sickle hemoglobin expressing receptors capable of binding to tumor neovasculature are useful in the inventions described herein. Particularly useful are those cells which express hemoglobin S in combination with other types of hemoglobin. Both mature and nucleated forms of these cells are useful. The present invention also contemplates that normal or sickle erythrocytes or sickle variants, e.g., HbSC cells, and nucleated progenitors which are upregulated by hormones, cytokines, biologically active agents, drugs, chemical or physical treatments to express adhesive properties or to enhance expression of adhesive properties are also useful in this invention. The transfection of these cells with therapeutic transgenes and their use in vivo is described comprehensively in U.S. Ser. Nos. 12/586,532 and 12/276,941 incorporated in their entirety by reference.

Potentially any cell can be used as a virus carrier. These cells, their preparation, transfection with transgenes and therapeutic use in vivo are given as follows: Irradiated cell lines (Iankov I D, Blechacz B, Liu C, et al. *Mol Ther* 15:114-22 (2007)); Raykov Z et al., *Oncol Rep* 17:1493-9 (2007)), cytokine induced killer cells (Thorne S H et al., *Science* 311:1780-4 (2006)), activated T cells (Ong H T et al., *Gene Ther* 14:324-33 (2007)), mesenchymal stem cell (Komarova S et al., *Mol Cancer Ther* 5:755-66 (2006)) and CD14+ monocyte-derived dendritic cells (Peng K W et al., *Am J Hematol*; 84:401-7 (2009)) are all useful. MSCs are attractive as cell carriers because, in addition to their reported ability to home to tumors (Kidd S, et al., *Cytotherapy* 10:657-67 (2008)), adipose tissue-derived MSC are readily obtained from adipose tissues that are available as surgical wastes from gastric bypass or from fat biopsies. MSC can be expanded to large numbers in cellular therapy and clinical experience with infusion of MSC into humans is available (Giordano A et al., *Cell Physiol* 2007; 211:27-35)).

Applicable Tumors

The compositions of the claimed inventions are useful in the treatment of both primary and metastatic solid tumors and carcinomas of the breast; colon; rectum; lung; oropharynx; hypopharynx; esophagus; stomach; pancreas; liver; gallbladder; bile ducts; small intestine; urinary tract including kidney, bladder and urothelium; female genital tract including cervix, uterus, ovaries, choriocarcinoma and gestational trophoblastic disease; male genital tract including prostate, seminal vesicles, testes and germ cell tumors; endocrine glands including thyroid, adrenal, and pituitary; skin including hemangiomas, melanomas, sarcomas arising from bone or soft tissues and Kaposi's sarcoma; tumors of the brain, nerves, eyes, and meninges including astrocytomas, gliomas, glioblastomas, retinoblastomas, neuromas, neuroblastomas, Schwannomas and meningiomas; solid tumors arising from hematopoietic malignancies such as leukemias and including chloromas, plasmacytomas, plaques and tumors of mycosis fungoides and cutaneous T-cell lymphoma/leukemia; lymphomas including both Hodgkin's and non-Hodgkin's lymphomas. The compositions are also be useful for the prevention of metastases from the tumors described above either when used alone or in combination with radiotherapeutic, photodynamic, and/or chemotherapeutic treatments conventionally administered to patients for treating disorders, including angiogenic disorders. Treatment of a tumor with surgery, photodynamic therapy, radiation and/or chemotherapy is followed by administration of the compositions to extend the dormancy of micrometastases and to stabilize and inhibit the growth of any residual primary tumor or metastases. The compositions can be administered before, during, or after radiotherapy; before, during, or after chemotherapy; and/or before, during, or after photodynamic therapy.

Chemotherapeutic and Other Agents

Chemotherapeutic agents can be used together with all the claimed Constructs described herein. They can be administered parenterally intravenously, intrapleurally, intrathecally, intravesicularly, intratumorally by infusion or injection or in some cases orally before, concomitantly with or after the claimed Constructs or with carrier cells containing the Constructs. Anti-cancer chemotherapeutic drugs useful in this invention include but are not limited to antimetabolites, anthracycline, vinca alkaloid, anti-tubulin drugs, antibiotics and alkylating agents. Representative specific drugs that can be used alone or in combination include cisplatin (CDDP), adriamycin, dactinomycin, mitomycin, carminomycin, daunomycin, doxorubicin, tamoxifen, TAXOL™, taxotere, vincristine, vinblastine, vinorelbine, etoposide (VP-16), 5-fluorouracil (5FU), cytosine arabinoside, cyclophosphamide, thiotepa, methotrexate, camptothecin, actinomycin-D, mitomycin C, aminopterin, combretastatin(s) and derivatives and prodrugs thereof.

Another newer class of drugs also termed "chemotherapeutic agents" comprises inducers of apoptosis. Any one or more of such drugs, including genes, vectors, antisense constructs, siRNA constructs, and ribozymes, as appropriate, may be used in conjunction with these constructs disclosed herein. Anti-angiogenic agents, such as angiostatin, endostatin, vasculostatin, canstatin and maspin. Drugs that target small molecules in tumor are also useful such a Gleevic, Sunifimab, and other agents that target tyrosine kinase receptor molecules on tumors.

Chemotherapeutic agents are administered as single agents or multidrug combinations, in full or reduced dosage per treatment cycle. They can be administered by any of the above routes described above. The choice of chemotherapeutic drug in such combinations is determined by the nature of the underlying malignancy. For lung tumors, cisplatin is preferred. For breast cancer, a microtubule inhibitor such as taxotere is the preferred. For malignant ascites due to gastrointestinal tumors, 5-FU is preferred.

Constructs 2, 3, 4 and chemotherapeutics are delivered using parenteral, intravenous, intrapleural, intraperitoneal, intratumoral, intracutaneous, intramuscular, intrathecal or intratumoral routes. For intratumoral administration, the tumors are preferably visible by x-ray, CT, PET scanning, ultrasound, bronchoscopy, laparoscopy, culdoscopy. Representative tumors that are treatable with intratumoral therapy include but are not limited to hepatocellular carcinoma, lung tumors, brain tumors, head and neck tumors and unresectable breast tumors. Multiple tumors at different sites may be treated by intratumoral Constructs 2, 3, 4.

The chemotherapeutic agent(s) selected for therapy of a particular tumor preferably is one with the highest response rates against that type of tumor. For example, for non-small cell lung cancer (NSCLC), cisplatin-based drugs have been proven effective. Cisplatin may be given parenterally or intratumorally. When given intratumorally, Cisplatin is preferentially in small volume around 1-4 ml although larger volumes can also work. The smaller volume is designed to increase the viscosity of the Cisplatin containing solution in order to minimize or delay the clearance of the drug from the tumor site. Other agents useful in NSCLC include the taxanes (paclitaxel and docetaxel), vinca alkaloids (vinorelbine), antimetabolites (gemcitabine), and camptothecin (irinotecan) both as single agents and in combination with a platinum agent.

The optimal chemotherapeutic agents and combined regimens for all the major human tumors are set forth in *Bethesda Handbook of Clinical Oncology*, Abraham J et al., Lippincott William & Wilkins, Philadelphia, Pa. (2001); *Manual of Clinical Oncology*, Fourth Edition, Casciato, D A et al., Lippincott William & Wilkins, Philadelphia, Pa. (2000) both of which are herein incorporated in entirety by reference.

In one embodiment, these recommended chemotherapeutic agents are used alone or combined with other chemotherapeutics in full doses. For intratumoral administration, the dose of a chemotherapeutic drug or biologic agent is preferably reduced up to 95% of the FDA-recommended dose for parenteral administration.

Cisplatin has been widely used to treat cancer, with effective doses of 20 mg/m$^2$ for 5 days every three weeks for a total of three courses. Preferred dose per treatment for intratumoral use of Cisplatin is 5-10 mg whereas for intrathecal use 20-80 mg may be administered. Intratumoral cisplatin may be given every 7-14 days for 10-20 treatments whereas intrathecal cisplatin may be given every 2-6 weeks for 10-20 treatments. Cisplatin delivered in small volumes, e.g., 5-10 mg/1-5 ml saline, is extremely viscous and may be retained in a tumor for a sustained period, thereby acting like a controlled release drug being released from an inert surface. This is indeed the preferred mode of administration of Cisplatin when administered intratumorally with or without the SAg. Preferably cisplatin is administered together with the SAg in the same syringe.

Other chemotherapeutic compounds include doxorubicin, etoposide, verapamil, podophyllotoxin, and the like which are administered through intravenous bolus injections at doses ranging from 25-75 mg/m$^2$ at 21 day intervals for adriamycin, to 35-50 mg/m$^2$ for etoposide intravenously.

Other agents and therapies that are operable together with or after intratumoral SAg include, radiotherapeutic agents, antitumor antibodies with attached anti-tumor drugs such as plant-, fungus-, or bacteria-derived toxin or coagulant, ricin A chain, deglycosylated ricin A chain, ribosome inactivating proteins, sarcins, gelonin, aspergillin, restricticin, a ribonuclease, a epipodophyllotoxin, diphtheria toxin, or *Pseudomonas* exotoxin. Additional cytotoxic, cytostatic or anti-cellular agents capable of killing or suppressing the growth or division of tumor cells include anti-angiogenic agents, apoptosis-inducing agents, coagulants, prodrugs or tumor targeted forms, tyrosine kinase inhibitors (Siemeister et al., 1998), antisense strategies, RNA aptamers, siRNA and ribozymes against VEGF or VEGF receptors (Saleh et al., 1996; Cheng et al., 1996; Ke et al., 1998; Parry et al., 1999; each incorporated herein by reference).

Any of a number of tyrosine kinase inhibitors are useful when administered together with, or after, intratumoral SAg. These include, for example, the 4-aminopyrrolo[2,3-d]pyrimidines (U.S. Pat. No. 5,639,757). Further examples of small organic molecules capable of modulating tyrosine kinase signal transduction via the VEGF-R2 receptor are the quinazoline compounds and compositions (U.S. Pat. No. 5,792,771). Other agents which may be employed in combination with SAgs are steroids such as the angiostatic 4,9(11)-steroids and $C^{21}$-oxygenated steroids (U.S. Pat. No. 5,972,922). Thalidomide and related compounds, precursors, analogs, metabolites and hydrolysis products (U.S. Pat. Nos. 5,712,291 and 5,593,990) may also be used in combination with SAgs and other chemotherapeutic drugs agents to inhibit angiogenesis. These thalidomide and related compounds can be administered orally.

Certain anti-angiogenic agents that cause tumor regression may be administered together with, or after, intratumoral SAg. These include the bacterial polysaccharide CM101 (currently in clinical trials as an anti-cancer drug) and the antibody LM609. CM101 has been well characterized for its ability to induce neovascular inflammation in tumors. CM101 binds to and cross-links receptors expressed on dedifferentiated endothelium that stimulate the activation of the complement system. It also initiates a cytokine-driven inflammatory response that selectively targets the tumor. CM101 is a uniquely antiangiogenic agent that downregulates the expression VEGF and its receptors. Thrombospondin (TSP-1) and platelet factor 4 (PF4) may also be used together with or after intratumoral SAg. These are both angiogenesis inhibitors that associate with heparin and are found in platelet α granules.

Interferons and metalloproteinase inhibitors are two other classes of naturally occurring angiogenic inhibitors that can be used together with or after intratumoral SAg. Vascular tumors in particular are sensitive to interferon; for example, proliferating hemangiomas are successfully treated with IFNα. Tissue inhibitors of metalloproteinases (TIMPs), a family of naturally occurring inhibitors of matrix metalloproteases (MMPs), can also inhibit angiogenesis and can be used in combination with SAgs.

Pharmaceutical Compositions and Administration

Constructs 2, 3 and 4 obtained from normal cells or tumor cells are administered individually via a parenteral route preferably intravenously and preferably on alternate days for up to 30 days per cycle. For malignant pleural effusions, ascites or meningeal tumors, Constructs 2, 3 and 4 are administered individually via intrapleural, intraperitoneal or intrathecal routes respectively on alternate days until there is no further fluid reaccumulation. Constructs 2, 3, 4 are also delivered to a host using a syringe, a catheter, or a needle-free injection device such as a gene gun. Constructs 2, 3 and 4 are also administered individually via the intravenous route on alternate days starting with the first intrapleural or intraperitoneal treatment and continuing until the effusion has failed to reaccumulate. In addition, patients with or without recurrence of pleural effusion or ascites may be treated with the same regimen at 3-6 month intervals. If the pleural space or peritoneal space is inaccessible, Constructs 2 or 3 or 4 may be administered individually via the intravenous route until there is no further fluid accumulation. Constructs 2, 3 and 4 can also be given intratumorally once weekly for 4-12 weeks and the cycle repeated every 2-6 months. Construct 4 is generally used together with Constructs 2 and 3 in order to treat tumor variants that may show a treatment-resistant (as defined herein) and/or metastatic phenotype expressing molecules such as cadherin, adhesion and metaloproteinases. If the tumor under treatment shows a predominantly treatment resistant phenotype then Constructs 2 and 4 may be administered optionally without Construct 3.

Typical pharmaceutical Constructs for parenteral (preferably intravenous) administration include about $1 \times 10^6$-$1 \times 10^7$ PFU/ml per patient per day. These dosages may be used particularly if the agent is administered to lymph node of a tumor bearing patient preferably one that drains a tumor site or is known to contain tumor, although a non tumor containing lymph node is also useful. The same dosages may be injected into a body cavity or into a lumen of an organ such as pleural space, abdominal cavity or bladder. Actual methods for preparing administrable compositions will be known or apparent to those skilled in the art are described in more detail in such publications as Remington's Pharmaceutical Science, 10th ed. Mack Publishing Company, Easton, Pa. (1995).

The pharmaceutical compositions of Constructs 2, 3, 4 which are administered to the host are in the form of a sterile or aseptically produced solution. The carrier cells infected with Construct 1 are prepared by aseptic technique. The nucleic acids encoding SAg operatively linked to VASTA comprise a pharmaceutically acceptable carrier defined as any substance suitable as a vehicle for delivering a VASTA to a suitable in vivo or in vitro site. Preferred carriers are capable of maintaining the VASTA and it's DNA/RNA in a form that is capable of entering the target cell and being expressed by the cell.

Preferred carriers include are water, phosphate buffered saline (PBS), Ringer's solution, dextrose solution, serum-containing solutions, Hank's balanced salt solution, other aqueous, physiologically balanced solutions, oils, esters and glycols. Aqueous carriers can contain suitable additional substances which enhance chemical stability and isotonicity, such as sodium acetate, sodium chloride, sodium lactate, potassium chloride, calcium chloride, and other substances used to produce phosphate buffer, Tris buffer, and bicarbonate buffer and preservatives, such as thimerosal, m- and o-cresol, formalin and benzyl alcohol if not harmful to the VASTA.

Therapeutic compositions of the present invention are maintained in sterile containers and solutions. Although the Constructs of the present invention can be administered in naked form, a liposome may also be used for delivery in vivo. A liposome can remain stable in an animal for a sufficient amount of time, at least about 30 minutes, more preferably for at least about 1 hour and even more preferably for at least about 24 hours, to deliver a nucleic acid molecule to a desired site.

Another preferred delivery system for Constructs 2, 3, 4 is the sickled erythrocyte containing the nucleic acids of choice. The sickled erythrocytes undergo ABO and Rh phenotyping to select compatible cells for delivery. The cells are delivered intravenously or intraarterially in a blood vessel perfusing a specific tumor site or organ e.g. carotid artery, portal vein, femoral artery etc. over the same amount of time required for the infusion of a conventional blood transfusion. The quantity of cells to be administered in any one treatment would range from one tenth to one half of a full unit of blood. The treatments are generally given every three days for a total of twelve treatments. However, the treatment schedule is flexible and may be given for a longer of shorter duration depending upon the patient's response.

An "effective treatment protocol" includes a suitable and effective dose of an agent being administered to a subject, given by a suitable route and mode of administration to achieve its intended effect in treating a disease. Effective doses and modes of administration for a given disease can be determined by conventional methods and include, for example, determining survival rates, side effects (i.e., toxicity) and qualitative or quantitative, objective or subjective, evaluation of disease progression or regression. In particular, the effectiveness of a dose regimen and mode of administration of a therapeutic composition of the present invention to treat cancer can be determined by assessing response rates. A "response rate" is defined as the percentage of treated subjects that responds with either partial or complete remission. Remission can be determined by, for example, measuring tumor size or by microscopic examination of a tissue sample for the presence of cancer cells.

In the treatment of cancer, a suitable single dose can vary depending upon the specific type of cancer and whether the cancer is a primary tumor or a metastatic form. One of skill in the art can test doses of a therapeutic composition suitable for direct injection to determine appropriate single doses for systemic administration, taking into account the usual subject parameters such as size and weight. An effective anti-tumor single dose of a therapeutic recombinant DNA molecule or combination thereof is an amount sufficient amount to result in reduction, and preferably elimination, of the tumor.

One of skill in the art recognizes that the number of doses required depends upon the extent of disease and the response of an individual to treatment. Thus, according to this invention, an effective number of doses includes any number required to cause regression of primary or metastatic disease.

A preferred treatment protocol comprises administrations of single doses (as described above) intravenously on alternate days for up to 30 days. An effective number of doses is about 10 dosings for each Construct.

The therapeutic compositions can be administered by any of a variety of modes and routes, including but not limited to, local administration into a site in the subject animal, which site contains abnormal cells to be destroyed. An example is the local injection within the area of a tumor or a lesion. Another example is systemic administration.

Constructs 2, 3, 4 are delivered locally by direct injection. Direct injection techniques are particularly useful for injecting the composition into a cellular or tissue mass such as a tumor mass or a granuloma mass that has been induced by a pathogen. Constructs 2, 3 and 4 are delivered by systemic administration. Preferred modes and routes of systemic administration include intravenous injection or infusion.

Superantigens with Radiation Therapy

Local radiation to any tumor sites or the mediastinum using the traditional standard dose of 60-65 gy is given concomitant with parenteral (e.g., intrathecal, intravenous, intravesicular, intrapleural intralymphatic or intratumoral) SAg. The radiotherapy is also be given before, during or after the SAg therapy but in either case there is a hiatus of no more than 30 days between the start of SAg therapy and the start or conclusion of radiotherapy. The median survival of patients given this type of radiotherapy alone is 5% at one year whereas the combined modality improves the median survival to more than two years.

In general, local radiation therapy alone has minimal efficacy in contributing to long-term disease control in advanced carcinomas. While radiation is an effective palliative measure to relieve symptoms, only a very small minority of patients achieve long-term survival when treated with radiation alone. However, radiation synergizes with SAg therapy in shrinking tumors and prolonging survival. Radiation is given to bulky or symptomatic lung lesions before, during or after SAg therapy. Preferably it is started 1-2 weeks before SAg treatment and continued simultaneously with SAg for 1-4 weeks until the full courses of SAg and radiation are completed. It may also be started after SAg treatment preferably within 24 hours of the last SAg treatment. Radiation may also be given to a malignant lesion or a tumorous body cavity before, together with or after the site has been injected with SAg intratumoraly or intrathecally and/or systemic/parenteral chemotherapy. It may also be administered to a malignant lesion or site not injected specifically with SAg. In this case the SAg may be given systemically or intrathecally but not directly to the radiated tumor mass or site. Radiation may also be used with chemotherapy in these settings together with systemic and/or intratumoral SAg and intratumoral or systemic chemotherapy.

Radiation techniques are preferably continuous rather than split. Hyperfractionated radiation, employing multiple daily fractions of radiation are preferred to conventionally fractionated radiation. Radiation doses varies from 40-70 gy although a dose between 60 and 70 gy dose is preferred. It is contemplated that radiation doses considered to be subtherapeutic and up to 70% below the conventional doses are also useful when used before, during or after a course of SAg therapy.

Example 1

Nucleic Acids Encoding SAg Fused to a Viral Epitope Induce a Tumoricidal Response Human papilloma virus (HPV-16) is the pathogenic agent underlying most cervical cancers. These tumors express several well defined viral antigens of which HPV-16 E7 is a model. HPV-16 E7 is a zinc binding phosphoprotein with two Cys-X-X-Cys domains composed of 98 amino acids. HPV-16 E7 is characterized as a cytoplasmic/nuclear protein and is more abundant than E6 in HPV-associated cancer cells. Early observations analyzing HPV genomes and the viral transcription pattern in cervical carcinoma cell lines revealed frequent integration of viral DNA and consistent expression of the viral early E7 gene. The same gene is necessary for immortalization of various types of human cells. The HPV oncogenic protein E7 is important in the induction and maintenance of cellular transformation and is coexpressed in most HPV-containing cervical cancers. E7 gene expression is also necessary for the proliferative phenotype of cultured cervical carcinoma cells.

Provided below we demonstrate that nucleic acids encoding a superantigen fused recombinantly to a weak tumor associated antigen (papilloma viral epitope). Because SAg and conventional peptide antigens are aligned in geometrically different conformations on MHC II molecules required for activation of T cells the coexistence of these molecules in a fusion gene (protein) would seem to sterically compromise the effective binding and presentation of each molecule to the TCR. Surprisingly, as shown below a nucleic acid construct encoding a superantigen fused to an oncogenic human papilloma viral epitope abolished the outgrowth of papillomas in mice rabbits whereas nucleic acids encoding a superantigen or the viral epitope alone are ineffective (U.S. application Ser. No. 10/428,817 These results suggest that nucleic acids encoding superantigens can be fused recombinantly to tumor associated antigen (TAA) and when administered in DNA form can augment the immunogenicty of the TAA and generate a tumoricidal response.

Methods

We evaluated protection against carcinoma outgrowth of DNA vaccines comprising SEB fused to various papilloma antigens versus SEB and papilloma antigens alone in mouse and rabbit models. For production and maintenance of murine TC-1 cells, HPV-16 E6. E7 and ras oncogene were used to transform primary C57BL/6 mice lung epithelial cells. The cells were grown in RPMI 1640. supplemented with 10%(v/v) fetal bovine serum, 50 units/ml penicillin/streptomycin. 2 mM L-glutamine, 1 mM sodium pyruvate. 2 mM nonessential amino acids, and 0.4 mg/ml G418 at 37° C. with 5% $CO_2$. On the day of tumor challenge. TC-1 cells were harvested by trypsinization. washed twice with 1× Hanks buffered salt solution, and finally resuspended in 1× Hanks buffered salt solution to the designated concentration for injection.

Nucleotides encoding a SAg and HPV-E6 or 7 polypeptides were cloned into a pcX vector as chimeric nucleotides. Recombinant plasmid DNA was then precipitated pmpt 1.6-μm diameter gold particles at a ratio of 1 μg of DNA/0.5 mg of gold particles. For the tumor protection experiment, mice (five per group) were vaccinated via a gene gun with 2 μg of HPV16-E7, vector, SEB-E7 and E7-SEB fusion genes weekly for three weeks. One week after the last vaccination, mice were s.c. challenged with $5\times10^4$ cells/mouse TC-1 tumor cells in the right leg and then monitored twice a week.

Rabbits were vaccinated by gene gun-mediated intracutaneous delivery of the plasmid DNA in which DNA-gold particle were bombarded at 400 lg/in2 onto rabbit dorsal skin sites. Rabbits received three immunizations at three week intervals with 20 μg of DNA constructs, CRPV E6, E7, E8 genes, SEB gene, and CRPVE1 E6, E7, E8 fused to SEB followed by challenge with cloned CRPV. The animals were examined for papillomas and size measured as length×width. Carcinoma development was confirmed histologically.

Mouse Model: Protection with DNA Vaccine Comprising SEB-E7

Figure 3:
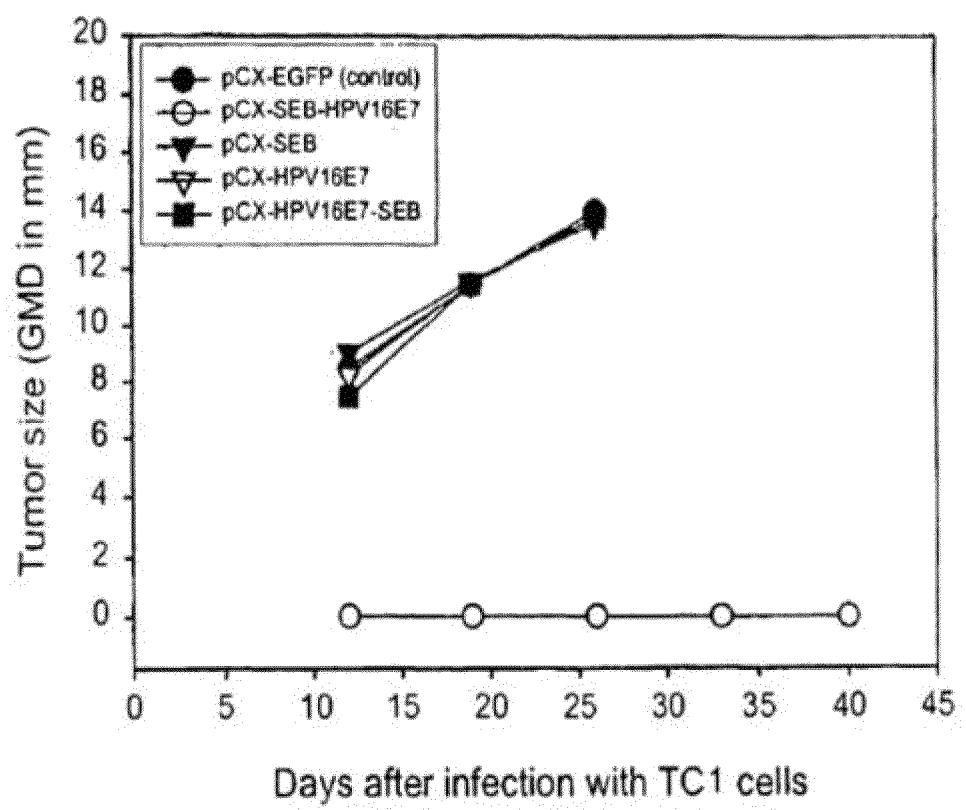
FIG. 3. Protection of mice from tumor growth by DNA immunization with nucleic acid encoding a fusion of human papilloma virus HPV16 oncoprotein (E7) with SEB. C57BL/6 mice were immunized i.d. by particle bombardment (gene gun) with control vector, E7 alone, SEB-E7 and E7-SEB fusion genes. Mice were challenged with syngeneic TC-1 tumor cells transfected with E7 or another HPV oncoprotein, E6. Mice receiving the SEB-E7 fusion gene showed complete protection against challenge. Mice receiving E7-SEB (fusion protein in reverse order), E7 only, SEB and vector all developed tumors.

We used particle bombardment with a gene gun to vaccinate C57BL/6 mice intradermally. Mice received HPV16-E7, vector, SEB-E7 and E7-SEB fusion genes. Mice were challenged with HPV16 E6 and E7-containing TC-1 cells (mice). Mice receiving the SEB-E7 fusion gene showed complete protection against challenge with TC-1 tumour cells, and remained tumour free for 40 days. In contrast, groups of mice receiving E7-SEB, E7 only, SEB and vector all developed tumours that grew rapidly and reached 14 mm in diameter after 4 weeks. See FIG. 3.

Rabbit Model: Protection with DNA Vaccine Comprising SEB-E1

Figure 4:
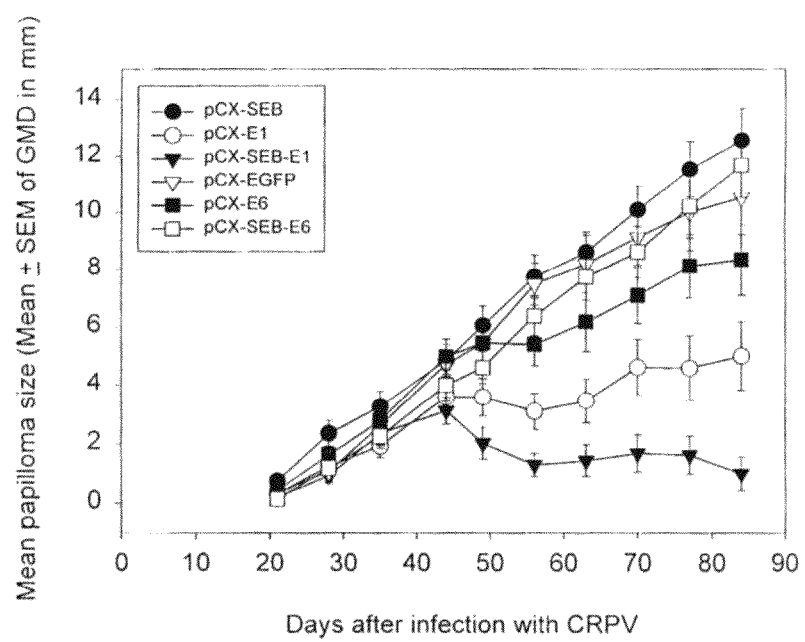
FIG. 4. Protection of rabbits from growth of papilloma tumor caused by cottontail rabbit papillomavirus (CRPV). Inbred EIII/JC rabbits were immunized with DNA. Groups were given CRPV E1 or E6, DNA, SEB DNA, and fusions of SEB with E1 or E6. Rabbits were challenged with CRPV and tumor development was monitored. The SEB-E1 fusion DNA was the most effective in inhibiting the growth of the outgrowth of CRPV-induced papillomas.

Particle bombardment with a gene gun was used to vaccinate inbred EII/JC rabbits intradermally. Rabbits received CRPV E1, E6, E7, E8 genes, SEB gene, and CRPV E1, E6, E7, E8 fused to SEB and were then challenged with CRPV. The SAg-E1 fusion gene was the most effective in inhibiting the outgrowth of CRPV-induced papillomas. See FIG. 4.

Example 2

Construct 1

Construct 1 is prepared by incorporating nucleic acids encoding the SAg and a costimulatory molecule into the genomic plasmid pVSV-XN2 between the G and L genes of vesicular stomatitis virus as shown in FIG. 1 in a method described by Fernandez M et al., *J Virol* 76: 895-904 (2002) incorporated by reference.

Constructs 2, 3 or 4 cDNA libraries from tumor cells (Construct 2), treatment-resistant tumor cells (Construct 3) or normal cells of the same histologic type (Construct 4) that have been infected with Construct 1 consisting of SAg-VASTA-costimulatory genes are extracted with phenol and ethanol-precipitated as described in U.S. Ser. No. 10/428,817—Example 30. These cDNA libraries are cloned into the pCMV.SPORT6 vector (Invitrogen), and amplified by PCR. The cDNA library from each cell type is then cloned into pVSV-XN2 between the Xho1 and Nhe1 sites between the G and L genes and consists of $4.75\times10^{6}$ colony-forming units (at dilutions of $1\times10^{-6}$ and $1\times10^{-5}$ there are five and 45 colonies, respectively). Virus is generated from BHK cells by cotransfection of pVSV-XN2-cDNA library DNA along with plasmids encoding viral genes. Virus is expanded by a single round of infection of BHK cells and purified by sucrose gradient centrifugation. cDNA libraries generated from the tumors or normal cells for insertion into the VSV genomic DNA are size-fractionated to PCR cDNA molecules below 4 kilo-base pairs (kbp), as smaller cDNA inserts are associated with both higher viral titers and lower proportions of defective interfering particles.

cDNA from normal human cells is amplified from the BioExpress shuttle vector by PCR and cloned into the VSV genomic plasmid pVSV-XN2 between the G and L genes. Virus is generated from BHK cells by cotransfection of pVSV-XN2-cDNA library DNA along with plasmids encoding viral genes as described. Titers are measured by plaque assays on BHK-21 cells.

All constructs are tested in vitro to validate their ability to express the desired gene product. Plasmids purified by column (Wizard preps, Promega, Madison. Wis.) or by cesium chloride banding are used to transfect tissue-culture cells transiently. Protein expression is detected by immunoblot. This check not only verifies expression but validates the size and immunoreactivity of the gene product.

These constructs are tested in animal models and humans with cancer as described in Examples 3, 4, 5, 6, 7. Typically inbred mice such as C57BL/6 mice are purchased from Jackson Laboratories at 6-8 weeks of age. Subcutaneous tumors are established by injection of $2\times10^{6}$ tumor cells in 100 μl PBS into the flank. Intratumoral injections are performed in a total of 50 μl. Intravenous injections of a VASTA-SAg-costimulant construct is administered in 100 μl volumes in doses of $1\times10^{-7}$ PFU with a range of $1\times10^{-3}$ to $1\times10^{-10}$ PFU. For survival studies, tumor diameter in two dimensions is measured three times weekly using calipers, and mice are killed when tumor size is approximately 1.0 cm×1.0 cm in two perpendicular directions. Survival data is analyzed using the log-rank test, and the two-sample unequal-variance Student's t test analysis is applied for in vitro assays. Statistical significance is defined as $P<0.05$.

In addition to VSV, other viruses with VASTA properties and their viral genomes are useful in the above method as disclosed herein.

The normal cells preferably display the tissue phenotype identical or similar to that of the tumor cell. Both tumor cells and normal cells can be syngeneic, allogeneic or xenogenic to the host. The normal cells can be obtained from the same patient, from tissue culltured cell lines. Alternatively cDNA extracts of normal cells prepared commercially according to GLP standards are also useful.

Virus Infection of Carrier Cells.

Carrier cells (SS progenitor cell or mesenchymal stem cells) are plated overnight in 6- or 12-well plates and cDNAs from Construct 2, 3 and 4 at various multiplicities of infection (MOI, ratio of virus to cells) are added for 2 h at 37° C., after which inoculum is removed, and the cells cultured for 48 h. Cells are trypsinized and the percentage of red fluorescent VASTA-RFP-infected cells is determined by flow cytometry. Numbers of viable cells are determined by trypan blue exclusion assay at various time points post infection.

Example 3

Tumor Models and Procedures for Evaluating Anti-Tumor Effects of Constructs 2, 3, 4

Construct 2, 3 or 4 describe herein consisting of nucleic acids encoding VASTA-SAg-costimulatory and related constructs extracted from tumor cells or normal cells of the same histologic type or from which the tumor originated are tested for therapeutic efficacy in several well established rodent tumor models described below and in humans in Example 4, 5, 6, 7. These Constructs are administered intravenously or intraperitoneally three to five times weekly in doses of $1\times10^{-6}$ to $10^{-10}$ PFU/ml for up to 10 weeks. An equally efficacious regimen is alternating daily injections of Construct 2, Construct 3 and Construct 4 every other day for up to 1 month. Carrier cells transduced with Constructs 2, 3, or 4 as described herein are administered on an alternate daily schedule in 30 ml volumes for 12 total treatments.

The rodent models used for testing below are considered to be highly representative of a broad spectrum of human tumors. These therapeutic tumor models are described in detail in Geran, R. I. et al., "Protocols for Screening Chemical Agents and Natural Products Against Animal Tumors and Other Biological Systems (Third Edition)", *Cancer. Chemother. Reports* Pt 3, 3:1-112, which is hereby incorporated by reference in its entirety.

A. Calculation of Mean Survival Time (MST)

MST (days) is calculated according to the formula:
$$\frac{S + AS(A-1) - (B+1)NT}{S(A-1) - NT}$$

Day: Day on which deaths are no longer considered due to drug toxicity. For example, with treatment starting on Day 1 for survival systems (such as L1210, P388, B16, 3LL, and W256): Day A=Day 6; Day B=Day beyond which control group survivors are considered "no-takes."

S: If there are "no-takes" in the treated group, S is the sum from Day A through Day B. If there are no "no-takes" in the treated group, S is the sum of daily survivors from Day A onward.

S(A−1): Number of survivors at the end of Day (A−1).

Example: for 3LE21, S(A−1)=number of survivors on Day 5.

NT: Number of "no-takes" according to the criteria given in Protocols 7.300 and 11.103.

B. T/C Computed for all Treated Groups $$T/C = \frac{MST \text{ of treated group}}{MST \text{ of control group}} \times 100$$

Treated group animals surviving beyond Day B are eliminated from calculations (as follows):

| No. of survivors in treated group beyond Day B | Percent of "no-takes" in control group | Conclusion |
|---|---|---|
| 1 | Any percent | "no-take" |
| 2 | <10 | drug inhibition |
|   | ³10 | "no-takes" |
| ³3 | <15 | drug inhibitions |
|   | ³15 | "no-takes" |

Positive control compounds are not considered to have "no-takes" regardless of the number of "no-takes" in the control group. Thus, all survivors on Day B are used in the calculation of T/C for the positive control. Surviving animals are evaluated and recorded on the day of evaluation as "cures" or "no-takes."

Calculation of Median Survival Time (MedST)

MedST is the median day of death for a test or control group. If deaths are arranged in chronological order of occurrence (assigning to survivors, on the final day of observation, a "day of death" equal to that day), the median day of death is a day selected so that one half of the animals died earlier and the other half died later or survived. If the total number of animals is odd, the median day of death is the day that the middle animal in the chronological arrangement died. If the total number of animals is even, the median is the arithmetical mean of the two middle values. Median survival time is computed on the basis of the entire population and there are no deletion of early deaths or survivors, with the following exception:

C. Computation of MedST From Survivors

If the total number of animals including survivors (N) is even, the MedST (days) (X+Y)/2, where X is the earlier day when the number of survivors is N/2, and Y is the earliest day when the number of survivors (N/2)−1. If N is odd, the MedST (days) is X.

D. Computation of MedST from Mortality Distribution

If the total number of animals including survivors (N) is even, the MedST (days) (X+Y)/2, where X is the earliest day when the cumulative number of deaths is N/2, and Y is the earliest day when the cumulative number of deaths is (N/2)+1. If N is odd, the MedST (days) is X. "Cures" and "no-takes" in systems evaluated by MedST are based upon the day of evaluation. On the day of evaluation any survivor not considered a "no-take" is recorded as a "cure." Survivors on day of evaluation are recorded as "cures" or "no-takes," but not eliminated from the calculation.

E. Calculation of Approximate Tumor Weight from Measurement of Tumor Diameters with Vernier Calipers The use of diameter measurements (with Vernier calipers) for estimating treatment effectiveness on local tumor size permits retention of the animals for lifespan observations. When the tumor is implanted sc, tumor weight is estimated from tumor diameter measurements as follows. The resultant local tumor is considered a prolate ellipsoid with one long axis and two short axes. The two short axes are assumed to be equal. The longest diameter (length) and the shortest diameter (width) are measured with Vernier calipers. Assuming specific gravity is approximately 1.0, and Pi is about 3, the mass (in mg) is calculated by multiplying the length of the tumor by the width squared and dividing the product by two. Thus, $$\text{Tumor weight (mg)} = \frac{\text{length (mm)} \times (\text{width [mm]})2}{2} \text{ or } \frac{L \times (W)2}{2}$$

The reporting of tumor weights calculated in this way is acceptable inasmuch as the assumptions result in as much accuracy as the experimental method warrants.

F. Calculation of Tumor Diameters

The effects of a drug on the local tumor diameter may be reported directly as tumor diameters without conversion to tumor weight. To assess tumor inhibition by comparing the tumor diameters of treated animals with the tumor diameters of control animals, the three diameters of a tumor are averaged (the long axis and the two short axes). A tumor diameter T/C of 75% or less indicates activity and a T/C of 75% is approximately equivalent to a tumor weight T/C of 42%.

G. Calculation of Mean Tumor Weight from Individual Excised Tumors

The mean tumor weight is defined as the sum of the weights of individual excised tumors divided by the number of tumors. This calculation is modified according to the rules listed below regarding "no-takes." Small tumors weighing 39 mg or less in control mice or 99 mg or less in control rats, are regarded as "no-takes" and eliminated from the computations. In treated groups, such tumors are defined as "no-takes" or as true drug inhibitions according to the following rules:

| Percent of small tumors in treated group | Percent of "no-takes" in control group | Action |
|---|---|---|
| ≤17 | Any percent | no-take; not used in calculations |
| 18-39 | <10 | drug inhibition; use in calculations |
|  | ≥10 | no-takes; not used in calculations |
| ≥40 | <15 | drug inhibition; use in calculations |
|  | ≥15 | Code all nontoxic tests "33" |

Positive control compounds are not considered to have "no-takes" regardless of the number of "no-takes" in the control group. Thus, the tumor weights of all surviving animals are used in the calculation of T/C for the positive control (T/C defined above) SDs of the mean control tumor weight are computed the factors in a table designed to estimate SD using the estimating factor for SD given the range (difference between highest and lowest observation). Biometrik Tables for Statisticians (Pearson E S, and Hartley H G, eds.) Cambridge Press, vol. 1, table 22, p. 165.

II. Specific Tumor Models

A. Lymphoid Leukemia L1210

Summary:

Ascitic fluid from donor mouse is transferred into recipient BDF1 or CDF1 mice. Treatment begins 24 hours after implant. Results are expressed as a percentage of control survival time. Under normal conditions, the inoculum site for primary screening is i.p., the composition being tested is administered i.p., and the parameter is mean survival time. Origin of tumor line: induced in 1948 in spleen and lymph nodes of mice by painting skin with MCA. *J Natl Cancer Inst.* 13:1328, 1953.

| Animals | One sex used for all test and control animals in one experiment. |
|---|---|
| Tumor Transfer | Inject ip, 0.1 ml of diluted ascitic fluid containing $10^5$ cells |
| Propagation | DBA/2 mice (or BDF1 or CDF1 for one generation). |
| Time of Transfer | Day 6 or 7 |
| Testing | BDF1 (C57BL/6 × DBA/2) or CDF1 (BALB/c × DBA/2) |
| Time of Transfer | Day 6 or 7 |
| Weight | Within a 3-g range, minimum weight of 18 g for males and 17 g for females. |
| Exp Size (n) | 6/group; No. of control groups varies according to number of test groups. |

Testing Schedule

| DAY | PROCEDURE |
|---|---|
| 0 | Implant tumor. Prepare materials. Run positive control in every odd-numbered experiment. Record survivors daily. |
| 1 | Weigh and randomize animals. Begin treatment with therapeutic composition. Typically, mice receive doses of the test composition in 0.5-1 ml saline on schedules as described herein. Controls receive saline alone. Treatment is one dose/week. Any surviving mice are sacrificed after 4 wks of therapy. |
| 5 | Weigh animals and record. |
| 20 | If there are no survivors except those treated with positive control compound, evaluate |
| 30 | Kill all survivors and evaluate experiment. |

Quality Control:

Acceptable control survival time is 8-10 days. Positive control compound is 5-fluorouracil; single dose is 200 mg/kg/injection, intermittent dose is 60 mg/kg/injection, and chronic dose is 20 mg/kg/injection. Ratio of tumor to control (T/C) lower limit for positive control compound is 135%.

Evaluation:

Compute mean animal weight on Days 1 and 5, and at the completion of testing compute T/C for all test groups with >65% survivors on Day 5. A T/C value 85% indicates a toxic test. An initial T/C 125% is considered necessary to demonstrate activity. A reproduced T/C 125% is considered worthy of further study. For confirmed activity a composition should have two multi-dose assays that produce a T/C 125%.

B. Lymphocytic Leukemia P388

Summary:

Ascitic fluid from donor mouse is implanted in recipient BDF1 or CDF1 mice. Treatment begins 24 hours after implant. Results are expressed as a percentage of control survival time. Under normal conditions, the inoculum site for primary screening is ip, the composition being tested is administered ip daily for 9 days, and the parameter is MedST. Origin of tumor line: induced in 1955 in a DBA/2 mouse by painting with MCA. *Scientific Proceedings, Pathologists and Bacteriologists* 33:603, 1957.

| Animals | One sex used for all test and control animals in one experiment. |
|---|---|
| Tumor Transfer | Inject ip, 0.1 ml of diluted ascitic fluid containing $10^6$ cells |
| Propagation | DBA/2 mice (or BDF1 or CDF1 for one generation). |
| Time of Transfer | Day 7 |
| Testing | BDF1 (C57BL/6 × DBA/2) or CDF1 (BALB/c × DBA/2) |
| Time of Transfer | Day 6 or 7 |
| Weight | Within a 3-g range, minimum weight of 18 g for males and 17 g for females. |
| Exp Size (n) | 6/group; No. of control groups varies according to number of test groups. |

Testing Schedule

| DAY | PROCEDURE |
|---|---|
| 0 | Implant tumor. Prepare materials. Run positive control in every odd-numbered experiment. Record survivors daily. |
| 1 | Weigh and randomize animals. Begin treatment with therapeutic composition. Typically, mice receive doses of the test compositions on schedules as described herein in 0.5-1 ml saline Controls receive saline alone. Treatment is as described herein. Any surviving mice are sacrificed after 4 wks of therapy. |
| 5 | Weigh animals and record. |
| 20 | If there are no survivors except those treated with positive control compound, evaluate |
| 30 | Kill all survivors and evaluate experiment. |

Acceptable MedST is 9-14 days. Positive control compound is 5-fluorouracil: single dose is 200 mg/kg/injection, intermittent dose is 60 mg/kg/injection, and chronic dose is 20 mg/kg/injection. T/C lower limit for positive control compound is 135% Check control deaths, no takes, etc.

Quality Control:

Acceptable MedST is 9-14 days. Positive control compound is 5-fluorouracil: single dose is 200 mg/kg/injection, intermittent dose is 60 mg/kg/injection, and chronic dose is 20 mg/kg/injection. T/C lower limit for positive control compound is 135%. Check control deaths, no takes, etc.

Evaluation:

Compute mean animal weight on Days 1 and 5, and at the completion of testing compute T/C for all test groups with >65% survivors on Day 5. A T/C value of 85% indicates a toxic test. An initial T/C of 125% is considered necessary to demonstrate activity. A reproduced T/C 125% is considered worthy of further study. For confirmed activity a composition should have two multi-dose assays that produce a T/C 125%.

C. Melanotic Melanoma B16

Summary:

Tumor homogenate is implanted ip or sc in BDF1 mice. Treatment begins 24 hours after either ip or sc implant or is delayed until an sc tumor of specified size (usually approximately 400 mg) can be palpated. Results expressed as a percentage of control survival time. The composition being tested is administered ip, and the parameter is mean survival time. Origin of tumor line: arose spontaneously in 1954 on the skin at the base of the ear in a C57BL/6 mouse. *Handbook on Genetically Standardized Jax Mice*. Jackson Memorial Laboratory, Bar Harbor, Me., 1962. See also *Ann NY Acad Sci* 100, Parts 1 and 2, 1963.

| | |
|---|---|
| Animals | One sex used for all test and control animals in one experiment. |
| Propagation Strain | C57BL/6 mice |
| Tumor Transfer | Implant fragment sc by trochar or 12-g needle or tumor homogenate* every 10-14 days into axillary region with puncture in inguinal region. |
| Testing Strain | BDF1 (C57BL/6 × DBA/2) |
| Time of Transfer | Excise sc tumor on Day 10-14 from donor mice and implant as above |
| Weight | Within a 3-g range, minimum weight of 18 g for males and 17 g for females. |
| Exp Size (n) | 10/group; No. of control groups varies according to number of test groups. |

*Tumor homogenate: Mix 1 g or tumor with 10 ml of cold balanced salt solution, homogenize, and implant 0.5 ml of tumor homogenate ip or sc. Fragment: A 25-mg fragment may be implanted sc.

Testing Schedule

| DAY | PROCEDURE |
|---|---|
| 0 | Implant tumor. Prepare materials. Run positive control in every odd-numbered experiment. Record survivors daily. |
| 1 | Weigh and randomize animals. Begin treatment with therapeutic composition. Typically, mice receive doses of the test composition in 0.5-1 ml saline on schedules described herein. Controls receive saline alone. Treatment is as described herein. Any surviving mice are sacrificed after 8 wks of therapy. |
| 5 | Weigh animals and record. |
| 60 | Kill all survivors and evaluate experiment. |

Quality Control:

Acceptable control survival time is 14-22 days. Positive control compound is 5-fluorouracil: single dose is 200 mg/kg/injection, intermittent dose is 60 mg/kg/injection, and chronic dose is 20 mg/kg/injection. T/C lower limit for positive control compound is 135% Check control deaths, no takes, etc.

Evaluation:

Compute mean animal weight on Days 1 and 5, and at the completion of testing compute T/C for all test groups with >65% survivors on Day 5. A T/C value of 85% indicates a toxic test. An initial T/C of 125% is considered necessary to demonstrate activity. A reproduced T/C 125% is considered worthy of further study. For confirmed activity a composition should have two multi-dose assays that produce a T/C 125%.

Metastasis after IV Injection of Tumor Cells $10^5$ B16 melanoma cells in 0.3 ml saline are injected intravenously in C57BL/6 mice. The mice are treated intravenously with 1 g of the composition being tested in 0.5 ml saline. Controls receive saline alone. The treatment is given as one dose per week. Mice sacrificed after 4 weeks of therapy, the lungs are removed and metastases are enumerated.

C. 3LL Lewis Lung Carcinoma

Summary:

Tumor may be implanted sc as a 2-4 mm fragment, or im as a $2\times10^6$-cell inoculum. Treatment begins 24 hours after implant or is delayed until a tumor of specified size (usually approximately 400 mg) can be palpated. The composition being tested is administered ip daily for 11 days and the results are expressed as a percentage of the control. Origin of tumor line: arose spontaneously in 1951 as carcinoma of the lung in a C57BL/6 mouse. Cancer Res 15:39, 1955. See, also Malave, I. et al., J. Nat'l. Canc. Inst. 62:83-88 (1979).

| | |
|---|---|
| Animals | One sex used for all test and control animals in one experiment. |
| Propagation Strain | C57BL/6 mice |
| Tumor Transfer | Inject cells im in hind leg or implant fragment sc in axillary region with puncture in inguinal region. Transfer on day 12-14 |
| Testing Strain | BDF1 (C57BL/6 × DBA/2) or C3H mice |
| Time of Transfer | Same as above |
| Weight | Within a 3-g range, minimum weight of 18 g for males and 17 g for females. |
| Exp Size (n) | 6/group for sc implant, or 10/group for im implant.; No. of control groups varies according to number of test groups. |

Testing Schedule

| DAY | PROCEDURE |
|---|---|
| 0 | Implant tumor. Prepare materials. Run positive control in every odd-numbered experiment. Record survivors daily. |
| 1 | Weigh and randomize animals. Begin treatment with therapeutic composition. Typically, mice receive doses of the test composition in 0.5-1 ml saline on schedules as described herein. Controls receive saline alone. Treatment is as described herein. Any surviving mice are sacrificed after 4 wks of therapy. |
| 5 | Weigh animals and record. |
| Final day | Kill all survivors and evaluate experiment. |

Quality Control:

Acceptable im tumor weight on Day 12 is 500-2500 mg. Acceptable im tumor MedST is 18-28 days. Positive control compound is cyclophosphamide: 20 mg/kg/injection, qd, Days 1-11. Check control deaths, no takes, etc.

Evaluation:

Compute mean animal weight when appropriate, and at the completion of testing compute T/C for all test groups. When the parameter is tumor weight, a reproducible T/C of 42% is considered necessary to demonstrate activity. When the parameter is survival time, a reproducible T/C of 125% is considered necessary to demonstrate activity. For confirmed activity a composition must have two multi-dose assays D. 3LL Lewis Lung Carcinoma Metastasis Model This model has been utilized by a number of investigators. See, for example, Gorelik, E. et al., J. Nat'l. Canc. Inst. 65:1257-1264 (1980); Gorelik, E. et al., Rec. Results Canc. Res. 75:20-28 (1980); Isakov, N. et al., Invasion Metas. 2:12-32 (1982) Talmadge J. E. et al., J. Nat'l. Canc. Inst. 69:975-980 (1982); Hilgard, P. et al., Br. J. Cancer 35:78-86(1977)).

Mice:

male C57BL/6 mice, 2-3 months old.

Tumor:

The 3LL Lewis Lung Carcinoma was maintained by sc transfers in C57BL/6 mice. Following sc, im or intra-footpad transplantation, this tumor produces metastases, preferentially in the lungs. Single-cell suspensions are prepared from solid tumors by treating minced tumor tissue with a solution of 0.3% trypsin. Cells are washed 3 times with PBS (pH 7.4) and suspended in PBS. Viability of the 3LL cells prepared in this way is generally about 95-99% (by trypan blue dye exclusion). Viable tumor cells ($3\times10^4$-$5\times10^6$) suspended in 0.05 ml PBS are injected into the right hind foot pads of C57BL/6 mice. The day of tumor appearance and the diameters of established tumors are measured by caliper every two days. Typically, mice receive doses of the composition being tested in doses described herein. Controls receive saline alone. The treatment is given as one or two doses per week.

In experiments involving tumor excision, mice with tumors 8-10 mm in diameter are divided into two groups. In one group, legs with tumors are amputated after ligation above the knee joints. Mice in the second group are left intact as non-amputated tumor-bearing controls. Amputation of a tumor-free leg in a tumor-bearing mouse has no known effect on subsequent metastasis, ruling out possible effects of anesthesia, stress or surgery. Surgery is performed under Nembutal anesthesia (60 mg veterinary Nembutal per kg body weight).

Determination of Metastasis Spread and Growth

Mice are killed 10-14 days after amputation. Lungs are removed and weighed. Lungs are fixed in Bouin's solution and the number of visible metastases is recorded. The diameters of the metastases are also measured using a binocular stereoscope equipped with a micrometer-containing ocular under 8× magnification. On the basis of the recorded diameters, it is possible to calculate the volume of each metastasis. To determine the total volume of metastases per lung, the mean number of visible metastases is multiplied by the mean volume of metastases. To further determine metastatic growth, it is possible to measure incorporation of $^{125I}$dUrd into lung cells (Thakur, M. L. et al., *J. Lab. Clin. Med.* 89:217-228 (1977). Ten days following tumor amputation, 25 mg of $^{125}$IdUrd is inoculated into the peritoneums of tumor-bearing (and, if used, tumor-resected mice. After 30 min, mice are given 1 mCi of $^{125}$IdUrd. One day later, lungs and spleens are removed and weighed, and a degree of $^{125}$IdUrd incorporation is measured using a gamma counter.

Statistics:

Values representing the incidence of metastases and their growth in the lungs of tumor-bearing mice are not normally distributed. Therefore, non-parametric statistics such as the Mann-Whitney U-Test may be used for analysis.

Study of this model by Gorelik et al. (1980, supra) showed that the size of the tumor cell inoculum determined the extent of metastatic growth. The rate of metastasis in the lungs of operated mice was different from primary tumor-bearing mice. Thus in the lungs of mice in which the primary tumor had been induced by inoculation of large doses of 3LL cells ($1-5\times10^6$) followed by surgical removal, the number of metastases was lower than that in nonoperated tumor-bearing mice, though the volume of metastases was higher than in the nonoperated controls. Using $^{125}$IdUrd incorporation as a measure of lung metastasis, no significant differences were found between the lungs of tumor-excised mice and tumor-bearing mice originally inoculated with $10^6$ 3LL cells. Amputation of tumors produced following inoculation of $10^5$ tumor cells dramatically accelerated metastatic growth. These results were in accord with the survival of mice after excision of local tumors. The phenomenon of acceleration of metastatic growth following excision of local tumors had been observed by other investigators. The growth rate and incidence of pulmonary metastasis were highest in mice inoculated with the lowest doses ($3\times10^4$-$10^5$ of tumor cells) and characterized also by the longest latency periods before local tumor appearance. Immunosuppression accelerated metastatic growth, though nonimmunologic mechanisms participate in the control exerted by the local tumor on lung metastasis development. These observations have implications for the prognosis of patients who undergo cancer surgery.

E. Walker Carcinosarcoma 256

Summary:

Tumor may be implanted sc in the axillary region as a 2-6 mm fragment, im in the thigh as a 0.2-ml inoculum of tumor homogenate containing $10^6$ viable cells, or ip as a 0.1-ml suspension containing $10^6$ viable cells. Treatment of the composition being tested is usually ip. Origin of tumor line: arose spontaneously in 1928 in the region of the mammary gland of a pregnant albino rat. *J Natl Cancer Inst* 13:1356, 1953.

| | |
|---|---|
| Animals | One sex used for all test and control animals in one experiment. |
| Propagation Strain | Random-bred albino Sprague-Dawley rats |
| Tumor Transfer | S.C. fragment implant is by trochar or 12-g needle into axillary region with puncture in inguinal area. I.m. implant is with 0.2 ml of tumor homogenate (containing $10^6$ viable cells) into the thigh. I.p. implant is with 0.1 ml suspension (containing $10^6$ viable cells) Day 7 for im or ip implant; Days 11-13 for sc implant |
| Testing Strain | Fischer 344 rats or random-bred albino rats |
| Time of Transfer | Same as above |
| Weight | 50-70 g (maximum of 10-g weight range within each experiment) |
| Exp Size (n) | 6/roup; No. of control groups varies according to number of test groups. |

| Test system | Prepare drug on day: | Administer drug on days: | Weigh animals on days | Evaluate on days |
|---|---|---|---|---|
| 5WA16 | 2 | 3-6 | 3 and 7 | 7 |
| 5WA12 | 0 | 1-5 | 1 and 5 | 10-14 |
| 5WA31 | 0 | 1-9 | 1 and 5 | 30 |

In addition the following general schedule is followed

| DAY | PROCEDURE |
|---|---|
| 0 | Implant tumor. Prepare materials. Run positive control in every odd-numbered experiment. Record survivors daily. |
| 1 | Weigh and randomize animals. Begin treatment with therapeutic composition. Typically, mice receive doses of the test composition in 0.5-1 ml saline on schedules provided herein. Controls receive saline alone. Treatment is as described herein. Any surviving mice are sacrificed after 4 wks of therapy. |
| Final day | Kill all survivors and evaluate experiment. |

Quality Control:

Acceptable i.m. tumor weight or survival time for the above three test systems are: 5WA16: 3-12 g.; 5WA12: 3-12 g.; 5WA31 or 5WA21: 5-9 days.

Evaluation:

Compute mean animal weight when appropriate, and at the completion of testing compute T/C for all test groups. When the parameter is tumor weight, a reproducible T/C 42% is considered necessary to demonstrate activity. When the parameter is survival time, a reproducible T/C 125% is considered necessary to demonstrate activity. For confirmed activity F. A20 Lymphoma $10^6$ murine A20 lymphoma cells in 0.3 ml saline are injected subcutaneously in Balb/c mice. The mice are treated intravenously with 1 g of the composition being tested in 0.5 ml saline. Controls receive saline alone. The treatment is given as one dose per week. Tumor growth is monitored daily by physical measurement of tumor size and calculation of total tumor volume. After 4 weeks of therapy the mice are sacrificed.

Use in Established Tumors

For nucleic acid constructs, treatment consists of doses in $1\times10^{-6}$-$10^{-10}$ PFU as described herein. Unless indicated otherwise above, treatments are given one to three times per week for two to 10 weeks. Doses are administered iv into the tail vein one to three times per week for two to 10 weeks or directly into tumor in 30-75% or the iv doses on the same schedule. The results shown in Table 4 are for each composition and dose tested. The results are statistically significant by the Wilcoxon rank sum test.

TABLE 4

| Tumor Model | Parameter | % of Control Response |
|---|---|---|
| L1210 | MST | >130% |
| P388 | MST | >130% |
| B16 | MST | >130% |
| B16 metastasis | Median number of metastases | <70% |
| 3LL | MST | >130% |
| | Mean tumor weight | <40% |
| 3LL metastasis | MST | >130% |
| | Mean lung weight | <60 |
| | Median number of metastases | <60% |
| | Median volume of metastases | <60% |
| | Medial volume of metastases | <60% |
| | Median uptake of IdUrd | <60% |
| Walker carcinoma | MedST | >130% |
| | Mean tumor weight | <40% |
| A20 | MST | >130% |
| | Mean tumor volume | <40% |

TABLE VII

| RESPONSE | DEFINITION |
|---|---|
| Complete remission (CR) | Disappearance of all evidence of disease |
| Partial remission (PR) | >50% decrease in the product of the two greatest perpendicular tumor diameters; no new lesions |
| Less than partial remission (<PR) | 25-50% decrease in tumor size, stable for at least 1 month |
| Stable disease | <25% reduction in tumor size; no progression or new lesions |
| Progression | >25% increase in size of any one measured lesion or appearance of new lesions despite stabilization or remission of disease in other measured sites |

Results

The efficacy of the therapy in a population is evaluated using conventional statistical methods including, for example, the Chi Square test or Fisher's exact test. Long-term changes in and short term changes in measurements can be evaluated separately.

One hundred and fifty patients are treated. The results are summarized in Table 5. Positive tumor responses are observed in 75-80% of the patients as follows:

TABLE 5

| | All Patients | |
|---|---|---|
| Response | No. | % |
| PR | 20 | 66 |
| <PR | 10 | 33 |
| Tumor Types | Response | % Response |
| Breast Adenocarcinoma | PR + <PR | 80 |
| Gastrointestinal Carcinom | PR + <PR | 75 |
| Lung Carcinoma | PR + <PR | 75 |
| Prostate Carcinoma | PR + <PR | 75 |
| Lymphoma/Leukemia | PR + <PR | 75 |
| Head and Neck Cancer | PR + <PR | 75 |
| Renal and Bladder Cancer | PR + <PR | 75 |
| Melanoma | PR + <PR | 75 |

Example 4

Clinical Trial of Constructs 2, 3 or 4 Administered Parenterally in Human Cancer Patients Constructs 2, 3 or 4 described herein consisting of cDNA extracted from untreated tumor cells (Construct 2), treatment-resistant tumor cells (Construct 3) or normal cells of the same histologic type as the tumor (Construct 4) transduced with VASTA-SAg-costimulatory nucleic acids are tested for therapeutic efficacy in humans cancer patients. All patients treated have histologically confirmed malignant masses confirmed by biopsy or cytology. Malignant diseases including carcinomas, sarcomas, melanomas, gliomas neuroblastomas, lymphomas and leukemia. The malignant disease has failed to respond or is advancing despite conventional therapy. Patients in all stages of malignant disease involving any organ system are included. Staging describes both tumor and host, including organ of origin of the tumor, histologic type, histologic grade, extent of tumor size, site of metastases and functional status of the patient. For a general classification includes the known ranges of Stage 1 (localized disease) to Stage 4 (widespread metastases), see Abraham J et al., *Bethesda Handbook of Clinical Oncology*, Lippincott, Williams & Wilkins, Philadelphia, Pa., 2001. Patient history is obtained and physical examination performed along with conventional tests of cardiovascular and pulmonary function and appropriate radiologic procedures. The malignant masses are visible on x-ray or CT scan and are measurable with calipers. They have not been undergoing any other anticancer treatment for at least one month and have a clinical KPS of at least 50.

These Constructs are administered parenterally preferably intravenously, intrapleurally, intraperitoneally three to five times weekly in doses of $1 \times 10^{-10}$ to $10^{-16}$ PFU/ml for up to 10 weeks. An equally efficacious regimen is alternating injections of TvSAg-costim or TRvSAg-costim or NvSAg-costim every other day for up to 9 weeks.

For intratumoral administration the constructs are in doses of $10^6$-$10^8$ PFU/ml. The tumors are injected under direct vision at surgery, bronchoscopy, endoscopy, peritoneoscopy, culdoscopy. They are accessible to percutaneous injection with CT, ultrasound or stereotaxis used to localize and guide the injected composition into the tumor.

Patient Evaluation:

Assessment of response of the tumor to the therapy is made once per week during therapy and 30 days thereafter using CT or x-ray visualization. Depending on the response to treatment, side effects, and the health status of the patient, treatment is terminated or prolonged from the standard protocol given above. Tumor response criteria are those established by the WHO and RECIST (Response Evaluation Criteria in Solid Tumors) summarized below in Table 6 (also Abraham et al., supra).

TABLE 6

| RESPONSE | DEFINITION |
|---|---|
| Complete remission (CR) | Disappearance of all evidence of disease |
| Partial remission (PR) | ≥50% decrease in the product of the two greatest perpendicular tumor diameters; no new lesions |
| Less than partial remission (<PR) | 25%-50% decrease in tumor size, stable for at least 1 month |
| Stable disease | <25% reduction in tumor size; no progression or new lesions |
| Progression | ≥25% increase in size of any one measured lesion or appearance of new lesions despite stabilization or remission of disease in other measured sites |

The efficacy of the therapy in a patient population is evaluated using conventional statistical methods, including, for example, the Chi Square test or Fisher's exact test. Long-term changes in and short term changes in measurements are evaluated separately.

Results

A total of 810 patients are patients treated. The number of patients for each tumor type and the results of treatment are summarized in Table 7. Positive tumor responses are observed in as high as 80-90%% of the patients with breast, gastrointestinal, lung, prostate, renal and bladder tumors as well as melanoma and neuroblastoma as follows:

Six hundred and sixty five patients with all tumors exhibit objective clinical responses for an overall response rate of 82%. Tumors generally start to diminish and objective remissions are evident after four weeks of combined SEA-chemotherapy. Responses endure for an average of 24 months.

Toxicity consists of mild short-lived fever, fatigue and anorexia not requiring treatment. The incidence of side effects (as % of total treatments) are as follows: chills—10; fever—10; pain—5; nausea—5; respiratory—3; headache—3; tachycardia—2; vomiting—2; hypertension—2; hypotension—2; joint pain—2; rash—2; flushing—1; diarrhea—1; itching/hives—1; bloody nose—1; dizziness—<1; cramps—<1; fatigue—<1; feeling faint—<1; twitching—<1; blurred vision—<1; gastritis<1; redness on hand—<1. Fever and chills are the most common side effects observed. Side effects are somewhat less frequent in patients treated with intratumoral SAg plus low dose single agent chemotherapy compared with SAg and full dose systemic chemotherapy. Side effects are less prevalent with the intratumoral SAg-chemotherapy regimen compared with SAg and full dose systemic chemotherapy regimen but this is not statistically different. CBC, renal and liver functions tests do not change significantly after treatments.

TABLE 7

| | All Patients | |
|---|---|---|
| No. | Response | % of Patients Responding |
| 567 | CR | 76 |
| 70 | PR | 9.6 |
| 28 | <PR | 3.7 |

| By Tumor Type: | No. | Response | % of Patients Responding |
|---|---|---|---|
| Breast adenocarcinoma | 103 | CR + PR + <PR | 87% |
| Gastrointestinal carcinoma | 94 | CR + PR + <PR | 82% |
| Lung Carcinoma | 160 | CR + PR + <PR | 89% |
| Brain glioma/astrocytoma | 46 | CR + PR + <PR | 79% |
| Prostate Carcinoma | 93 | CR + PR + <PR | 78% |
| Lymphoma/Leukemia | 82 | CR + PR + <PR | 75% |
| Head and Neck Cancer | 85 | CR + PR + <PR | 73% |
| Renal and Bladder Cancer | 45 | CR + PR + <PR | 92% |
| Melanoma | 56 | CR + PR + <PR | 84% |
| Neuroblastoma | 58 | CR + PR + <PR | 88% |

Example 5

Clinical Trial of Constructs 2, 3 or 4 Administered Intrapleurally, Intraperitoneally or Intratumorally in Human Cancer Patients Patients have with malignant pleural effusions confirmed by biopsy or pleural fluid cytology and have not been undergoing any other anticancer treatment for at least one month and have a clinical Karnofsky status of at least 60-70%. Constructs are administered in doses of $10^{10}$-$10^{16}$ PFU intrapleurally or intraperitoneally once or twice weekly immediately after drainage of the effusion or ascites via conventional thoracentesis or paracentesis. This procedure is performed once or twice weekly in an outpatient or office setting. Treatment is continued once weekly until effusion or ascites does not recur. An objective response is recognized as no reaccumulation of pleural fluid or ascitic fluid 30 days after treatment (DeCamp M M et al., Chest 112: 291S-295S (1997); Fenton K N et al., Am J. Surg. 170: 69-74 (1995)).

Seventy five patients with malignant pleural effusion treated with intrapleural or constructs. All patients have stage IIIb or stage IV lung cancer. Fifty patients with malignant ascites are treated of whom 27 have ovarian cancer and 23 have gastrointestinal malignancies. of 94.5% and 90% of patients pleural effusion or malignant ascites exhibit objective clinical responses. Patients require an average of three treatments before there a significant reduction is fluid reaccumulation. However, several patients required only one treatment to eliminate fluid reaccumulation.

Toxicity in both malignant pleural effusion and ascites consists of mild short-lived fever, fatigue and anorexia not requiring treatment. CBC, renal and liver functions tests did not change significantly after treatments.

Example 6

Clinical Trial of Constructs 2, 3 or 4 with Chemotherapy in Human Cancer Patients All patients treated have histologically confirmed malignant masses confirmed by biopsy or cytology are entered. Malignant diseases including carcinomas, sarcomas, melanomas, gliomas neuroblastomas, lymphomas and leukemia. The malignant disease has failed to respond or is advancing despite conventional therapy. Patients in all stages of malignant disease involving any organ system are included. Staging describes both tumor and host, including organ of origin of the tumor, histologic type, histologic grade, extent of tumor size, site of metastases and functional status of the patient. For a general classification includes the known ranges of Stage 1 (localized disease) to Stage 4 (widespread metastases), see Abraham J et al., Bethesda Handbook of Clinical Oncology, Lippincott, Williams & Wilkins, Philadelphia, Pa., 2001. Patient history is obtained and physical examination performed along with conventional tests of cardiovascular and pulmonary function and appropriate radiologic procedures. The malignant masses are visible on x-ray or CT scan and are measurable with calipers. They have not been undergoing any other anticancer treatment for at least one month and have a clinical KPS of at least 50.

Construct 1 is administered parenterally in doses three times weekly for up to 10 weeks. Intratumoral injection of tumors is carried out under direct vision at surgery, bronchoscopy, endoscopy, peritoneoscopy, culdocopy. Most are accessible to percutaneous injection using CT, ultrasound or stereotaxis to localize the tumor.

Parenteral chemotherapy preferably comprises the use of a selected single agent which is known in the art to be effective against a particular tumor. Intratumoral combination chemotherapy wherein each agent is given in a reduced dose 3-7 fold below that of the mean recommended dose of a systemic chemotherapeutic agent per cycle.

Recommended mean dosages for systemic administration of single and individual chemotherapeutic agents for human tumors are well known in the art and given in Abraham et al., supra. The chemotherapy may be given before at the same time or after delivery of the construct. Preferably it is given after 3 and up to 10 treatments with the constructs. The chemotherapy may be continued on this basis after every 3 to 10 injections for 3 to 6 months. Systemic chemotherapy is also used in the full recommended therapeutic dose for a single agent alone or in combination with other chemotherapeutic agents.

For intratumoral injection, a typical treatment consists of percutaneous or transbronchial injection of a lung tumor nodule intratumorally with the construct once weekly for 3-7 weeks followed by isplatin in fully doses parenterally every 7 days for three weeks. The chemotherapy is also used alone before construct treatment or together with constructs.

Representative doses of single agent chemotherapeutic agents used in an average sized adult for intratumoral injection against the more common tumors are given in the section on chemotherapy.

Patient Evaluation:

Assessment of response of the tumor to the therapy is made once per week during therapy and 30 days thereafter using CT or x-ray visualization. Depending on the response to treatment, side effects, and the health status of the patient, treatment is terminated or prolonged from the standard protocol given above. Tumor response criteria are those established by the WHO and RECIST (Response Evaluation Criteria in Solid Tumors) summarized below in Table 8 (also Abraham et al., supra).

TABLE 8

| RESPONSE | DEFINITION |
| --- | --- |
| Complete remission (CR) | Disappearance of all evidence of disease |
| Partial remission (PR) | ≥50% decrease in the product of the two greatest perpendicular tumor diameters; no new lesions |
| Less than partial remission (<PR) | 25%-50% decrease in tumor size, stable for at least 1 month |
| Stable disease | <25% reduction in tumor size; no progression or new lesions |
| Progression | ≥25% increase in size of any one measured lesion or appearance of new lesions despite stabilization or remission of disease in other measured sites |

The efficacy of the therapy in a patient population is evaluated using conventional statistical methods, including, for example, the Chi Square test or Fisher's exact test. Long-term changes in and short term changes in measurements are evaluated separately.

Results

A total of 797 patients are treated. The number of patients for each tumor type and the results of treatment are summarized in Table 9. Positive tumor responses are observed in as high as 80-90%% of the patients with breast, gastrointestinal, lung, prostate, renal and bladder tumors as well as melanoma and neuroblastoma as follows:

Six hundred and sixty five patients with all tumors exhibit objective clinical responses for an overall response rate of 82%. Tumors generally start to diminish and objective remissions are evident after four weeks of combined SEA-chemotherapy. Responses endure for an average of 24 months.

Toxicity consists of mild short-lived fever, fatigue and anorexia not requiring treatment. The incidence of side effects (as % of total treatments) are as follows: chills—10; fever—10; pain—5; nausea—5; respiratory—3; headache—3; tachycardia—2; vomiting—2; hypertension—2; hypotension—2; joint pain—2; rash—2; flushing—1; diarrhea—1; itching/hives—1; bloody nose—1; dizziness—<1; cramps—<1; fatigue—<1; feeling faint—<1; twitching—<1; blurred vision—<1; gastritis<1; redness on hand—<1. Fever and chills are the most common side effects observed. CBC, renal and liver functions tests do not change significantly after treatments.

TABLE 9

| All Patients | | |
| --- | --- | --- |
| No. | Response | % of Patients Responding |
| 567 | CR | 70 |
| 80 | PR | 10.1 |
| 47 | <PR | 5.0 |

| By Tumor Type: | No. | Response | % of Patients Responding |
| --- | --- | --- | --- |
| Breast adenocarcinoma | 97 | CR + PR + <PR | 80% |
| Gastrointestinal carcinoma | 98 | CR + PR + <PR | 85% |
| Lung Carcinoma | 145 | CR + PR + <PR | 90% |
| Brain glioma/astrocytoma | 50 | CR + PR + <PR | 80% |
| Prostate Carcinoma | 97 | CR + PR + <PR | 80% |
| Lymphoma/Leukemia | 80 | CR + PR + <PR | 75% |
| Head and Neck Cancer | 80 | CR + PR + <PR | 75% |
| Renal and Bladder Cancer | 50 | CR + PR + <PR | 90% |
| Melanoma | 50 | CR + PR + <PR | 80% |
| Neuroblastoma | 50 | CR + PR + <PR | 80% |

Example 7

Clinical Trial of Sickle Cell or Other Cellular Carriers Transduced with Construct 1

For human studies, SS erythrocytes or nucleated SS erythrocyte precursors infected with Constructs 2, 3, 4. In these Constructs, nucleic acids encoding the SAg include wild type SAgs SAg variants, SAg fragments and SAg fusion proteins such as SAg-tumor specific targeting molecules as described herein. The SS cells are obtained from patients with homozygous S or sickle thalassemia hemoglobin, hemizygous sickle S and A hemoglobin, sickle hemoglobin-C disease, sickle beta plus thalassemia, sickle hemoglobin-D disease, sickle hemoglobin-E disease, homozygous C or C-thalassemia, hemoglobin-C beta plus thalassemia, homozygous E or E-thalassemia. The SS erythrocytes are ABO- and Rh-matched for compatibility with recipients. Mature or progenitor SS cell transfected with VASTA or other suitable vector encoding SAg as described herein are used.

Tumors of any type are susceptible to therapy with these agents. The cells are administered intravenously or intraarterially in a blood vessel perfusing a specific tumor site or organ, e.g. carotid artery, portal vein, femoral artery etc. over the same amount of time required for the infusion of a conventional blood transfusion. The quantity of cells to be administered in any one treatment ranges from one tenth to one half of a full unit of blood. The treatments are generally given every 2-7 days for a total of 1-12 treatments. However, the treatment schedule is flexible and may be given for a longer of shorter duration depending upon the patients' response. A heme oxygenase inhibitor zinc protoporphyrin (0.1-100 µg) is given intravenously 2-24 hours before, together with or 2-24 hours after each SS cell infusion. It may be continued daily for up to 3 days after each infusion. All treated patients have histologically confirmed malignant disease including carcinomas, sarcomas, melanomas, lymphomas and leukemias and have failed conventional therapy. Patients may be diagnosed as having any stage of metastatic disease involving any organ system. Staging describes both tumor and host, including organ of origin of the tumor, histologic type and histologic grade, extent of tumor size, site of metastases and functional status of the patient. A general classification includes the known ranges of Stage I (localized disease) to Stage 4 (widespread metastases). Patient history is obtained and physical examination performed along with conventional tests of cardiovascular and pulmonary function and appropriate radiologic procedures. Histopathology is obtained to verify malignant disease.

Patient Evaluation:

Assessment of response of the tumor to the therapy is made once per week during therapy and 30 days thereafter using CT or x-ray visualization. Depending on the response to treatment, side effects, and the health status of the patient, treatment is terminated or prolonged from the standard protocol given above. Tumor response criteria are those established by the WHO and RECIST (Response Evaluation Criteria in Solid Tumors) summarized below Table 10 (also Abraham et al., supra).

TABLE 10

| RESPONSE | DEFINITION |
| --- | --- |
| Complete remission (CR) | Disappearance of all evidence of disease |
| Partial remission (PR) | >50% decrease in the product of the two greatest perpendicular tumor diameters; no new lesions |
| Less than partial remission (<PR) | 25%-50% decrease in tumor size, stable for at least 1 month |
| Stable disease | <25% reduction in tumor size; no progression or new lesions |
| Progression | ≥25% increase in size of any one measured lesion or appearance of new lesions despite stabilization or remission of disease in other measured sites |

The efficacy of the therapy in a patient population is evaluated using conventional statistical methods, including, for example, the Chi Square test or Fisher's exact test. Long-term changes in and short term changes in measurements are evaluated separately.

Results:

A total of 1178 patients are patients treated, 339 with mature SS cells, 338 with SS progenitor cells. The overall number of patients for each tumor type and the results of treatment are summarized in Table 11. Positive tumor responses are observed in as high as 85-95% of the patients with breast, gastrointestinal, lung, prostate, renal and bladder tumors as well as melanoma and neuroblastoma as follows:

One thousand and forty eight patients entered with all tumors exhibit objective clinical responses for an overall response rate of 89%. Tumors generally start to diminish and objective remissions are evident after four weeks of therapy. Responses endure for a mean of 36 months.

TABLE 11

Results of treatment with SS cells or SS progenitor cells loaded with VASTA opertively linked to Nucleic Acids Encoding SAg & costimulatory Molecules

| Patients/Tumors | | | |
| --- | --- | --- | --- |
| | No. | Response | % of Patients Responding |
| All patients | 1048 | CR + PR | 72.0 |
| Tumor Type | No. | Response | % of Patients Responding |
| Breast adenocarcinoma | 97 | CR + PR + <PR | 78% |
| Gastrointestinal carcinoma | 105 | CR + PR + <PR | 85% |
| Lung Carcinoma | 146 | CR + PR + <PR | 91% |
| Brain glioma/astrocytoma | 61 | CR + PR + <PR | 56% |
| Prostate Carcinoma | 93 | CR + PR + <PR | 92% |
| Lymphoma/Leukemia | 98 | CR + PR + <PR | 89% |
| Head and Neck Cancer | 95 | CR + PR + <PR | 79% |
| Renal and Bladder Cancer | 51 | CR + PR + <PR | 89% |
| Melanoma | 55 | CR + PR + <PR | 85% |
| Neuroblastoma | 57 | CR + PR + <PR | 86% |
| Prostate carcinoma | 93 | CR + PR + <PR | 88% |
| Uterine/Cervical | 101 | CR + PR + <PR | 81% |

Toxicity consists of mild short-lived fever, fatigue and anorexia not requiring treatment. The incidence of side effects (as % of total treatments) are as follows: chills—12; fever—15; pain—6; nausea—3; respiratory—2; headache—2; tachycardia—4; vomiting—4; hypertension—1; hypotension—2; joint pain—3; rash—1; flushing—4; diarrhea—2; itching/hives—1; bloody nose—1; dizziness—<1; cramps—<1; fatigue—<1; feeling faint—<1; twitching—<1; blurred vision—<1; gastritis<1; redness on hand—<1. Fever and chills are the most common side effects observed.

Example 9

Preparation of Tumor Cell/Normal Cells Hybrids

This method is provided in Example 25 of U.S. application Ser. No. 10/428,817 incorporated by reference and of which the instant application is a continuation in part.

All the references, patents and patent applications cited above in this patent application and their references are incorporated by reference in entirety, whether specifically incorporated or not. In addition, the following patent applications and their references are incorporated by reference in their entirety:

| Inventor | Serial No. | Filing Date | Title |
| --- | --- | --- | --- |
| Terman, D. S. | 13/317,590 | Oct. 20, 2011 | Compositions and Methods for Treatment of Cancer |
| Terman, D. S. | 61/462,622 | Feb. 3, 2011 | Compositions and Methods for Treatment of Cancer |
| Terman, D. S. | 13/317,590 | Oct. 20, 2011 | Compositions and Methods for Treatment of Cancer |
| Terman, D. S. | 61/455,592 | Oct. 20, 2010 | Compositions and Methods for Treatment of Cancer |
| Terman, D. S | 12/276,941 | Allowance Jun. 27, 2010 | Compositions and Methods for Treatment of Cancer |
| Terman D. S. | 12/276,941 | Nov 24, 2008 | Compositions and Methods for Treatment of Cancer |
| Terman D. S. | 12/145,949 | Jun. 25, 2008 | Compositions and Methods for Treatment of Cancer |
| Terman D. S. | 10/937,758 | Sep. 8, 2004 | Compositions and Methods for Treatment of Cancer |
| Terman, D. S. | 12/586,532 | Sep. 22, 2009 | Sickled Erythrocytes with Anti-tumor Molecules Induce Tumoricidal Effects |
| Terman, D. S. | 61,215,906 | May 11, 2009 | Sickled Erythrocytes, Nucleated Precursors & Erythroleukemia Cells for Targeted Delivery of Tumoricidal Agents |
| Terman, D. S | 61/211,227 | Mar. 28, 2009 | Sickled Erythrocytes, Nucleated Precursors & Erythroleukemia Cells for Targeted Delivery of Tumoricidal Agents |
| Terman, D. S. | 61/206,338 | Jan. 28, 2009 | Sickled Erythrocytes, Nucleated Precursors & Erythroleukemia Cells for Targeted Delivery of Tumoricidal Agents |

-continued

| Inventor | Serial No. | Filing Date | Title |
|---|---|---|---|
| Terman D. S. | 61/205,776 | Jan. 22, 2009 | Sickled Erythrocytes Induced Tumor Vaso-occlusion and Tumoricidal Effects |
| Terman, D. S. | 61/192,949 | Sep. 22, 2008 | Sickled Erythrocytes, Nucleated Precursors & Erythroleukemia Cells for Targeted Delivery of Oncolytic Viruses, Anti-tumor Proteins, Plasmids, Toxins, Hemolysins and Chemotherapy |
| Terman, D. S. | 61/001,585 | Nov. 1, 2007 | Sickled Erythorcytes, Nucleated Precursors and Erythroleukemia cell for Targeted Delivery of Oncolytic Viruses, Anti-tumor Proteins, siRNAs, Plasmids, Toxins, Hemolysins, Prodrugs and Chemotherapy |
| Terman, D, S, Dewhirst M. W. | PCT/US07/69869 | May 29, 2007 | Sickled Erythrocytes, Nucleated Precursors & Erythroleukemia Cells for Targeted Delivery of Oncolytic Viruses, Anti-tumor Proteins, Plasmids, Toxins, Hemolysins and Chemotherapy |
| Terman, D. S. | 60/842,213 | Sep. 5, 2006 | Sickled Erythrocytes & Nucleated Precursors for Targeted Delivery of Oncolytic Toxins, Viruses, hemolysins and chemotherapy |
| Terman, D. S. | 60/819,551 | Jul. 8, 2006 | Sickled Erythrocytes & Nucleated Precursors for Targeted Delivery of Oncolytic Toxins, Viruses, hemolysins and chemotherapy |
| Terman, D. S. | 60/809,553 | May 30, 2006 | Sickled Erythrocytes & Nucleated Precursors for Targeted Delivery of Oncolytic Toxins, Viruses, hemolysins and chemotherapy |
| Terman, D. S. Bohach, G | 60/799,514 | May 10, 2006 | Synergy of Superantigens, Cytokines and Chemotherapy in Treatment of Malignant Disease |
| Terman, D. S, Etiene, J., Vandenesch, F., Lina, G. Bohach, G. | PCTUS 05/022,638 | Jun. 27, 2005 | Enterotoxin Gene Cluster Superantigens (egc) to Treat Malignant Disease |
| Terman, D. S, Etiene, J., Vandenesch, F., Lina, G. Bohach, G. | 60/583,692 | Jun. 29, 2004 | Enterotoxin Gene Cluster Superantigens (egc) to Treat Malignant Disease |
| Terman, D. S. | 60/665,654 | Mar. 23, 2005 | Enterotoxin Gene Cluster Superantigens (egc) to Treat Malignant Disease |
| Terman, D. S, Etiene, J., Vandenesch, F., Lina, G. Bohach, G. | 60/626,159 | Nov. 6, 2004 | Enterotoxin Gene Cluster Superantigens (egc) to Treat Malignant Disease |
| Terman, D. S | 7,776,822 | Issued Aug. 17, 2010 | Intrathecal and Intrapleural Superantigens to Treat Malignant Disease |
| Terman, D. S. | 60/583,692 | Jun. 29, 2004 | Intrathecal and Intrapleural Superantigens to Treat Malignant Disease |
| Terman, D. S. | 60/550,926 | Mar. 5, 2004 | Intrathecal and Intrapleural Superantigens to Treat Malignant Disease |
| Terman, D. S. | 60/539,863 | Jan. 27, 2004 | Intrathecal and Intrapleural Superantigens to Treat Malignant Disease |
| Terman, D. S. | PCT/US03/14381 | May 8, 2003 | Intrathecal and Intrapleural Superantigens to Treat Malignant Disease |
| Terman, D. S. | 10/428,817 | May 5, 2003 | Composition and Methods for Treatment of Neoplastic Diseases |
| Terman, D. S. | 60/438,686 | Jan. 9, 2003 | Intrathecal and Intrapleural Superantigens to Treat Malignant Disease |
| Terman, D. S. | 60/415,310 | Oct. 1, 2002 | Intrathecal and Intratumoral Superantigens to Treat Malignant Disease. |
| Terman, D. S. | 60/406,750 | Aug. 29, 2002 | Intrathecal Superantigens to Treat Malignant Fluid Accumulation |
| Terman, D. S. | 60/415,400 | Oct. 2, 2002 | Composition and Methods for Treatment of Neoplastic Diseases |
| Terman, D. S. | 60/406,697 | Aug. 28, 2002 | Compositions and Methods for Treatment of Neoplastic Diseases |
| Terman, D. S. | 60/389,366 | Jun. 15, 2002 | Compositions and Methods for Treatment of Neoplastic Diseases |
| Terman, D. S. | 60/378,988 | May 8, 2002 | Compositions and Methods for Treatment of Neoplastic Diseases |
| Terman, D. S. | 09/870,759 | May 30, 2001 | Compositions and Methods for Treatment of Neoplastic Diseases |
| Terman, D. S. | 09/751,708 | Dec. 28, 2000 | Compositions and Methods for Treatment of Neoplastic Diseases |
| Terman, D. S. | 09/640,884 | Aug. 30, 2000 | Compositions and Methods for Treatment of Neoplastic Diseases |
| Terman, D. S. | 60/151,470 | Aug. 30, 1999 | Compositions and Methods for Treatment of Neoplastic Diseases |

This application also incorporates by reference the following patents and currently pending patent applications that disclose inventions of the present inventor alone or with co-inventors.

1. Patent application WO91/US342, "Tumor Killing Effects of Enterotoxins and Related Compounds" filed 17 Jan. 1991, and published as WO 91/10680 on 25 Jul. 1991.
2. U.S. Ser. No. 07/891,718 "Tumor Killing Effects of Enterotoxins and Related Compounds," filed 1 Jun. 1992.
3. U.S. Pat. No. 5,728,388, "Method of Cancer Treatment," issued Mar. 17, 1998.
4. U.S. Ser. No. 08/491,746, "Method of Cancer Treatment," filed 19 Jun. 1995.
5. U.S. Ser. No. 08/898,903 "Method of Cancer Treatment," filed 23 Jul. 1997.
6. U.S. Ser. No. 08/896,933 "Tumor Killing Effects of Enterotoxins and Related Compounds," filed 18 Jul. 1997.
7. U.S. Ser. No. 60/085,506, "Compositions and Methods for Treatment of Cancer," filed 5 May 1998.
8. U.S. Ser. No. 60/094,952 "Compositions and Methods for Treatment of Cancer" filed 31 Jul. 1998.
9. U.S. Ser. No. 60/033,172 "Superantigen-Based Methods and Compositions for Treatment of Cancer," filed 17 Dec. 1996.
10. U.S. Ser. No. 60/044,074 "Superantigen-Based Methods and Compositions for Treatment of Cancer," filed 17 Apr. 1997.
11. U.S. Ser. No. 09/061,334 "Tumor Cells with Increased Immunogenicity and Uses Thereof," filed 17 Apr. 1998.

Having now fully described this invention, it will be appreciated by those skilled in the art that the same can be performed within a wide range of equivalent parameters, concentrations, and conditions without departing from the spirit and scope of the invention and without undue experimentation.

The invention claimed is:

1. A method of treating a subject with a tumor comprising the steps of:
    (i) transducing a normal cell or a tumor cell of the same histologic type as said normal cell or a treatment resistant tumor cell of the same histologic type as said tumor cell with a virus or its genomic DNA, wherein said virus or said genomic DNA is operatively linked to nucleic acids encoding a superantigen, and
    (ii) extracting the DNA individually from each transduced tumor cell or normal cell or treatment resistant tumor cell encoding the superantigen and at least one self or tumor protein that has been altered in expression level or structure by the said virus or said superantigen, and (iii) incorporating less than 4000 base pairs of said individually extracted DNA into said virus or its genomic DNA, and (iv) administering to said subject parenterally by infusion or injection a tumoricidally effective amount of at least one of said viruses or said genomic DNA from at least one of said viruses, wherein said virus incorporates said extracted DNA and said genomic DNA incorporates said extracted DNA.

2. The method according to claim 1 wherein the nucleic acids encoding the superantigen consists of:

(i) a native staphylococcal enterotoxin protein which native protein:
  (a) has the biological activity of stimulating T cell mitogenesis via a T cell receptor vβ region; or (ii) a biologically active homologue or fragment of a native staphylococcal enterotoxin which homologue or fragment:
  (a) has the biological activity of stimulating T cell mitogenesis via a T cell receptor vβ region and
  (b) has sequence homology characterized as a z value exceeding 13 when the sequence of the homologue or said fragment is compared to the sequence of a native staphylococcal enterotoxin or a native streptococcal pyrogenic exotoxin, determined by FASTA analysis using gap penalties of −12 and −2, Blosum 50 matrix and Swiss-PROT or PIR database.

3. The method according to claim 1 wherein said virus or its genomic DNA is vesicular stomatitis virus.

4. The method according to claim 1 wherein the said transduced treatment resistant tumor cell is resistant to previous chemotherapy.

5. The method of claim 1 wherein said transduced normal cell, tumor cell or treatment resistant tumor cell is autologous to the subject being treated.

6. The method of claim 1, wherein at least two of said viruses or said genomic DNA from the two of said viruses are administered to the patient.

7. The method of claim 1, wherein three of said viruses or said genomic DNA from the three of said viruses are administered to the patient.

* * * * *

SEQUENCE LISTING

<160> NUMBER OF SEQ ID NOS: 40

<210> SEQ ID NO 1
<211> LENGTH: 231
<212> TYPE: PRT
<213> ORGANISM: Staphylococcus sp.

<400> SEQUENCE: 1

Ser Glu Lys Ser Glu Glu Ile Asn Glu Lys Asp Leu Arg Lys Lys Ser
1               5                   10                  15

Glu Leu Gln Gly Thr Ala Gly Asn Lys Gln Ile Tyr Tyr Tyr Asn Glu
            20                  25                  30

Lys Ala Lys Thr Glu Asn Lys Glu Ser His Asp Gln Phe Leu Gln His
        35                  40                  45

Thr Ile Leu Phe Lys Gly Phe Phe Thr Asp His Ser Trp Tyr Asn Asp
    50                  55                  60

Leu Leu Val Asp Phe Asp Ser Lys Asp Ile Val Asp Lys Tyr Lys Gly
65                  70                  75                  80

Lys Lys Val Asp Leu Tyr Gly Ala Tyr Tyr Gly Tyr Gln Cys Ala Gly
                85                  90                  95

Gly Thr Pro Asn Lys Thr Ala Cys Met Tyr Gly Gly Val Thr Leu His
            100                 105                 110

Asp Asn Asn Arg Leu Thr Glu Gly Lys Lys Val Pro Ile Asn Leu Trp
        115                 120                 125

Leu Asp Gly Lys Gln Asn Thr Val Pro Leu Glu Thr Val Lys Thr Asn
    130                 135                 140

Lys Lys Asn Val Thr Val Gln Glu Leu Asp Leu Gln Ala Arg Arg Tyr
145                 150                 155                 160

Leu Gln Glu Lys Tyr Asn Leu Tyr Asn Ser Asp Val Phe Asp Gly Lys
                165                 170                 175

Val Gln Arg Gly Leu Ile Val Phe His Thr Ser Thr Glu Pro Ser Val
            180                 185                 190

Asn Tyr Asp Leu Phe Gly Ala Gln Gly Gln Tyr Ser Asn Thr Leu Leu
        195                 200                 205

Arg Ile Tyr Arg Asp Asn Lys Ser Ile Asn Ser Glu Asn Met His Ile
    210                 215                 220

Asp Ile Tyr Leu Tyr Thr Ser
225                 230

<210> SEQ ID NO 2
<211> LENGTH: 238
<212> TYPE: PRT
<213> ORGANISM: Staphylococcus sp.

<400> SEQUENCE: 2

Glu Ser Gln Pro Asp Pro Lys Pro Asp Glu Leu His Lys Ser Ser Lys
1               5                   10                  15

Phe Thr Gly Leu Met Glu Asn Met Lys Val Leu Tyr Asp Asp Asn His
            20                  25                  30

Val Ser Ala Ile Asn Val Lys Ser Ile Asp Gln Phe Leu Tyr Phe Asp
        35                  40                  45

Leu Ile Tyr Ser Ile Lys Asp Thr Lys Leu Gly Asn Tyr Asp Asn Val
    50                  55                  60

Arg Val Glu Phe Lys Asn Lys Asp Leu Ala Asp Lys Tyr Lys Asp Lys
65                  70                  75                  80

Tyr Val Asp Val Phe Gly Ala Asn Tyr Tyr Tyr Gln Cys Tyr Phe Ser

```
                        85                  90                  95
Lys Lys Thr Asn Asp Ile Asn Ser His Gln Thr Asp Lys Arg Lys Thr
                100                 105                 110

Cys Met Tyr Gly Gly Val Thr Glu His Asn Gly Asn Gln Leu Asp Lys
                115                 120                 125

Tyr Arg Ser Ile Thr Val Arg Val Phe Glu Asp Gly Lys Asn Leu Leu
                130                 135                 140

Ser Phe Asp Val Gln Thr Asn Lys Lys Val Thr Ala Gln Glu Leu
145                 150                 155                 160

Asp Tyr Leu Thr Arg His Tyr Leu Val Lys Asn Lys Leu Tyr Glu
                    165                 170                 175

Phe Asn Asn Ser Pro Tyr Glu Thr Gly Tyr Ile Lys Phe Ile Glu Asn
                180                 185                 190

Glu Asn Ser Phe Trp Tyr Asp Met Met Pro Ala Pro Gly Asp Lys Phe
                195                 200                 205

Asp Gln Ser Lys Tyr Leu Met Met Tyr Asn Asp Asn Lys Met Val Asp
                210                 215                 220

Ser Lys Asp Val Lys Ile Glu Val Tyr Leu Thr Thr Lys Lys
225                 230                 235
```

<210> SEQ ID NO 3
<211> LENGTH: 240
<212> TYPE: PRT
<213> ORGANISM: Staphylococcus sp.

<400> SEQUENCE: 3

```
Met Asn Lys Ser Arg Phe Ile Ser Cys Val Ile Leu Ile Phe Ala Leu
1               5                   10                  15

Ile Leu Val Leu Phe Thr Pro Asn Val Leu Ala Glu Ser Gln Pro Asp
                20                  25                  30

Pro Thr Pro Asp Glu Leu His Lys Ala Ser Lys Phe Thr Gly Leu Met
                35                  40                  45

Glu Asn Met Lys Val Leu Tyr Asp Asp His Tyr Val Ser Ala Thr Lys
50                  55                  60

Val Lys Ser Val Asp Lys Phe Leu Ala His Asp Leu Ile Tyr Asn Ile
65                  70                  75                  80

Ser Asp Lys Lys Leu Lys Asn Tyr Asp Lys Val Lys Thr Glu Leu Leu
                85                  90                  95

Asn Glu Gly Leu Ala Lys Lys Tyr Lys Asp Glu Val Val Asp Val Tyr
                100                 105                 110

Gly Ser Asn Tyr Tyr Val Asn Cys Tyr Phe Ser Ser Lys Asp Asn Val
                115                 120                 125

Gly Lys Val Thr Gly Gly Lys Thr Cys Met Tyr Gly Gly Ile Thr Lys
                130                 135                 140

His Glu Gly Asn His Phe Asp Asn Gly Asn Leu Gln Asn Val Leu Ile
145                 150                 155                 160

Arg Val Tyr Glu Asn Lys Arg Asn Thr Ile Ser Phe Glu Val Gln Thr
                    165                 170                 175

Asp Lys Lys Ser Val Thr Ala Gln Glu Leu Asp Ile Lys Ala Arg Asn
                180                 185                 190

Phe Leu Ile Asn Lys Lys Asn Leu Tyr Glu Phe Asn Ser Ser Pro Tyr
                195                 200                 205

Glu Thr Gly Tyr Ile Lys Phe Ile Glu Asn Asn Gly Asn Thr Phe Trp
                210                 215                 220
```

Tyr Asp Met Met Pro Ala Pro Gly Asp Lys Phe Asp Gln Ser Lys Tyr
225                 230                 235                 240

<210> SEQ ID NO 4
<211> LENGTH: 239
<212> TYPE: PRT
<213> ORGANISM: Staphylococcus sp.

<400> SEQUENCE: 4

Glu Ser Gln Pro Asp Pro Thr Pro Asp Glu Leu His Lys Ser Ser Glu
1               5                   10                  15

Phe Thr Gly Thr Met Gly Asn Met Lys Tyr Leu Tyr Asp Asp His Tyr
            20                  25                  30

Val Ser Ala Thr Lys Val Met Ser Val Asp Lys Phe Leu Ala His Asp
        35                  40                  45

Leu Ile Tyr Asn Ile Ser Asp Lys Lys Leu Lys Asn Tyr Asp Lys Val
    50                  55                  60

Lys Thr Glu Leu Leu Asn Glu Asp Leu Ala Lys Lys Tyr Lys Asp Glu
65                  70                  75                  80

Val Val Asp Val Tyr Gly Ser Asn Tyr Val Asn Cys Tyr Phe Ser
                    85                  90                  95

Ser Lys Asp Asn Val Gly Lys Val Thr Gly Lys Thr Cys Met Tyr
                100                 105                 110

Gly Gly Ile Thr Lys His Glu Gly Asn His Phe Asp Asn Gly Asn Leu
            115                 120                 125

Gln Asn Val Leu Ile Arg Val Tyr Glu Asn Lys Arg Asn Thr Ile Ser
    130                 135                 140

Phe Glu Val Gln Thr Asp Lys Lys Ser Val Thr Ala Gln Glu Leu Asp
145                 150                 155                 160

Ile Lys Ala Arg Asn Phe Leu Ile Asn Lys Lys Asn Leu Tyr Glu Phe
                165                 170                 175

Asn Ser Ser Pro Tyr Glu Thr Gly Tyr Ile Lys Phe Ile Glu Asn Asn
            180                 185                 190

Gly Asn Thr Phe Trp Tyr Asp Met Met Pro Ala Pro Gly Asp Lys Phe
        195                 200                 205

Asp Gln Ser Lys Tyr Leu Met Met Tyr Asn Asp Asn Lys Thr Val Asp
    210                 215                 220

Ser Lys Ser Val Lys Ile Glu Val His Leu Thr Thr Lys Asn Gly
225                 230                 235

<210> SEQ ID NO 5
<211> LENGTH: 266
<212> TYPE: PRT
<213> ORGANISM: Staphylococcus sp.

<400> SEQUENCE: 5

Met Tyr Lys Arg Leu Phe Ile Ser Arg Val Ile Leu Ile Phe Ala Leu
1               5                   10                  15

Ile Leu Val Ile Ser Thr Pro Asn Val Leu Ala Glu Ser Gln Pro Asp
            20                  25                  30

Pro Met Pro Asp Asp Leu His Lys Ser Ser Glu Phe Thr Gly Thr Met
        35                  40                  45

Gly Asn Met Lys Tyr Leu Tyr Asp Asp His Tyr Val Ser Ala Thr Lys
    50                  55                  60

Val Lys Ser Val Asp Lys Phe Leu Ala His Asp Leu Ile Tyr Asn Ile
65                  70                  75                  80

```
Ser Asp Lys Lys Leu Lys Asn Tyr Asp Lys Val Lys Thr Glu Leu Leu
                85                  90                  95

Asn Glu Asp Leu Ala Lys Tyr Lys Asp Glu Val Val Asp Val Tyr
            100                 105                 110

Gly Ser Asn Tyr Tyr Val Asn Cys Tyr Phe Ser Ser Lys Asp Asn Val
            115                 120                 125

Gly Lys Val Thr Gly Gly Lys Thr Cys Met Tyr Gly Gly Ile Thr Lys
            130                 135             140

His Glu Gly Asn His Phe Asp Asn Gly Asn Leu Gln Asn Val Leu Val
145                 150                 155                 160

Arg Val Tyr Glu Asn Lys Arg Asn Thr Ile Ser Phe Glu Val Gln Thr
                165                 170                 175

Asp Lys Lys Ser Val Thr Ala Gln Glu Leu Asp Ile Lys Ala Arg Asn
            180                 185                 190

Phe Leu Ile Asn Lys Lys Asn Leu Tyr Glu Phe Asn Ser Ser Pro Tyr
            195                 200                 205

Glu Thr Gly Tyr Ile Lys Phe Ile Glu Asn Asn Gly Asn Thr Phe Trp
            210                 215                 220

Tyr Asp Met Met Pro Ala Pro Gly Asp Lys Phe Asp Gln Ser Lys Tyr
225                 230                 235                 240

Leu Met Met Tyr Asn Asp Asn Lys Thr Val Asp Ser Lys Ser Val Lys
                245                 250                 255

Ile Glu Val His Leu Thr Thr Lys Asn Gly
            260                 265
```

<210> SEQ ID NO 6
<211> LENGTH: 258
<212> TYPE: PRT
<213> ORGANISM: Staphylococcus sp.

<400> SEQUENCE: 6

```
Met Lys Lys Phe Asn Ile Leu Ile Ala Leu Leu Phe Phe Thr Ser Leu
1               5                   10                  15

Val Ile Ser Pro Leu Asn Val Lys Ala Asn Glu Asn Ile Asp Ser Val
            20                  25                  30

Lys Glu Lys Glu Leu His Lys Lys Ser Glu Leu Ser Ser Thr Ala Leu
            35                  40                  45

Asn Asn Met Lys His Ser Tyr Ala Asp Lys Asn Pro Ile Ile Gly Glu
            50                  55                  60

Asn Lys Ser Thr Gly Asp Gln Phe Leu Glu Asn Thr Leu Leu Tyr Lys
65                  70                  75                  80

Lys Phe Phe Thr Asp Leu Ile Asn Phe Glu Asp Leu Leu Ile Asn Phe
                85                  90                  95

Asn Ser Lys Glu Met Ala Gln His Phe Lys Ser Lys Asn Val Asp Val
            100                 105                 110

Tyr Pro Ile Arg Tyr Ser Ile Asn Cys Tyr Gly Gly Glu Ile Asp Arg
            115                 120                 125

Thr Ala Cys Thr Tyr Gly Gly Val Thr Pro His Glu Gly Asn Lys Leu
            130                 135                 140

Lys Glu Arg Lys Lys Ile Pro Ile Asn Leu Trp Ile Asn Gly Val Gln
145                 150                 155                 160

Lys Glu Val Ser Leu Asp Lys Val Gln Thr Asp Lys Lys Asn Val Thr
                165                 170                 175

Val Gln Glu Leu Asp Ala Gln Ala Arg Arg Tyr Leu Gln Lys Asp Leu
            180                 185                 190
```

-continued

```
Lys Leu Tyr Asn Asn Asp Thr Leu Gly Gly Lys Ile Gln Arg Gly Lys
            195                 200                 205

Ile Glu Phe Asp Ser Ser Asp Gly Ser Lys Val Ser Tyr Asp Leu Phe
        210                 215                 220

Asp Val Lys Gly Asp Phe Pro Glu Lys Gln Leu Arg Ile Tyr Ser Asp
225                 230                 235                 240

Asn Lys Thr Leu Ser Thr Glu His Leu His Ile Asp Ile Tyr Leu Tyr
            245                 250                 255

Glu Lys

<210> SEQ ID NO 7
<211> LENGTH: 257
<212> TYPE: PRT
<213> ORGANISM: Staphylococcus sp.

<400> SEQUENCE: 7

Met Lys Lys Thr Ala Phe Ile Leu Leu Leu Phe Ile Ala Leu Thr Leu
1               5                   10                  15

Thr Thr Ser Pro Leu Val Asn Gly Ser Glu Lys Ser Glu Glu Ile Asn
            20                  25                  30

Glu Lys Asp Leu Arg Lys Lys Ser Glu Leu Gln Arg Asn Ala Leu Ser
        35                  40                  45

Asn Leu Arg Gln Ile Tyr Tyr Tyr Asn Glu Lys Ala Ile Thr Glu Asn
    50                  55                  60

Lys Glu Ser Asp Asp Gln Phe Leu Glu Asn Thr Leu Leu Phe Lys Gly
65                  70                  75                  80

Phe Phe Thr Gly His Pro Trp Tyr Asn Asp Leu Leu Val Asp Leu Gly
                85                  90                  95

Ser Lys Asp Ala Thr Asn Lys Tyr Lys Gly Lys Val Asp Leu Tyr
            100                 105                 110

Gly Ala Tyr Tyr Gly Tyr Gln Cys Ala Gly Gly Thr Pro Asn Lys Thr
        115                 120                 125

Ala Cys Met Tyr Gly Gly Val Thr Leu His Asp Asn Asn Arg Leu Thr
    130                 135                 140

Glu Glu Lys Lys Val Pro Ile Asn Leu Trp Ile Asp Gly Lys Gln Thr
145                 150                 155                 160

Thr Val Pro Ile Asp Lys Val Lys Thr Ser Lys Lys Glu Val Thr Val
                165                 170                 175

Gln Glu Leu Asp Leu Gln Ala Arg His Tyr Leu His Gly Lys Phe Gly
            180                 185                 190

Leu Tyr Asn Ser Asp Ser Phe Gly Gly Lys Val Gln Arg Gly Leu Ile
        195                 200                 205

Val Phe His Ser Ser Glu Gly Ser Thr Val Ser Tyr Asp Leu Phe Asp
    210                 215                 220

Ala Gln Gly Gln Tyr Pro Asp Thr Leu Leu Arg Ile Tyr Arg Asp Asn
225                 230                 235                 240

Lys Thr Ile Asn Ser Glu Asn Leu His Ile Asp Leu Tyr Leu Tyr Thr
                245                 250                 255

Thr

<210> SEQ ID NO 8
<211> LENGTH: 234
<212> TYPE: PRT
<213> ORGANISM: Staphylococcus sp.
```

```
<400> SEQUENCE: 8

Met Asn Lys Lys Leu Leu Met Asn Phe Phe Ile Val Ser Pro Leu Leu
1               5                   10                  15

Leu Ala Thr Thr Ala Thr Asp Phe Thr Pro Val Pro Leu Ser Ser Asn
            20                  25                  30

Gln Ile Ile Lys Thr Ala Lys Ala Ser Thr Asn Asp Asn Ile Lys Asp
        35                  40                  45

Leu Leu Asp Trp Tyr Ser Ser Gly Ser Asp Thr Phe Thr Asn Ser Glu
    50                  55                  60

Val Leu Asp Asn Ser Leu Gly Ser Met Arg Ile Lys Asn Thr Asp Gly
65                  70                  75                  80

Ser Ile Ser Leu Ile Ile Phe Pro Ser Pro Tyr Tyr Ser Pro Ala Phe
                85                  90                  95

Thr Lys Gly Glu Lys Val Asp Leu Asn Thr Lys Arg Thr Lys Lys Ser
            100                 105                 110

Gln His Thr Ser Glu Gly Thr Tyr Ile His Phe Gln Ile Ser Gly Val
        115                 120                 125

Thr Asn Thr Glu Lys Leu Pro Thr Pro Ile Glu Leu Pro Leu Lys Val
    130                 135                 140

Lys Val His Gly Lys Asp Ser Pro Leu Lys Tyr Gly Pro Lys Phe Asp
145                 150                 155                 160

Lys Lys Gln Leu Ala Ile Ser Thr Leu Asp Phe Glu Ile Arg His Gln
                165                 170                 175

Leu Thr Gln Ile His Gly Leu Tyr Arg Ser Asp Lys Thr Gly Gly
            180                 185                 190

Tyr Trp Lys Ile Thr Met Asn Asp Gly Ser Thr Tyr Gln Ser Asp Leu
        195                 200                 205

Ser Lys Lys Phe Glu Tyr Asn Thr Glu Lys Pro Pro Ile Asn Ile Asp
    210                 215                 220

Glu Ile Lys Thr Ile Glu Ala Glu Ile Asn
225                 230

<210> SEQ ID NO 9
<211> LENGTH: 242
<212> TYPE: PRT
<213> ORGANISM: Staphylococcus sp.

<400> SEQUENCE: 9

Met Asn Lys Ile Phe Arg Val Leu Thr Val Ser Leu Phe Phe Phe Thr
1               5                   10                  15

Phe Leu Ile Lys Asn Asn Leu Ala Tyr Ala Asp Val Gly Val Ile Asn
            20                  25                  30

Leu Arg Asn Phe Tyr Ala Asn Tyr Gln Pro Glu Lys Leu Gln Gly Val
        35                  40                  45

Ser Ser Gly Asn Phe Ser Thr Ser His Gln Leu Glu Tyr Ile Asp Gly
    50                  55                  60

Lys Tyr Thr Leu Tyr Ser Gln Phe His Asn Glu Tyr Glu Ala Lys Arg
65                  70                  75                  80

Leu Lys Asp His Lys Val Asp Ile Phe Gly Ile Ser Tyr Ser Gly Leu
                85                  90                  95

Cys Asn Thr Lys Tyr Met Tyr Gly Gly Ile Thr Leu Ala Asn Gln Asn
            100                 105                 110

Leu Asp Lys Pro Arg Asn Ile Pro Ile Asn Leu Trp Val Asn Gly Lys
        115                 120                 125
```

```
Gln Asn Thr Ile Ser Thr Asp Lys Val Ser Thr Gln Lys Lys Glu Val
    130                 135                 140

Thr Ala Gln Glu Ile Asp Ile Lys Leu Arg Lys Tyr Leu Gln Asn Glu
145                 150                 155                 160

Tyr Asn Ile Tyr Gly Phe Asn Lys Thr Lys Lys Gly Gln Glu Tyr Gly
                165                 170                 175

Tyr Lys Ser Lys Phe Asn Ser Gly Phe Asn Lys Gly Lys Ile Thr Phe
                180                 185                 190

His Leu Asn Asn Glu Pro Ser Phe Thr Tyr Asp Leu Phe Tyr Thr Gly
                195                 200                 205

Thr Gly Gln Ala Glu Ser Phe Leu Lys Ile Tyr Asn Asp Asn Lys Thr
    210                 215                 220

Ile Asp Ala Glu Asn Phe His Leu Asp Val Glu Ile Ser Tyr Glu Lys
225                 230                 235                 240

Thr Glu

<210> SEQ ID NO 10
<211> LENGTH: 258
<212> TYPE: PRT
<213> ORGANISM: Staphylococcus sp.

<400> SEQUENCE: 10

Met Lys Lys Leu Ser Thr Val Ile Ile Ile Leu Ile Leu Glu Ile Val
1               5                   10                  15

Phe His Asn Met Asn Tyr Val Asn Ala Gln Pro Asp Leu Lys Leu Asp
                20                  25                  30

Glu Leu Asn Lys Val Ser Asp Lys Asn Asn Lys Gly Thr Met Gly Asn
            35                  40                  45

Val Met Asn Leu Tyr Thr Ser Pro Pro Val Glu Gly Arg Gly Val Ile
    50                  55                  60

Asn Ser Arg Gln Phe Leu Ser His Asp Leu Ile Phe Pro Ile Glu Tyr
65                  70                  75                  80

Lys Ser Tyr Asn Glu Val Lys Thr Glu Leu Glu Leu Glu Asn Thr Glu
                85                  90                  95

Leu Ala Asn Tyr Lys Asp Lys Lys Val Asp Ile Phe Gly Val Pro
            100                 105                 110

Tyr Phe Tyr Thr Cys Ile Ile Pro Lys Ser Glu Pro Asp Ile Asn Gln
        115                 120                 125

Asn Phe Gly Gly Cys Cys Met Tyr Gly Gly Leu Thr Phe Asn Ser Ser
    130                 135                 140

Glu Asn Glu Arg Asp Lys Leu Ile Tyr Val Gln Val Thr Ile Asp Asn
145                 150                 155                 160

Arg Gln Ser Leu Gly Phe Thr Ile Thr Thr Asn Lys Asn Met Val Thr
                165                 170                 175

Ile Gln Glu Leu Asp Tyr Lys Ala Arg His Trp Thr Lys Glu Lys Lys
            180                 185                 190

Leu Tyr Glu Phe Asp Gly Ser Ala Phe Glu Ser Gly Tyr Ile Lys Phe
        195                 200                 205

Thr Glu Lys Asn Asn Thr Ser Phe Trp Phe Asp Leu Phe Pro Lys Lys
    210                 215                 220

Glu Leu Val Pro Phe Val Pro Tyr Lys Phe Leu Asn Ile Tyr Gly Asp
225                 230                 235                 240

Asn Lys Val Val Asp Ser Lys Ser Ile Lys Met Glu Val Phe Leu Asn
                245                 250                 255
```

Thr His

<210> SEQ ID NO 11
<211> LENGTH: 217
<212> TYPE: PRT
<213> ORGANISM: Staphylococcus sp.

<400> SEQUENCE: 11

```
Glu Asp Leu His Asp Lys Ser Glu Leu Thr Asp Leu Ala Leu Ala Asn
1               5                   10                  15

Ala Tyr Gly Gln Tyr Asn His Pro Phe Ile Lys Glu Asn Ile Lys Ser
            20                  25                  30

Asp Glu Ile Ser Gly Glu Lys Asp Leu Ile Phe Arg Asn Gln Gly Asp
        35                  40                  45

Ser Gly Asn Asp Leu Arg Val Lys Phe Ala Thr Ala Asp Leu Ala Gln
    50                  55                  60

Lys Phe Lys Asn Lys Asn Val Asp Ile Tyr Gly Ala Ser Phe Tyr Tyr
65                  70                  75                  80

Lys Cys Glu Lys Ile Ser Glu Asn Ile Ser Glu Cys Leu Tyr Gly Gly
                85                  90                  95

Thr Thr Leu Asn Ser Glu Lys Leu Ala Gln Glu Arg Val Ile Gly Ala
            100                 105                 110

Asn Val Trp Val Asp Gly Ile Gln Lys Glu Thr Glu Leu Ile Arg Thr
        115                 120                 125

Asn Lys Lys Asn Val Thr Leu Gln Glu Leu Asp Ile Lys Ile Arg Lys
    130                 135                 140

Ile Leu Ser Asp Lys Tyr Lys Ile Tyr Tyr Lys Asp Ser Glu Ile Ser
145                 150                 155                 160

Lys Gly Leu Ile Glu Phe Asp Met Lys Thr Pro Arg Asp Tyr Ser Phe
                165                 170                 175

Asp Ile Tyr Asp Leu Lys Gly Glu Asn Asp Tyr Glu Ile Asp Lys Ile
            180                 185                 190

Tyr Glu Asp Asn Lys Thr Leu Lys Ser Asp Asp Ile Ser His Ile Asp
        195                 200                 205

Val Asn Leu Tyr Thr Lys Lys Val
    210                 215
```

<210> SEQ ID NO 12
<211> LENGTH: 242
<212> TYPE: PRT
<213> ORGANISM: Staphylococcus sp.

<400> SEQUENCE: 12

```
Met Lys Lys Phe Lys Tyr Ser Phe Ile Leu Val Phe Ile Leu Leu Phe
1               5                   10                  15

Asn Ile Lys Asp Leu Thr Tyr Ala Gln Gly Asp Ile Gly Val Gly Asn
            20                  25                  30

Leu Arg Asn Phe Tyr Thr Lys His Asp Tyr Ile Asp Leu Lys Gly Val
        35                  40                  45

Thr Asp Lys Asn Leu Pro Ile Ala Asn Gln Leu Glu Phe Ser Thr Gly
    50                  55                  60

Thr Asn Asp Leu Ile Ser Glu Ser Asn Asn Trp Asp Glu Ile Ser Lys
65                  70                  75                  80

Phe Lys Gly Lys Lys Leu Asp Ile Phe Gly Ile Asp Tyr Asn Gly Pro
                85                  90                  95

Cys Lys Ser Lys Tyr Met Tyr Gly Gly Ala Thr Leu Ser Gly Gln Tyr
```

```
            100                 105                 110
Leu Asn Ser Ala Arg Lys Ile Pro Ile Asn Leu Trp Val Asn Gly Lys
            115                 120                 125

His Lys Thr Ile Ser Thr Asp Lys Ile Ala Thr Asn Lys Lys Leu Val
            130                 135                 140

Thr Ala Gln Glu Ile Asp Val Lys Leu Arg Arg Tyr Leu Gln Glu Glu
145                 150                 155                 160

Tyr Asn Ile Tyr Gly His Asn Asn Thr Gly Lys Gly Lys Glu Tyr Gly
                    165                 170                 175

Tyr Lys Ser Lys Phe Tyr Ser Gly Phe Asn Asn Gly Lys Val Leu Phe
                180                 185                 190

His Leu Asn Asn Glu Lys Ser Phe Ser Tyr Asp Leu Phe Tyr Thr Gly
            195                 200                 205

Asp Gly Leu Pro Val Ser Phe Leu Lys Ile Tyr Glu Asp Asn Lys Ile
            210                 215                 220

Ile Glu Ser Glu Lys Phe His Leu Asp Val Glu Ile Ser Tyr Val Asp
225                 230                 235                 240

Ser Asn

<210> SEQ ID NO 13
<211> LENGTH: 268
<212> TYPE: PRT
<213> ORGANISM: Staphylococcus sp.

<400> SEQUENCE: 13

Met Lys Lys Thr Ile Phe Ile Leu Ile Phe Ser Leu Thr Leu Thr Leu
1               5                   10                  15

Leu Ile Thr Pro Leu Val Tyr Ser Asp Ser Lys Asn Glu Thr Ile Lys
            20                  25                  30

Glu Lys Asn Leu His Lys Lys Ser Glu Leu Ser Ser Ile Thr Leu Asn
        35                  40                  45

Asn Leu Arg His Ile Tyr Phe Phe Asn Glu Lys Gly Ile Ser Glu Lys
    50                  55                  60

Ile Met Thr Glu Asp Gln Phe Leu Asp Tyr Thr Leu Leu Phe Lys Ser
65                  70                  75                  80

Phe Phe Ile Ser His Ser Gln Tyr Asn Asp Leu Leu Val Gln Phe Asp
                85                  90                  95

Ser Lys Glu Thr Val Asn Lys Phe Lys Gly Lys Gln Val Asp Leu Tyr
            100                 105                 110

Gly Ser Tyr Tyr Gly Phe Gln Cys Ser Gly Gly Lys Pro Asn Lys Thr
        115                 120                 125

Ala Cys Met Tyr Gly Gly Val Thr Leu His Glu Asn Asn Gln Leu Tyr
    130                 135                 140

Asp Thr Lys Lys Ile Pro Ile Asn Leu Trp Ile Asp Ser Ile Arg Thr
145                 150                 155                 160

Val Val Pro Leu Asp Ile Val Lys Thr Asn Lys Lys Val Thr Ile
                165                 170                 175

Gln Glu Leu Asp Leu Gln Ala Arg Tyr Tyr Leu His Lys Gln Tyr Asn
            180                 185                 190

Leu Tyr Asn Pro Ser Thr Phe Asp Gly Lys Ile Gln Lys Gly Leu Ile
        195                 200                 205

Val Phe His Thr Ser Lys Glu Pro Leu Val Ser Tyr Asp Leu Phe Asn
    210                 215                 220

Val Ile Gly Gln Tyr Pro Asp Lys Leu Leu Lys Ile Tyr Gln Asp Asn
```

```
                225                 230                 235                 240
Lys Ile Ile Glu Ser Glu Asn Met His Ile Asp Ile Tyr Leu Tyr Thr
                    245                 250                 255
Ser Leu Ile Val Leu Ile Ser Leu Pro Leu Val Leu
                260                 265

<210> SEQ ID NO 14
<211> LENGTH: 242
<212> TYPE: PRT
<213> ORGANISM: Staphylococcus sp.

<400> SEQUENCE: 14

Met Lys Lys Leu Ile Ser Ile Leu Leu Ile Asn Ile Ile Leu Gly
1               5                   10                  15

Val Ser Asn Asn Ala Ser Ala Gln Gly Asp Ile Gly Ile Asp Asn Leu
                20                  25                  30

Arg Asn Phe Tyr Thr Lys Lys Asp Phe Ile Asn Leu Lys Asp Val Lys
            35                  40                  45

Asp Asn Asp Thr Pro Ile Ala Asn Gln Leu Gln Phe Ser Asn Glu Ser
        50                  55                  60

Tyr Asp Leu Ile Ser Glu Ser Lys Asp Phe Asn Lys Phe Ser Asn Phe
65                  70                  75                  80

Lys Gly Lys Lys Leu Asp Val Phe Gly Ile Ser Tyr Asn Gly Gln Cys
                85                  90                  95

Asn Thr Lys Tyr Ile Tyr Gly Gly Ile Thr Ala Thr Asn Glu Tyr Leu
            100                 105                 110

Asp Lys Pro Arg Asn Ile Pro Ile Asn Ile Trp Ile Asn Gly Asn His
        115                 120                 125

Lys Thr Ile Ser Thr Asn Lys Val Ser Thr Asn Lys Lys Phe Val Thr
    130                 135                 140

Ala Gln Glu Ile Asp Ile Lys Leu Arg Arg Tyr Leu Gln Gly Glu Tyr
145                 150                 155                 160

Asn Ile Tyr Gly His Asn Gly Thr Lys Lys Gly Glu Glu Tyr Gly His
                165                 170                 175

Lys Ser Lys Phe Tyr Ser Gly Phe Asn Ile Gly Lys Val Thr Phe His
            180                 185                 190

Leu Asn Asn Asn Asp Thr Phe Ser Tyr Asp Leu Phe Tyr Thr Gly Asp
        195                 200                 205

Asp Gly Leu Pro Lys Ser Phe Leu Lys Ile Tyr Glu Asp Asn Lys Thr
    210                 215                 220

Val Glu Ser Glu Lys Phe His Leu Asp Val Asp Ile Ser Tyr Lys Glu
225                 230                 235                 240

Thr Lys

<210> SEQ ID NO 15
<211> LENGTH: 240
<212> TYPE: PRT
<213> ORGANISM: Staphylococcus sp.

<400> SEQUENCE: 15

Met Lys Lys Arg Leu Leu Phe Val Ile Val Ile Thr Leu Phe Ile Phe
1               5                   10                  15

Ser Ser Asn His Thr Val Leu Ser Asn Gly Asp Val Gly Pro Gly Asn
                20                  25                  30

Leu Arg Asn Phe Tyr Thr Lys Tyr Glu Tyr Val Asn Leu Lys Asn Val
            35                  40                  45
```

```
Lys Asp Lys Asn Ser Pro Glu Ser His Arg Leu Glu Tyr Ser Tyr Lys
         50                  55                  60

Asn Asp Thr Leu Tyr Ala Glu Phe Asp Asn Glu Tyr Ile Thr Ser Asp
 65                  70                  75                  80

Leu Lys Gly Lys Asn Val Asp Val Phe Gly Ile Ser Tyr Lys Tyr Gly
                 85                  90                  95

Ser Asn Ser Arg Thr Ile Tyr Gly Gly Val Thr Lys Ala Glu Asn Asn
            100                 105                 110

Lys Leu Asp Ser Pro Arg Ile Ile Pro Ile Asn Leu Ile Ile Asn Gly
        115                 120                 125

Lys His Gln Thr Val Thr Thr Lys Ser Val Ser Thr Asp Lys Lys Met
    130                 135                 140

Val Thr Ala Gln Glu Ile Asp Val Lys Leu Arg Lys Tyr Leu Gln Asp
145                 150                 155                 160

Glu Phe Asn Ile Tyr Gly His Asn Asp Thr Gly Lys Gly Lys Glu Tyr
                165                 170                 175

Gly Thr Ser Ser Lys Phe Tyr Ser Gly Phe Asp Lys Gly Ser Val Val
            180                 185                 190

Phe His Met Asn Asp Gly Ser Asn Phe Ser Tyr Asp Leu Phe Tyr Thr
        195                 200                 205

Gly Tyr Gly Leu Pro Glu Ser Phe Leu Lys Ile Tyr Lys Asp Asn Lys
    210                 215                 220

Thr Val Asp Ser Thr Gln Phe His Leu Asp Val Glu Ile Ser Lys Arg
225                 230                 235                 240

<210> SEQ ID NO 16
<211> LENGTH: 239
<212> TYPE: PRT
<213> ORGANISM: Staphylococcus sp.

<400> SEQUENCE: 16

Met Lys Arg Ile Leu Ile Ile Val Val Leu Leu Phe Cys Tyr Ser Gln
 1               5                  10                  15

Asn His Ile Ala Thr Ala Asp Val Gly Val Leu Asn Leu Arg Asn Tyr
             20                  25                  30

Tyr Gly Ser Tyr Pro Ile Glu Asp His Gln Ser Ile Asn Pro Glu Asn
            35                  40                  45

Asn His Leu Ser His Gln Leu Val Phe Ser Met Asp Asn Ser Thr Val
         50                  55                  60

Thr Ala Glu Phe Lys Asn Val Asp Asp Val Lys Lys Phe Lys Asn His
 65                  70                  75                  80

Ala Val Asp Val Tyr Gly Leu Ser Tyr Ser Gly Tyr Cys Leu Lys Asn
                 85                  90                  95

Lys Tyr Ile Tyr Gly Gly Val Thr Leu Ala Gly Asp Tyr Leu Glu Lys
            100                 105                 110

Ser Arg Arg Ile Pro Ile Asn Leu Trp Val Asn Gly Glu His Gln Thr
        115                 120                 125

Ile Ser Thr Asp Lys Val Ser Thr Asn Lys Lys Leu Val Thr Ala Gln
    130                 135                 140

Glu Ile Asp Thr Lys Leu Arg Arg Tyr Leu Gln Glu Glu Tyr Asn Ile
145                 150                 155                 160

Tyr Gly Phe Asn Asp Thr Asn Lys Gly Arg Asn Tyr Gly Asn Lys Ser
                165                 170                 175

Lys Phe Ser Ser Gly Phe Asn Ala Gly Lys Ile Leu Phe His Leu Asn
```

```
                    180                 185                 190
Asp Gly Ser Ser Phe Ser Tyr Asp Leu Phe Asp Thr Gly Thr Gly Gln
                195                 200                 205
Ala Glu Ser Phe Leu Lys Ile Tyr Asn Asp Asn Lys Thr Val Glu Thr
        210                 215                 220
Glu Lys Phe His Leu Asp Val Glu Ile Ser Tyr Lys Asp Glu Ser
225                 230                 235
```

<210> SEQ ID NO 17
<211> LENGTH: 263
<212> TYPE: PRT
<213> ORGANISM: Staphylococcus sp.

<400> SEQUENCE: 17

```
Met Lys Asn Ser Lys Val Met Leu Asn Val Leu Leu Ile Leu Asn
1               5                   10                  15
Leu Ile Ala Ile Cys Ser Val Asn Asn Ala Tyr Ala Asn Glu Glu Asp
                20                  25                  30
Pro Lys Ile Glu Ser Leu Cys Lys Lys Ser Ser Val Gly Pro Ile Ala
            35                  40                  45
Leu His Asn Ile Asn Asp Asp Tyr Ile Asn Asn Arg Arg Phe Thr Thr
        50                  55                  60
Val Lys Ser Ile Val Ser Thr Thr Glu Lys Phe Leu Asp Phe Asp Leu
65                  70                  75                  80
Leu Phe Lys Ser Ile Asn Trp Leu Asp Gly Ile Ser Ala Glu Phe Lys
                85                  90                  95
Asp Leu Lys Glu Phe Ser Ser Ser Ala Ile Ser Lys Glu Phe Leu Gly
            100                 105                 110
Lys Tyr Val Asp Ile Tyr Gly Val Tyr Tyr Lys Ala His Cys His Gly
        115                 120                 125
Glu His Gln Val Asp Thr Ala Cys Thr Tyr Gly Gly Val Thr Pro His
130                 135                 140
Glu Asn Asn Lys Leu Ser Glu Pro Lys Asn Ile Gly Val Ala Val Tyr
145                 150                 155                 160
Lys Asp Asn Val Asn Val Asn Val Asn Thr Phe Ile Val Thr Thr Asp
                165                 170                 175
Lys Lys Lys Val Tyr Ala Gln Glu Leu Asp Ile Lys Val Arg Thr Lys
            180                 185                 190
Leu Asn Asn Ala Tyr Lys Leu Tyr Asp Arg Met Thr Ser Asp Val Gln
        195                 200                 205
Lys Gly Tyr Ile Lys Phe His Ser His Ser Glu His Lys Glu Ser Phe
210                 215                 220
Tyr Tyr Asp Leu Phe Tyr Ile Lys Gly Asn Leu Pro Asp Gln Tyr Leu
225                 230                 235                 240
Gln Ile Tyr Asn Asp Asn Lys Thr Thr Ile Asp Ser Ser Asp Tyr His
                245                 250                 255
Ile Asp Val Tyr Leu Phe Thr
            260
```

<210> SEQ ID NO 18
<211> LENGTH: 257
<212> TYPE: PRT
<213> ORGANISM: Staphylococcus sp.

<400> SEQUENCE: 18

```
Met Lys Asn Ile Lys Lys Leu Met Arg Leu Phe Tyr Ile Ala Ala Ile
```

```
            1               5                  10                 15
        Ile Ile Thr Leu Leu Cys Leu Ile Asn Asn Asn Tyr Val Asn Ala Glu
                        20                  25                 30
        Val Asp Lys Lys Asp Leu Lys Lys Lys Ser Asp Leu Asp Ser Ser Lys
                        35                  40                 45
        Leu Phe Asn Leu Thr Ser Tyr Tyr Thr Asp Ile Thr Trp Gln Leu Asp
         50                          55                 60
        Glu Ser Asn Lys Ile Ser Thr Asp Gln Leu Asn Asn Tyr Ile Ile Leu
         65                  70                  75                 80
        Lys Asn Ile Asp Ile Ser Val Leu Lys Thr Ser Ser Leu Lys Val Glu
                        85                  90                 95
        Phe Asn Ser Ser Asp Leu Ala Asn Gln Phe Lys Gly Lys Asn Ile Asp
                        100                 105                110
        Ile Tyr Gly Leu Tyr Phe Gly Asn Lys Cys Val Gly Leu Thr Glu Glu
                        115                 120                125
        Lys Thr Ser Cys Leu Tyr Gly Gly Val Thr Ile His Asp Gly Asn Gln
                        130                 135                140
        Leu Asp Glu Glu Lys Val Ile Gly Val Asn Gly Phe Lys Asp Gly Val
        145                 150                 155                160
        Gln Gln Glu Gly Phe Val Ile Lys Thr Lys Ala Lys Val Thr Val
                            165                 170                175
        Gln Glu Leu Asp Thr Lys Val Arg Phe Lys Leu Glu Asn Leu Tyr Lys
                        180                 185                190
        Ile Tyr Asn Lys Asp Thr Gly Asn Ile Gln Lys Gly Cys Ile Phe Phe
                        195                 200                205
        His Ser His Asn His Gln Asp Gln Ser Phe Tyr Tyr Asp Leu Tyr Asn
                        210                 215                220
        Val Lys Gly Ser Val Gly Ala Glu Phe Phe Gln Phe Tyr Ser Asp Asn
        225                 230                 235                240
        Arg Thr Val Ser Ser Ser Asn Tyr His Ile Asp Val Phe Leu Tyr Lys
                        245                 250                255
        Asp

<210> SEQ ID NO 19
<211> LENGTH: 132
<212> TYPE: PRT
<213> ORGANISM: Staphylococcus sp.

<400> SEQUENCE: 19

Met Lys Leu Phe Ala Phe Ile Phe Ile Cys Val Lys Ser Cys Ser Leu
        1               5                   10                 15
        Leu Phe Met Leu Asn Gly Asn Pro Lys Pro Glu Gln Leu Asn Lys Ala
                        20                  25                 30
        Ser Glu Phe Thr Gly Leu Met Asp Asn Met Arg Tyr Leu Tyr Asp Asp
                        35                  40                 45
        Lys His Val Ser Glu Thr Asn Ile Lys Ser Gln Glu Lys Phe Leu Gln
                        50                  55                 60
        His Asp Leu Leu Phe Lys Ile Asn Gly Ser Lys Ile Leu Lys Thr Glu
         65                  70                  75                 80
        Phe Asn Asn Lys Ser Leu Ser Asp Lys Tyr Lys Asn Lys Asn Val Asp
                        85                  90                 95
        Leu Phe Gly Thr Asn Tyr Tyr Asn Gln Cys Tyr Phe Ser Leu Asp Asn
                        100                 105                110
        Met Glu Leu Asn Asp Gly Arg Leu Ile Glu Lys Asn Val Tyr Val Trp
```

```
            115                 120                 125

Arg Cys Gly Leu
        130

<210> SEQ ID NO 20
<211> LENGTH: 108
<212> TYPE: PRT
<213> ORGANISM: Staphylococcus sp.

<400> SEQUENCE: 20

Met Tyr Gly Gly Val Val Tyr Glu Asn Glu Arg Asn Ser Leu Ser Phe
1               5                   10                  15

Asp Ile Pro Thr Asn Lys Lys Asn Ile Thr Ala Gln Glu Ile Asp Tyr
            20                  25                  30

Lys Val Arg Asn Tyr Leu Leu Lys His Lys Asn Leu Tyr Glu Phe Asn
        35                  40                  45

Ser Ser Pro Tyr Glu Thr Gly Tyr Ile Lys Phe Ile Glu Gly Ser Gly
    50                  55                  60

His Ser Phe Trp Tyr Asp Leu Met Pro Glu Ser Gly Lys Lys Phe Tyr
65                  70                  75                  80

Pro Thr Lys Tyr Leu Leu Ile Tyr Asn Asp Asn Lys Thr Val Glu Ser
                85                  90                  95

Lys Ser Ile Asn Val Glu Val His Leu Thr Lys Lys
            100                 105

<210> SEQ ID NO 21
<211> LENGTH: 258
<212> TYPE: PRT
<213> ORGANISM: Staphylococcus sp.

<400> SEQUENCE: 21

Met Ser Lys Met Lys Lys Thr Ala Phe Thr Leu Leu Leu Phe Ile Ala
1               5                   10                  15

Leu Thr Leu Thr Thr Ser Pro Leu Val Asn Gly Ser Glu Lys Ser Glu
            20                  25                  30

Glu Ile Asn Glu Lys Asp Leu Arg Lys Lys Ser Glu Leu Gln Gly Thr
        35                  40                  45

Ala Leu Gly Asn Leu Lys Gln Ile Tyr Tyr Asn Glu Lys Ala Lys Thr
    50                  55                  60

Glu Asn Lys Glu Ser His Asp Gln Phe Leu Gln His Thr Ile Leu Phe
65                  70                  75                  80

Lys Gly Phe Phe Thr Asp His Ser Trp Tyr Asn Asp Leu Leu Val Asp
                85                  90                  95

Phe Asp Ser Lys Asp Ile Val Asp Lys Tyr Lys Gly Lys Lys Val Asp
            100                 105                 110

Leu Tyr Phe Ala Tyr Tyr Gly Tyr Gln Cys Ala Gly Gly Thr Pro Asn
        115                 120                 125

Lys Thr Ala Cys Met Tyr Gly Gly Val Thr Leu His Asp Asn Asn Arg
    130                 135                 140

Leu Thr Glu Glu Lys Lys Glu Pro Ile Asn Leu Trp Leu Asp Gly Lys
145                 150                 155                 160

Gln Asn Thr Val Pro Leu Glu Thr Val Lys Thr Asn Lys Lys Val Thr
                165                 170                 175

Val Gln Glu Leu Asp Leu Gln Ala Arg Arg Tyr Leu Gln Glu Lys Tyr
            180                 185                 190

Asn Leu Tyr Asn Ser Asp Val Phe Asp Gly Lys Val Gln Arg Gly Leu
```

-continued

```
                195                 200                 205
Ile Val Phe His Thr Ser Thr Glu Pro Ser Val Asn Tyr Asp Leu Phe
    210                 215                 220

Gly Ala Gln Gly Gln Tyr Ser Asn Thr Leu Leu Arg Ile Tyr Arg Asp
225                 230                 235                 240

Asn Lys Thr Ile Asn Ser Glu Asn Met His Ile Asp Ile Tyr Leu Tyr
                245                 250                 255

Thr Ser
```

<210> SEQ ID NO 22
<211> LENGTH: 255
<212> TYPE: PRT
<213> ORGANISM: Staphylococcus sp.

<400> SEQUENCE: 22

```
Met Pro Ile Trp Arg Cys Asn Ile Lys Lys Gly Ala Ile Lys Met Asn
1               5                   10                  15

Lys Ile Phe Arg Ile Leu Thr Val Ser Leu Phe Phe Thr Phe Leu
                20                  25                  30

Ile Lys Asn Asn Leu Ala Tyr Ala Asp Val Gly Val Ile Asn Leu Arg
                35                  40                  45

Asn Phe Tyr Ala Asn Tyr Glu Pro Glu Lys Leu Gln Gly Val Ser Ser
    50                  55                  60

Gly Asn Phe Ser Thr Ser His Gln Leu Glu Tyr Ile Asp Gly Lys Tyr
65                  70                  75                  80

Thr Leu Tyr Ser Gln Phe His Asn Glu Tyr Glu Ala Lys Arg Leu Lys
                85                  90                  95

Asp His Lys Val Asp Ile Phe Gly Ile Ser Tyr Ser Gly Leu Cys Asn
                100                 105                 110

Thr Lys Tyr Met Gly Gly Ile Thr Leu Ala Asn Gln Asn Leu Asp Lys
                115                 120                 125

Pro Arg Asn Ile Pro Ile Asn Leu Trp Val Asn Gly Lys Gln Asn Thr
    130                 135                 140

Ile Ser Thr Asp Lys Val Ser Thr Gln Lys Lys Glu Val Thr Ala Gln
145                 150                 155                 160

Glu Ile Asp Ile Lys Leu Arg Lys Tyr Leu Gln Asn Glu Tyr Asn Ile
                165                 170                 175

Tyr Gly Phe Asn Lys Thr Lys Lys Gly Gly Glu Tyr Gly Tyr Gln Ser
                180                 185                 190

Lys Phe Asn Ser Gly Phe Asn Lys Gly Lys Ile Thr Phe His Leu Asn
                195                 200                 205

Asn Glu Pro Ser Phe Thr Tyr Asp Leu Phe Tyr Thr Gly Thr Gly Gly
    210                 215                 220

Ala Glu Ser Phe Leu Lys Ile Tyr Asn Asp Asn Lys Thr Ile Asp Ala
225                 230                 235                 240

Glu Asn Phe His Leu Asp Val Glu Ile Ser Tyr Glu Lys Thr Glu
                245                 250                 255
```

<210> SEQ ID NO 23
<211> LENGTH: 259
<212> TYPE: PRT
<213> ORGANISM: Staphylococcus sp.

<400> SEQUENCE: 23

```
Met Leu Asn Lys Ile Leu Leu Leu Leu Phe Ser Val Thr Phe Met Leu
1               5                   10                  15
```

```
Leu Phe Phe Ser Leu His Ser Val Ser Ala Lys Pro Asp Pro Arg Pro
            20                  25                  30

Gly Glu Leu Asn Arg Val Ser Asp Tyr Lys Lys Asn Lys Gly Thr Met
        35                  40                  45

Gly Asn Val Glu Ser Leu Tyr Lys Asp Lys Ala Val Ile Ala Glu Asn
50                  55                  60

Val Lys Asn Thr Arg Gln Phe Leu Gly His Asp Leu Ile Phe Pro Ile
65                  70                  75                  80

Pro Tyr Ser Glu Tyr Lys Glu Val Lys Ser Glu Phe Ile Asn Lys Lys
                85                  90                  95

Thr Ala Asp Lys Phe Lys Asp Lys Arg Leu Asp Val Phe Gly Ile Pro
            100                 105                 110

Tyr Phe Tyr Thr Cys Leu Val Pro Lys Asn Glu Ser Arg Glu Glu Phe
            115                 120                 125

Ile Phe Asp Gly Val Cys Ile Tyr Gly Gly Val Thr Met His Ser Thr
130                 135                 140

Ala Asp Ser Ile Ser Lys Asn Ile Ile Val Pro Val Thr Val Asp Asn
145                 150                 155                 160

Lys Gln Gln Phe Ser Phe Thr Ile Ser Thr Asn Lys Lys Thr Val Thr
                165                 170                 175

Val Gln Glu Leu Asp Tyr Lys Val Arg Asn Trp Leu Thr Asn Asn Lys
            180                 185                 190

Lys Leu Tyr Glu Phe Asp Gly Ser Ala Tyr Glu Thr Gly Tyr Ile Lys
            195                 200                 205

Phe Ile Glu Gln Asn Lys Asp Ser Phe Trp Tyr Asp Leu Phe Pro Lys
210                 215                 220

Lys Asp Leu Val Pro Phe Ile Pro Tyr Lys Phe Val Asn Ile Tyr Gly
225                 230                 235                 240

Asp Asn Lys Thr Ile Asp Ala Ser Ser Val Lys Ile Glu Val His Leu
                245                 250                 255

Thr Thr Met

<210> SEQ ID NO 24
<211> LENGTH: 261
<212> TYPE: PRT
<213> ORGANISM: Staphylococcus sp.

<400> SEQUENCE: 24

Met Lys Leu Phe Ala Phe Ile Phe Ile Cys Val Lys Ser Cys Ser Leu
1               5                   10                  15

Leu Phe Met Leu Asn Gly Asn Pro Arg Pro Glu Gln Leu Asn Lys Ala
            20                  25                  30

Ser Glu Phe Ser Gly Leu Met Asp Asn Met Arg Tyr Leu Tyr Asp Asp
        35                  40                  45

Lys His Val Ser Glu Thr Asn Ile Lys Ala Gln Glu Lys Phe Leu Gln
    50                  55                  60

His Asp Leu Leu Phe Lys Ile Asn Gly Ser Lys Ile Asp Gly Ser Lys
65                  70                  75                  80

Ile Leu Lys Thr Glu Phe Asn Asn Lys Ser Leu Ser Lys Tyr Lys
                85                  90                  95

Asn Lys Asn Val Asp Leu Phe Gly Thr Asn Tyr Tyr Asn Gln Cys Tyr
            100                 105                 110

Phe Ser Ala Asp Asn Met Glu Leu Asn Asp Gly Arg Leu Ile Glu Lys
            115                 120                 125
```

```
Thr Cys Met Tyr Gly Gly Val Thr Glu His Asp Gly Asn Gln Ile Asp
            130                 135                 140

Lys Asn Asn Leu Thr Asp Asn Ser His Asn Ile Leu Ile Lys Val Tyr
145                 150                 155                 160

Glu Asn Glu Arg Asn Thr Leu Ser Phe Asp Ile Ser Thr Asn Met Lys
                165                 170                 175

Asn Ile Thr Ala Gln Glu Ile Asp Tyr Lys Val Arg Asn Tyr Leu Leu
            180                 185                 190

Lys His Lys Asn Leu Tyr Glu Phe Asn Ser Ser Pro Tyr Glu Ser Gly
            195                 200                 205

Tyr Ile Lys Phe Ile Glu Gly Asn Gly His Ser Phe Trp Tyr Asp Met
            210                 215                 220

Met Pro Glu Ser Gly Lys Phe Tyr Pro Thr Lys Tyr Leu Leu Ile
225                 230                 235                 240

Tyr Asn Asp Asn Lys Thr Val Glu Ser Lys Ser Ile Asn Val Glu Val
                245                 250                 255

His Leu Thr Lys Lys
            260

<210> SEQ ID NO 25
<211> LENGTH: 251
<212> TYPE: PRT
<213> ORGANISM: Streptococcus pyrogenes

<400> SEQUENCE: 25

Met Glu Asn Asn Lys Lys Val Leu Lys Lys Met Val Phe Phe Val Leu
1               5                   10                  15

Val Thr Phe Leu Gly Leu Thr Ile Ser Gln Glu Val Phe Ala Gln Gln
            20                  25                  30

Asp Pro Asp Pro Ser Gln Leu His Arg Ser Ser Leu Val Lys Asn Leu
            35                  40                  45

Gln Asn Ile Tyr Phe Leu Tyr Glu Gly Asp Pro Val Thr His Glu Asn
    50                  55                  60

Val Lys Ser Val Asp Gln Leu Leu Ser His Asp Leu Ile Tyr Asn Val
65                  70                  75                  80

Ser Gly Pro Asn Tyr Asp Lys Leu Lys Thr Glu Leu Lys Asn Gln Glu
                85                  90                  95

Met Ala Thr Leu Phe Lys Asp Lys Asn Val Asp Ile Tyr Gly Val Glu
            100                 105                 110

Tyr Tyr His Leu Cys Tyr Leu Cys Glu Asn Ala Glu Arg Ser Ala Cys
            115                 120                 125

Ile Tyr Gly Gly Val Thr Asn His Glu Gly Asn His Leu Glu Ile Pro
            130                 135                 140

Lys Lys Ile Val Val Lys Val Ser Ile Asp Gly Ile Gln Ser Leu Ser
145                 150                 155                 160

Phe Asp Ile Glu Thr Asn Lys Lys Met Val Thr Ala Gln Glu Leu Asp
                165                 170                 175

Tyr Lys Val Arg Lys Tyr Leu Thr Asp Asn Lys Gln Leu Tyr Thr Asn
            180                 185                 190

Gly Pro Ser Lys Tyr Glu Thr Gly Tyr Ile Lys Phe Ile Pro Lys Asn
                195                 200                 205

Lys Glu Ser Phe Trp Phe Asp Phe Phe Pro Glu Pro Glu Phe Thr Gln
            210                 215                 220

Ser Lys Tyr Leu Met Ile Tyr Lys Asp Asn Glu Thr Leu Asp Ser Asn
```

```
                225                 230                 235                 240

Thr Ser Gln Ile Glu Val Tyr Leu Thr Thr Lys
                245                 250

<210> SEQ ID NO 26
<211> LENGTH: 398
<212> TYPE: PRT
<213> ORGANISM: Streptococcus pyrogenes

<400> SEQUENCE: 26

Met Asn Lys Lys Lys Leu Gly Ile Arg Leu Ser Leu Leu Ala Leu
 1               5                  10                  15

Gly Gly Phe Val Leu Ala Asn Pro Val Phe Ala Asp Gln Asn Phe Ala
                20                  25                  30

Arg Asn Glu Lys Glu Ala Lys Asp Ser Ala Ile Thr Phe Ile Gln Lys
                35                  40                  45

Ser Ala Ala Ile Lys Ala Gly Ala Arg Ser Ala Glu Asp Ile Lys Leu
                50                  55                  60

Asp Lys Val Asn Leu Gly Gly Glu Leu Ser Gly Ser Asn Met Tyr Val
65                  70                  75                  80

Tyr Asn Ile Ser Thr Gly Gly Phe Val Ile Val Ser Gly Asp Lys Arg
                85                  90                  95

Ser Pro Glu Ile Leu Gly Tyr Ser Thr Ser Gly Ser Phe Asp Ala Asn
                100                 105                 110

Gly Lys Glu Asn Ile Ala Ser Phe Met Glu Ser Tyr Val Glu Gln Ile
                115                 120                 125

Lys Glu Asn Lys Lys Leu Asp Thr Thr Tyr Ala Gly Thr Ala Glu Ile
                130                 135                 140

Lys Gln Pro Val Val Lys Ser Leu Leu Asp Ser Lys Gly Ile His Tyr
145                 150                 155                 160

Asn Gln Gly Asn Pro Tyr Asn Leu Leu Thr Pro Val Ile Glu Lys Val
                165                 170                 175

Lys Pro Gly Glu Gln Ser Phe Val Gly Gln His Ala Ala Thr Gly Cys
                180                 185                 190

Val Ala Thr Ala Thr Ala Gln Ile Met Lys Tyr His Asn Tyr Pro Asn
                195                 200                 205

Lys Gly Leu Lys Asp Tyr Thr Tyr Thr Leu Ser Ser Asn Asn Pro Tyr
                210                 215                 220

Phe Asn His Pro Lys Asn Leu Phe Ala Ala Ile Ser Thr Arg Gln Tyr
225                 230                 235                 240

Asn Trp Asn Asn Ile Leu Pro Thr Tyr Ser Gly Arg Glu Ser Asn Val
                245                 250                 255

Gln Lys Met Ala Ile Ser Glu Leu Met Ala Asp Val Gly Ile Ser Val
                260                 265                 270

Asp Met Asp Tyr Gly Pro Ser Ser Gly Ser Ala Gly Ser Ser Arg Val
                275                 280                 285

Gln Arg Ala Leu Lys Glu Asn Phe Gly Tyr Asn Gln Ser Val His Gln
                290                 295                 300

Ile Asn Arg Ser Asp Phe Ser Lys Gln Asp Trp Glu Ala Gln Ile Asp
305                 310                 315                 320

Lys Glu Leu Ser Gln Asn Gln Pro Val Tyr Tyr Gln Gly Val Gly Lys
                325                 330                 335

Val Gly Gly His Ala Phe Val Ile Asp Gly Ala Asp Gly Arg Asn Phe
                340                 345                 350
```

-continued

Tyr His Val Asn Trp Gly Trp Gly Gly Val Ser Asp Gly Phe Phe Arg
                355                 360                 365

Leu Asp Ala Leu Asn Pro Ser Ala Leu Gly Thr Gly Gly Ala Gly
    370                 375                 380

Gly Phe Asn Gly Tyr Gln Ser Ala Val Val Gly Ile Lys Pro
385                 390                 395

<210> SEQ ID NO 27
<211> LENGTH: 234
<212> TYPE: PRT
<213> ORGANISM: Streptococcus pyrogenes

<400> SEQUENCE: 27

Met Lys Lys Ile Asn Ile Ile Lys Ile Val Phe Ile Ile Thr Val Ile
1               5                   10                  15

Leu Ile Ser Thr Ile Ser Pro Ile Ile Lys Ser Asp Ser Lys Lys Asp
            20                  25                  30

Ile Ser Asn Val Lys Ser Asp Leu Leu Tyr Ala Tyr Thr Ile Thr Pro
        35                  40                  45

Tyr Asp Tyr Lys Asp Cys Arg Val Asn Phe Ser Thr Thr His Thr Leu
    50                  55                  60

Asn Ile Asp Thr Gln Lys Tyr Arg Gly Lys Asp Tyr Tyr Ile Ser Ser
65                  70                  75                  80

Glu Met Ser Tyr Glu Ala Ser Gln Lys Phe Lys Arg Asp Asp His Val
                85                  90                  95

Asp Val Phe Gly Leu Phe Tyr Ile Leu Asn Ser His Thr Gly Glu Tyr
            100                 105                 110

Ile Tyr Gly Gly Ile Thr Pro Ala Gln Asn Asn Lys Val Asn His Lys
        115                 120                 125

Leu Leu Gly Asn Leu Phe Ile Ser Gly Glu Ser Gln Gln Asn Leu Asn
    130                 135                 140

Asn Lys Ile Ile Leu Glu Lys Asp Ile Val Thr Phe Gln Glu Ile Asp
145                 150                 155                 160

Phe Lys Ile Arg Lys Tyr Leu Met Asp Asn Tyr Lys Ile Tyr Asp Ala
                165                 170                 175

Thr Ser Pro Tyr Val Ser Gly Arg Ile Glu Ile Gly Thr Lys Asp Gly
            180                 185                 190

Lys His Glu Gln Ile Asp Leu Phe Asp Ser Pro Asn Glu Gly Thr Arg
        195                 200                 205

Ser Asp Ile Phe Ala Lys Tyr Lys Asp Asn Arg Ile Ile Asn Met Lys
    210                 215                 220

Asn Phe Ser His Phe Asp Ile Tyr Leu Glu
225                 230

<210> SEQ ID NO 28
<211> LENGTH: 260
<212> TYPE: PRT
<213> ORGANISM: Staphylococcus sp.

<400> SEQUENCE: 28

Met Asn Lys Arg Ile Arg Ile Leu Val Val Ala Cys Val Val Phe Cys
1               5                   10                  15

Ala Gln Leu Leu Ser Ile Ser Val Phe Ala Ser Ser Gln Pro Asp Pro
            20                  25                  30

Thr Pro Glu Gln Leu Asn Lys Ser Ser Gln Phe Thr Gly Val Met Gly
        35                  40                  45

-continued

Asn Leu Arg Cys Leu Tyr Asp Asn His Phe Val Glu Gly Thr Asn Val
 50                  55                  60

Arg Ser Thr Gly Gln Leu Leu Gln His Asp Leu Ile Phe Pro Ile Lys
 65                  70                  75                  80

Asp Leu Lys Leu Lys Asn Tyr Asp Ser Val Lys Thr Glu Phe Asn Ser
                 85                  90                  95

Lys Asp Leu Ala Ala Lys Tyr Lys Asn Lys Asp Val Asp Ile Phe Gly
            100                 105                 110

Ser Asn Tyr Tyr Tyr Asn Cys Tyr Tyr Ser Glu Gly Asn Ser Cys Lys
        115                 120                 125

Asn Ala Lys Lys Thr Cys Met Tyr Gly Gly Val Thr Glu His His Arg
130                 135                 140

Asn Gln Ile Glu Gly Lys Phe Pro Asn Ile Thr Val Lys Val Tyr Glu
145                 150                 155                 160

Asp Asn Glu Asn Ile Leu Ser Phe Asp Ile Thr Thr Asn Lys Lys Gln
                165                 170                 175

Val Thr Val Gln Glu Leu Asp Cys Lys Thr Arg Lys Ile Leu Val Ser
            180                 185                 190

Arg Lys Asn Leu Tyr Glu Phe Asn Asn Ser Pro Tyr Glu Thr Gly Tyr
        195                 200                 205

Ile Lys Phe Ile Glu Ser Ser Gly Asp Ser Phe Trp Tyr Asp Met Met
210                 215                 220

Pro Ala Pro Gly Ala Ile Phe Asp Gln Ser Lys Tyr Leu Met Leu Tyr
225                 230                 235                 240

Asn Asp Asn Lys Thr Val Ser Ser Ser Ala Ile Ala Ile Glu Val His
                245                 250                 255

Leu Thr Lys Lys
            260

<210> SEQ ID NO 29
<211> LENGTH: 210
<212> TYPE: PRT
<213> ORGANISM: Streptococcus pyrogenes

<400> SEQUENCE: 29

Asp Glu Asn Leu Lys Asp Leu Lys Arg Ser Leu Arg Phe Ala Tyr Asn
 1               5                  10                  15

Ile Thr Pro Cys Asp Tyr Glu Asn Val Glu Ile Ala Phe Val Thr Thr
                 20                  25                  30

Asn Ser Ile His Ile Asn Thr Lys Gln Lys Arg Ser Glu Cys Ile Leu
             35                  40                  45

Tyr Val Asp Ser Ile Val Ser Leu Gly Ile Thr Asp Gln Phe Ile Lys
 50                  55                  60

Gly Asp Lys Val Asp Val Phe Gly Leu Pro Tyr Asn Phe Ser Pro Pro
 65                  70                  75                  80

Tyr Val Asp Asn Ile Tyr Gly Gly Ile Val Lys His Ser Asn Gln Gly
                 85                  90                  95

Asn Lys Ser Leu Gln Phe Val Gly Ile Leu Asn Gln Asp Gly Lys Glu
            100                 105                 110

Thr Tyr Leu Pro Ser Glu Val Val Arg Ile Lys Lys Lys Gln Phe Thr
        115                 120                 125

Leu Gln Glu Phe Asp Phe Lys Ile Arg Lys Phe Leu Met Glu Lys Tyr
130                 135                 140

Asn Ile Tyr Asp Ser Glu Ser Arg Tyr Thr Ser Gly Ser Leu Phe Leu
145                 150                 155                 160

```
Ala Thr Lys Asp Ser Lys His Tyr Glu Val Asp Leu Phe Asn Lys Asp
            165                 170                 175

Asp Lys Leu Leu Ser Arg Asp Ser Phe Phe Lys Arg Tyr Lys Asp Asn
            180                 185                 190

Lys Ile Phe Asn Ser Glu Glu Ile Ser His Phe Asp Ile Tyr Leu Lys
            195                 200                 205

Thr Tyr
    210

<210> SEQ ID NO 30
<211> LENGTH: 236
<212> TYPE: PRT
<213> ORGANISM: Streptococcus pyrogenes

<400> SEQUENCE: 30

Met Arg Tyr Asn Cys Arg Tyr Ser His Ile Asp Lys Lys Ile Tyr Ser
1               5                   10                  15

Met Ile Ile Cys Leu Ser Phe Leu Leu Tyr Ser Asn Val Val Gln Ala
            20                  25                  30

Asn Ser Tyr Asn Thr Thr Asn Arg His Asn Leu Glu Ser Leu Tyr Lys
        35                  40                  45

His Asp Ser Asn Leu Ile Glu Ala Asp Ser Ile Lys Asn Ser Pro Asp
    50                  55                  60

Ile Val Thr Ser His Met Leu Lys Tyr Ser Val Lys Asp Lys Asn Leu
65                  70                  75                  80

Ser Val Phe Phe Glu Lys Asp Trp Ile Ser Gln Glu Phe Lys Asp Lys
                85                  90                  95

Glu Val Asp Ile Tyr Ala Leu Ser Ala Gln Glu Val Cys Glu Cys Pro
            100                 105                 110

Gly Lys Arg Tyr Glu Ala Phe Gly Gly Ile Thr Leu Thr Asn Ser Glu
        115                 120                 125

Lys Lys Glu Ile Lys Val Pro Val Asn Val Trp Asp Lys Ser Lys Gln
    130                 135                 140

Gln Pro Pro Met Phe Ile Thr Val Asn Lys Pro Lys Val Thr Ala Gln
145                 150                 155                 160

Glu Val Asp Ile Lys Val Arg Lys Leu Leu Ile Lys Lys Tyr Asp Ile
                165                 170                 175

Tyr Asn Asn Arg Glu Gln Lys Tyr Ser Lys Gly Thr Val Thr Leu Asp
            180                 185                 190

Leu Asn Ser Gly Lys Asp Ile Val Phe Asp Leu Tyr Tyr Phe Gly Asn
        195                 200                 205

Gly Asp Phe Asn Ser Met Leu Lys Ile Tyr Ser Asn Asn Glu Arg Ile
    210                 215                 220

Asp Ser Thr Gln Phe His Val Asp Val Ser Ile Ser
225                 230                 235

<210> SEQ ID NO 31
<211> LENGTH: 209
<212> TYPE: PRT
<213> ORGANISM: Streptococcus pyrogenes

<400> SEQUENCE: 31

Leu Glu Val Asp Asn Asn Ser Leu Leu Arg Asn Ile Tyr Ser Thr Ile
1               5                   10                  15

Val Tyr Glu Tyr Ser Asp Thr Val Ile Asp Phe Lys Thr Ser His Asn
            20                  25                  30
```

```
Leu Val Thr Lys Lys Leu Asp Val Arg Asp Ala Arg Asp Phe Phe Ile
        35                  40                  45

Asn Ser Glu Met Asp Glu Tyr Ala Ala Asn Asp Phe Lys Ala Gly Asp
    50                  55                  60

Lys Ile Ala Val Phe Ser Val Pro Phe Asp Trp Asn Tyr Leu Ser Lys
65                  70                  75                  80

Gly Lys Val Thr Ala Tyr Thr Tyr Gly Gly Ile Thr Pro Tyr Gln Lys
                85                  90                  95

Thr Ser Ile Pro Lys Asn Ile Pro Val Asn Leu Trp Ile Asn Arg Lys
            100                 105                 110

Gln Ile Pro Val Pro Tyr Asn Gln Ile Ser Thr Asn Lys Thr Thr Val
        115                 120                 125

Thr Ala Gln Glu Ile Asp Leu Lys Val Arg Lys Phe Leu Ile Ala Gln
    130                 135                 140

His Gln Leu Tyr Ser Ser Gly Ser Ser Tyr Lys Ser Gly Lys Leu Val
145                 150                 155                 160

Phe His Thr Asn Asp Asn Ser Asp Lys Tyr Ser Leu Asp Leu Phe Tyr
                165                 170                 175

Thr Gly Tyr Arg Asp Lys Glu Ser Ile Phe Lys Val Tyr Lys Asp Asn
            180                 185                 190

Lys Ser Phe Asn Ile Asp Lys Ile Gly His Leu Asp Ile Glu Ile Asp
        195                 200                 205

Ser
```

<210> SEQ ID NO 32
<211> LENGTH: 209
<212> TYPE: PRT
<213> ORGANISM: Streptococcus pyrogenes

<400> SEQUENCE: 32

```
Gly Leu Glu Val Asp Asn Asn Ser Leu Leu Arg Asn Ile Tyr Ser Thr
1               5                   10                  15

Ile Val Tyr Glu Tyr Ser Asp Ile Val Ile Asp Phe Lys Thr Ser His
                20                  25                  30

Asn Leu Val Thr Lys Lys Leu Asp Val Arg Asp Ala Arg Asp Phe Phe
        35                  40                  45

Ile Asn Ser Glu Met Asp Glu Tyr Ala Ala Asn Asp Phe Lys Thr Gly
    50                  55                  60

Asp Lys Ile Ala Val Phe Ser Val Pro Phe Asp Trp Asn Tyr Leu Ser
65                  70                  75                  80

Lys Gly Lys Val Thr Ala Tyr Thr Tyr Gly Gly Ile Thr Pro Tyr Gln
                85                  90                  95

Lys Thr Ser Ile Pro Lys Asn Ile Pro Val Asn Leu Trp Ile Asn Gly
            100                 105                 110

Lys Gln Ile Ser Val Pro Tyr Asn Glu Ile Ser Thr Asn Lys Thr Thr
        115                 120                 125

Val Thr Ala Gln Glu Ile Asp Leu Lys Val Arg Lys Phe Leu Ile Ala
    130                 135                 140

Gln His Gln Leu Ser Ser Gly Ser Ser Tyr Lys Ser Gly Arg Leu Val
145                 150                 155                 160

Phe His Thr Asn Asp Asn Ser Asp Lys Tyr Ser Phe Asp Leu Phe Tyr
                165                 170                 175

Val Gly Tyr Arg Asp Lys Glu Ser Ile Phe Lys Asn Tyr Lys Asp Asn
            180                 185                 190
```

```
Lys Ser Phe Asn Ile Asp Lys Ile Gly His Leu Asp Ile Glu Ile Asp
        195                 200                 205
Ser

<210> SEQ ID NO 33
<211> LENGTH: 150
<212> TYPE: PRT
<213> ORGANISM: Yersinia sp.

<400> SEQUENCE: 33

Met Lys Lys Lys Phe Leu Ser Leu Leu Thr Leu Thr Phe Phe Ser Gly
1               5                   10                  15

Leu Ala Leu Ala Ala Asp Tyr Asp Asn Thr Leu Asn Ser Ile Pro Ser
            20                  25                  30

Leu Arg Ile Pro Asn Ile Glu Thr Tyr Thr Gly Thr Ile Gln Gly Lys
        35                  40                  45

Gly Glu Val Cys Ile Arg Gly Asn Lys Glu Gly Lys Ser Arg Gly Gly
    50                  55                  60

Glu Leu Tyr Ala Val Leu Arg Ser Thr Asn Ala Asn Ala Asp Met Thr
65                  70                  75                  80

Leu Ile Leu Leu Cys Ser Ile Arg Asp Gly Trp Lys Glu Val Lys Arg
                85                  90                  95

Ser Asp Ile Asp Arg Pro Leu Arg Tyr Glu Asp Tyr Tyr Thr Pro Gly
            100                 105                 110

Ala Leu Ser Trp Ile Trp Glu Ile Lys Asn Asn Ser Ser Glu Ala Ser
        115                 120                 125

Asp Tyr Ser Leu Ser Ala Thr Val His Asp Asp Lys Glu Asp Ser Asp
    130                 135                 140

Val Leu Met Lys Cys Pro
145                 150

<210> SEQ ID NO 34
<211> LENGTH: 231
<212> TYPE: PRT
<213> ORGANISM: Staphylococcus sp.

<400> SEQUENCE: 34

Met Lys Leu Lys Thr Leu Ala Lys Ala Thr Leu Ala Leu Ser Leu Leu
1               5                   10                  15

Thr Thr Gly Val Ile Thr Leu Glu Ser Gln Ala Val Lys Ala Ala Glu
            20                  25                  30

Lys Gln Glu Arg Val Gln His Leu Tyr Asp Ile Lys Asp Leu Tyr Arg
        35                  40                  45

Tyr Tyr Ser Ala Pro Ser Phe Glu Tyr Ser Asn Ile Ser Gly Lys Val
    50                  55                  60

Glu Asn Tyr Asn Gly Ser Asn Val Val Arg Phe Asn Gln Lys Asp Gln
65                  70                  75                  80

Asn His Gln Leu Phe Leu Leu Gly Lys Asp Lys Glu Gln Tyr Lys Glu
                85                  90                  95

Gly Leu Gln Gly Lys Asp Val Phe Val Val Gln Glu Leu Ile Asp Pro
            100                 105                 110

Asn Gly Arg Leu Ser Thr Val Gly Gly Val Thr Lys Lys Asn Asn Lys
        115                 120                 125

Thr Ser Glu Thr Lys Thr His Leu Leu Val Asn Lys Val Asp Gly Gly
    130                 135                 140
```

```
Asn Leu Asp Ala Ser Ile Asp Ser Phe Leu Ile Gln Lys Glu Glu Ile
145                 150                 155                 160

Ser Leu Lys Glu Leu Asp Phe Lys Ile Arg Gln Gln Leu Val Glu Lys
                165                 170                 175

Tyr Gly Leu Tyr Gln Gly Thr Ser Lys Tyr Gly Lys Ile Thr Ile Asn
            180                 185                 190

Leu Lys Asp Glu Lys Arg Glu Val Ile Asp Leu Ser Asp Lys Leu Glu
        195                 200                 205

Phe Glu Arg Met Gly Asp Val Leu Asn Ser Lys Asp Ile Lys Gly Ile
210                 215                 220

Ser Val Thr Ile Asn Gln Ile
225                 230
```

<210> SEQ ID NO 35
<211> LENGTH: 231
<212> TYPE: PRT
<213> ORGANISM: Staphylococcus sp.

<400> SEQUENCE: 35

```
Met Lys Leu Lys Thr Leu Ala Lys Ala Thr Leu Ala Leu Gly Leu Leu
1               5                   10                  15

Thr Thr Gly Val Ile Thr Ser Glu Gly Gln Ala Val Gln Ala Ala Glu
                20                  25                  30

Lys Gln Glu Arg Val Gln His Leu His Asp Ile Arg Asp Leu His Arg
            35                  40                  45

Tyr Tyr Ser Ser Glu Ser Phe Glu Tyr Ser Asn Val Ser Gly Lys Val
        50                  55                  60

Glu Asn Tyr Asn Gly Ser Asn Val Val Arg Phe Asn Pro Lys Asp Gln
65                  70                  75                  80

Asn His Gln Leu Phe Leu Leu Gly Lys Asp Lys Glu Gln Tyr Lys Glu
                85                  90                  95

Gly Leu Gln Gly Gln Asn Val Phe Val Gln Glu Leu Ile Asp Pro
            100                 105                 110

Asn Gly Arg Leu Ser Thr Val Gly Gly Val Thr Lys Lys Asn Asn Lys
        115                 120                 125

Thr Ser Glu Thr Asn Thr Pro Leu Phe Val Asn Lys Val Asn Gly Glu
130                 135                 140

Asp Leu Asp Ala Ser Ile Asp Ser Phe Leu Ile Gln Lys Glu Glu Ile
145                 150                 155                 160

Ser Leu Lys Glu Leu Asp Phe Lys Ile Arg Gln Gln Leu Val Asn Asn
                165                 170                 175

Tyr Gly Leu Tyr Lys Gly Thr Ser Lys Tyr Gly Lys Ile Ile Ile Asn
            180                 185                 190

Leu Lys Asp Glu Asn Lys Val Glu Ile Asp Leu Gly Asp Lys Leu Gln
        195                 200                 205

Phe Glu Arg Met Gly Asp Val Leu Asn Ser Lys Asp Ile Arg Gly Ile
210                 215                 220

Ser Val Thr Ile Asn Gln Ile
225                 230
```

<210> SEQ ID NO 36
<211> LENGTH: 233
<212> TYPE: PRT
<213> ORGANISM: Staphylococcus sp.

<400> SEQUENCE: 36

```
Met Lys Met Thr Ala Ile Ala Lys Ala Ser Leu Ala Leu Ser Ile Leu
1               5                   10                  15

Ala Thr Gly Val Ile Thr Ser Thr Ala Gln Thr Val Asn Ala Ser Glu
            20                  25                  30

His Glu Ser Lys Tyr Glu Asn Val Lys Asp Ile Phe Asp Lys Arg Asp
        35                  40                  45

Thr Tyr Ser Arg Ala Ser Lys Glu Leu Lys Asn Val Thr Gly Tyr Arg
    50                  55                  60

Ser Lys Gly Gly Lys His Tyr Leu Ile Phe Asp Lys Asn Arg Lys
65                  70                  75                  80

Phe Thr Arg Ile Gln Ile Phe Gly Lys Asp Ile Glu Arg Ile Lys Lys
                85                  90                  95

Arg Lys Asn Pro Gly Leu Asp Ile Phe Val Lys Glu Ala Glu Asn
            100                 105                 110

Arg Asn Gly Thr Val Tyr Ser Tyr Gly Gly Val Thr Leu Leu Met Gln
            115                 120                 125

Gly Ala Tyr Tyr Asp Tyr Leu Ser Ala Pro Arg Phe Val Ile Lys Lys
    130                 135                 140

Glu Val Gly Ala Gly Val Ser Val His Val Lys Arg Tyr Tyr Ile Tyr
145                 150                 155                 160

Lys Glu Glu Ile Ser Leu Lys Glu Leu Asp Phe Lys Leu Arg Gln Tyr
                165                 170                 175

Leu Ile Gln Asp Phe Asp Leu Tyr Lys Lys Phe Pro Lys Ala Ser Lys
            180                 185                 190

Ile Lys Val Thr Met Lys Asp Gly Gly Tyr Tyr Thr Phe Glu Leu Asn
            195                 200                 205

Lys Lys Leu Gln Thr Asn Arg Met Ser Asp Val Ile Asp Gly Arg Asn
210                 215                 220

Ile Glu Lys Ile Glu Ala Asn Ile Arg
225                 230

<210> SEQ ID NO 37
<211> LENGTH: 227
<212> TYPE: PRT
<213> ORGANISM: Staphylococcus sp.

<400> SEQUENCE: 37

Met Lys Leu Thr Ala Leu Ala Lys Val Thr Leu Ala Leu Gly Ile Leu
1               5                   10                  15

Thr Thr Gly Thr Leu Thr Thr Glu Ala His Ser Gly His Ala Lys Gln
            20                  25                  30

Asn Gln Lys Ser Val Asn Lys His Asp Lys Glu Ala Leu His Arg Tyr
        35                  40                  45

Tyr Thr Gly Asn Phe Lys Glu Met Lys Asn Ile Asn Ala Leu Arg His
    50                  55                  60

Gly Lys Asn Asn Leu Arg Phe Lys Tyr Arg Gly Met Lys Thr Gln Val
65                  70                  75                  80

Leu Leu Pro Asx Asp Glu Tyr Arg Lys Tyr Gln Gln Arg Arg His Thr
                85                  90                  95

Gly Leu Asp Val Phe Phe Asn Gln Glu Arg Arg Asp Lys His Asp Ile
            100                 105                 110

Ser Tyr Thr Val Gly Gly Val Thr Lys Thr Asn Lys Thr Ser Gly Phe
        115                 120                 125

Val Ser Thr Pro Arg Leu Asn Val Thr Lys Glu Lys Gly Glu Asp Ala
    130                 135                 140
```

Phe Val Lys Gly Tyr Pro Tyr Asp Ile Lys Lys Glu Glu Ile Ser Leu
145                 150                 155                 160

Lys Glu Leu Asp Phe Lys Leu Arg Lys His Leu Ile Glu Lys Tyr Gly
                165                 170                 175

Leu Tyr Lys Thr Leu Ser Lys Asp Gly Arg Ile Lys Ile Ser Leu Lys
            180                 185                 190

Asp Gly Ser Phe Tyr Asn Leu Asp Leu Arg Thr Lys Leu Lys Phe Lys
                195                 200                 205

His Met Gly Glu Val Ile Asp Ser Lys Gln Ile Lys Asp Ile Glu Val
            210                 215                 220

Asn Leu Lys
225

<210> SEQ ID NO 38
<211> LENGTH: 232
<212> TYPE: PRT
<213> ORGANISM: Staphylococcus sp.

<400> SEQUENCE: 38

Met Lys Leu Thr Ala Ile Ala Lys Ala Thr Leu Ala Leu Gly Ile Leu
1               5                   10                  15

Thr Thr Gly Val Met Thr Ala Glu Ser Gln Thr Val Asn Ala Lys Val
                20                  25                  30

Lys Leu Asp Glu Thr Gln Arg Lys Tyr Tyr Ile Asn Met Leu Lys Asp
            35                  40                  45

Tyr Tyr Ser Gln Glu Ser Tyr Glu Ser Thr Asn Ile Ser Val Lys Ser
50                  55                  60

Glu Asp Tyr Tyr Gly Ser Asn Val Leu Asn Phe Asn Gln Arg Asn Lys
65                  70                  75                  80

Asn Phe Lys Val Phe Leu Ile Gly Asp Asp Arg Asn Lys Tyr Lys Glu
                85                  90                  95

Leu Thr His Gly Arg Asp Val Phe Ala Val Pro Glu Leu Ile Asp Thr
            100                 105                 110

Lys Gly Gly Ile Tyr Ser Val Gly Gly Ile Thr Lys Lys Asn Val Arg
            115                 120                 125

Ser Val Phe Gly Tyr Val Ser His Pro Gly Leu Gln Val Lys Lys Val
            130                 135                 140

Asp Pro Lys Asp Gly Phe Ser Ile Lys Glu Leu Phe Phe Ile Gln Lys
145                 150                 155                 160

Glu Glu Val Ser Leu Lys Glu Leu Asp Phe Lys Ile Arg Lys Met Leu
                165                 170                 175

Val Glu Lys Tyr Arg Leu Tyr Lys Gly Ala Ser Asp Lys Gly Arg Ile
            180                 185                 190

Val Ile Asn Met Lys Asp Glu Lys His Glu Ile Asp Leu Ser Glu
            195                 200                 205

Lys Leu Ser Phe Asp Arg Met Phe Asp Val Leu Asp Ser Lys Gln Ile
210                 215                 220

Lys Asn Ile Glu Val Asn Leu Asn
225                 230

<210> SEQ ID NO 39
<211> LENGTH: 254
<212> TYPE: PRT
<213> ORGANISM: Homo sapiens

<400> SEQUENCE: 39

```
Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
                20                  25                  30

Ala Gly Leu Leu Leu Leu Leu Leu Ala Ala Cys Ala Val Phe
            35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 40
<211> LENGTH: 67
<212> TYPE: PRT
<213> ORGANISM: Homo sapiens

<400> SEQUENCE: 40

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
                20                  25                  30

Gly Leu Gly Leu Leu Leu Cys Phe Thr Tyr Ile Cys Leu His Phe Ser
            35                  40                  45

Ala Leu Gln Val Ser His Arg Tyr Pro Arg Ile Gln Ser Ile Lys Val
        50                  55                  60

Gln Phe Thr
65
```